US012583917B2

(12) United States Patent
Li et al.

(10) Patent No.: US 12,583,917 B2
(45) **Date of Patent: *Mar. 24, 2026**

(54) IL17A ANTIBODIES AND ANTAGONISTS FOR VETERINARY USE

(71) Applicant: Elanco US Inc., Greenfield, IN (US)

(72) Inventors: Shyr Jiann Li, Millbrae, CA (US); Lam Nguyen, Union City, CA (US); Lan Yang, Union City, CA (US); Hangjun Zhan, Foster City, CA (US)

(73) Assignee: Elanco US Inc., Greenfield, IN (US)

( * ) Notice: Subject to any disclaimer, the term of this patent is extended or adjusted under 35 U.S.C. 154(b) by 1030 days.

This patent is subject to a terminal disclaimer.

(21) Appl. No.: 17/687,083

(22) Filed: Mar. 4, 2022

(65) Prior Publication Data

US 2022/0185879 A1      Jun. 16, 2022

Related U.S. Application Data

(63) Continuation of application No. 16/621,012, filed as application No. PCT/US2018/038033 on Jun. 18, 2018, now Pat. No. 11,299,540.

(60) Provisional application No. 62/521,514, filed on Jun. 18, 2017.

(51) Int. Cl.
| | |
|---|---|
| *C07K 16/24* | (2006.01) |
| *A61K 39/395* | (2006.01) |
| *C12N 15/63* | (2006.01) |
| *A61K 39/00* | (2006.01) |

(52) U.S. Cl.
CPC ........ *C07K 16/244* (2013.01); *A61K 39/3955* (2013.01); *C12N 15/63* (2013.01); *A61K 2039/505* (2013.01); *C07K 2317/24* (2013.01); *C07K 2317/31* (2013.01); *C07K 2317/33* (2013.01); *C07K 2317/56* (2013.01); *C07K 2317/565* (2013.01); *C07K 2317/76* (2013.01)

(58) Field of Classification Search
CPC .............. C07K 16/244; C07K 2317/24; C07K 2317/31; C07K 2317/33; C07K 2317/56; C07K 2317/565; C07K 2317/76; C07K 2317/524; C07K 2317/34; C07K 2317/71; C07K 2317/734; C07K 2317/92; C07K 2319/30; C07K 14/7155; A61K 39/3955; A61K 2039/505; C12N 15/63; A61P 37/00
See application file for complete search history.

(56) References Cited

U.S. PATENT DOCUMENTS

| | | | |
|---|---|---|---|
| 5,200,340 A * | 4/1993 | Foster | ............ C12Y 304/21069 |
| | | | 435/352 |
| 2008/0044423 A1 * | 2/2008 | Cochrane | ................ A61P 25/00 |
| | | | 435/69.6 |
| 2012/0251531 A1 | 10/2012 | Baehner et al. | |
| 2015/0025022 A1 | 1/2015 | Aharoni et al. | |

FOREIGN PATENT DOCUMENTS

| | | | |
|---|---|---|---|
| EP | 2481753 A1 | 8/2012 | |
| WO | 2013011368 A2 | 1/2013 | |
| WO | WO-2015120790 A1 * | 8/2015 | .............. A61P 31/18 |
| WO | 2016044189 A1 | 3/2016 | |
| WO | 2016154177 A2 | 9/2016 | |
| WO | 2017068472 A1 | 4/2017 | |

OTHER PUBLICATIONS

Colman PM. Res Immunol. Jan. 1994;145(1):33-6. (Year: 1994).*
Harris et al. Biotechnology, vol. 11, p. 1293-1297, 1993 (Year: 1993).*
Rudikoff et al. Proc. Natl. Acad. Sci. USA, 79(6):1979-1983, Mar. 1982 (Year: 1982).*
Paul. Fundamental Immunology, 3rd Edition, 1993, pp. 292-295 (Year: 1993).*
Bendig M. M. Methods: A Companion to Methods in Enzymology, 1995; 8:83-93 (Year: 1995).*
"IL-17A Monoclonal Antibody (eBio64DEC17), PE, eBioscience(TM)," Invitrogen Product Catalogue, 2011, 3 pages.
Bartlett et al., "Targeting the IL-17-TH17 Pathway," Nat Rev Drug Discov., 2015, 14(1):11-12.
Brummel et al., "Probing the Combining Site of an Anti-Carbohydrate Antibody by Saturation-Mutagenesis: Role of the Heavy-Chain CDR3 Residues," Biochemistry, 1993, 32:1180-1187.
Burks et al., "In vitro scanning saturation of mutagenesis of an antibody binding pocket," Proc. Natl. Acad. Sci., 1997, vol. 94, 412-417.
Casset et al., "A peptide mimetic of an anti-CD4 monoclonal antibody by rational design," Biochemical and Biophysical Research Communications, 2003, 307:198-205.

(Continued)

*Primary Examiner* — Sean E Aeder
*Assistant Examiner* — Yie Chia Lee
(74) *Attorney, Agent, or Firm* — McBee, Moore & Vanik IP, LLC

(57) ABSTRACT

Provided are various embodiments relating to anti-IL17A antibodies and IL17Ra ECD polypeptides that bind to IL17A. In various embodiments, such anti-IL17A antibodies or IL17Ra ECD polypeptides can be used in methods to treat IL17-induced conditions in subjects, such as humans or companion animals, such as canines, felines, and equines. Also provided are various embodiments relating to IgG Fc variant polypeptides having one or more amino acid substitutions for reducing binding to C1q and/or CD16. In some embodiments, the IgG Fc variants and/or polypeptides comprising the IgG Fc variants (e.g., fusion polypeptides comprising the IgG Fc variants and the anti-IL17A antibodies and/or IL17Ra ECD polypeptides described herein) may have reduced complement-mediated immune responses and/or antibody-dependent cell-mediated cytotoxicity.

16 Claims, 8 Drawing Sheets

Specification includes a Sequence Listing.

(56)        References Cited

OTHER PUBLICATIONS

Chaudhary et al., "Alterations in circulating concentrations of IL-17, IL-31 and total IgE in dogs with atopic dermatitis," Vet Dermatol., 2019, 30:383-e114.

Chenuet et al., "Neutralization of either IL-17A or IL-17F is sufficient to inhibit house dust mite induced allergic asthma in mice,"Clinical Science, 2017, 131:2533-2548.

Darch et al., "Secukinumab-Induced Inflammatory Bowel Disease in a Patient Treated for Chronic Plaque Psoriasis and Psoriatic Arthritis: A Case Report and Review of the Role of Novel Biologic Agents Targeting the p19 Subunit of L-23," Case Reports in Medicine, 2020, vol. 2020, 1-6.

Edwards et al., "The Remarkable Flexibility of the Human Antibody Repertoire; Isolation of Over One Thousand Different Antibodies to a Single Protein, BLyS," 2003, Journal of Molecular Biology, vol. 334, 103-118.

Ely et al., "Structural basis of receptor sharing by interleukin 17 cytokines," Nat Immunol., 2009, 10(12):1245-1251.

Extended European Search Report received in PCT/US2018/038033 dated Mar. 23, 2021, 10 pages.

Gerhardt et al., "Structure of IL-17A in Complex with a Potent, Fully Human Neutralizing Antibody," J Mol Biol., 2009, 394(5):905-921.

Goel et al., Plasticity within the Antigen-Combining Site May Manifest as Molecular Mimicry in the Humoral Immune Response, The Journal of Immunology, 2004, 173(12): 7358-7367.

Guttman-Yassky et al., "Low Expression of the IL-23/Th17 Pathway in Atopic Dermatitis Compared to Psoriasis," J Immunol., 2008, 181(10):7420-7427.

Havrdova et al., "Activity of secukinumab an anti-IL-17A antibody, on brain lesions in RRMS: results from a randomized, proof-of-concept study," Journal of Neurology, 2016, 263:1287-1295.

Hueber et al., "Secukinumab, a human anti-IL-17A monoclonal antibody, for moderate to severe Chron's disease: unexpected results of a randomized, double-blind placebo-controlled trial," Gut, 2012, vol. 61, 1693-1700.

International Search Report and Written Opinion in PCT/US2018/038033 dated Sep. 13, 2018, 16 pages.

Kinjo et al., "Intestinal IL-17 Expression in Canine Inflammatory Bowel Disease," International Journal of Veterinary Health Science & Research, 2017, 5(3):171-175.

Kol et al., "Th17 Pathway As a Target for Multipotent Stromal Cell Therapy in Dogs: Implications for Translational Research," Plos One, 2016, 11(2):1-14.

Liu et al., "IL-17A exacerbates neuroinflammation and neurodegeneration by activating microglia in rodent models of Parkinson's disease," Brain, Behavior, and Immunity, 2019, 81:630-645.

Liu et al., "Crystal Structures of Interleukin 17A and its Complex with IL-17 Receptor A," Nature Commun., 2013, 4:1888 doi: 10.1038/ncomms2880, 9 pages.

Lloyd et al., "Modelling the human immune response: performance of a 1011 human antibody repertoire against a broad panel of therapeutically relevant antigens," ProteinE Engineering, Design & Selection, 2009, 22(3):159-168.

Metawi et al., "Serum and synovial fluid levels of interleukin-17 in correlation with disease activity in patients with RA," Clinical Rheumatology, 2011, 30:1201-1207.

Moreira et al., "Cross-reactivity of commercially available anti-human monoclonal antibodies with canine cytokines: establishment of a reliable panel to detect functional profile or peripheral blood lymphocytes by intracytoplasmic staining," Acta Vet Scand., 2015, 57(51):1-12.

Pandit et al., "Mapping of discontinuous conformational epitopes by amide hydrogen/deuterium exchange mass spectrometry and computational docking," J. Mol. Recognit., 2012, 25:114-124.

Paul, "Fundamental Immunology," 3rd Edition, 1993, 292-295.

Thaci et al., "Secukinumab in psoriasis: randomized, controlled phase 3 trial results assessing the potential to improve treatment response in partial responders (Stature)," British Journal of Dermatology, 2015, vol. 173, 777-787.

Anonymous: "IL-17A Monoclonal Antibody (eBio64DEC17)", Invitrogen Product catalogue, Jan. 1, 2011 (Jan. 1, 2011), pp. 1-3, XP055784755, Retrieved from the Internet—Description provided.

Inbal Sela-Culang et al: "The Structural Basis of Antibody-Antigen Recognition", Frontiers in Immunology, vol. 4, Oct. 8, 2013 (Oct. 8, 2013), XP055557261.

* cited by examiner

Antibody [nM]

OD leader

```
C  MKFPSQLLLFLLFRITGIICDIQMTQSSSYLSVSLGGRVTITTCKANDHI-----NNWLAW   55
D  METDTLLLWVLLLWVPGSTGDIVLTQSPASLAVSLGQRATISYRASKSV-STSGYSYMHW   59
E  -MKLPVRLLVLMFWIPASNSDVVMTQTPLSLPVSLGDQASISCRSSQSLVHSNGNTYFHW   59
A  -MKLPVRLLVLMFWIPASSSDVVMTQTPLSLPVSLGDQASISCRSSQSLVHSNGNTYLHW   59
      * . .*::.. : ..:**:   *  ::*** **:: :: ::...  .:  :: *

C  YQQKPGNAPRLLISGSTSLETGVPSRFSGSGSGKDYTLSITSLQTEDVATYYCQQYWSTP  115
D  NQQKPGQPPRLLIYLVSNLESGVPARFSGSGSGTDFTLNIHPVEEEDAATYYCQHI-REL  118
E  YLQKPGQSPKLLIYKVSNRFSGVPDRFSGSGSGTDFTLKISRVEAEDLGVYFCSQSTHAP  119
A  YLQRPGQSPNLLIYKVSNRFSGVPDRFSGSGSGTDFTLKISRVEAEDLGVYFCSQSTHVP  119
    * .:**..*.****  :  . : .:*** ********.*  : * .: . ** .::*::..
```

C-terminal sequence

```
C  FTFGSGTKLEIKRADAAPTVSIFPPSSEQLTSGGASVVLGVIMVIAVSCVKLLSAHNST  174
D  YTFGGGTKLEIKRADAAPTVSI-------------------------------------  140
E  FTFGSGTKLEIKRADAAPTVSIFPPSSEQLTSGGASVVSRAN------------------  161
A  FTFGSGTKLEIKRADAAPTVSIFPPSSEQLTSGGASVVCKGEF------------------  162
    :.** ****************
```

C  SEQ ID NO: 100
D  SEQ ID NO: 103
E  SEQ ID NO: 101
A  SEQ ID NO: 102

*Fig. 2A*

```
      leader
D     -MGWIWIFLFLLSGTAGVHSEVQLQQSGPELVKTGASVKISCKASGYSFTYYYMHWVKQS   59
C     -MNLGLSFIFIALILKGVQCEVQLVESGGGLVQPGGSLKLSCAASGFTFSSYGMSWVRQT   59
E     MAVLGLL-LCLVTFPSCVLSQVQLKESGPGLVAPSQSLSITCTISGFSLTSNGVHWVRQP   59
A     MAVLGLL-LCLVTFPSCVLSQVQLKESGPGLVAPSQSLSITCTISGFSLTSNGVHWVRQS   59
             *   .    .: ****  :: .:*** **    * :: ::   ** **:.:*

D     HGKSLEWIGYISCFNGDTNYNQEFKDKATFTADTSSSTAYMQFNSLTSEDSAVYYCARGL  119
C     PDKRLELVAIINSNGGSTYYPDSVKGRFTISRDNDKNSLYLQMSSLKSEDTAMYYCVRC-  118
E     PGKGLEWLVVIWSDGTT-TYNSALKSRLSISKDNSKSQVFLKMNSLQTDDTAMYYCARHY  118
A     PGKDLEWLVVIWSDGTT-TYNSDFKSRLSISKDNSKSQVFLKMNSLQTDDTAMYYCARHY  118
      . *  **    *      :   .    .  ::::.. .::**    *.*:**:. .*

C-terminal sequence
D     STLITEGWFAYWGQGTLVTVSAAKTTPPSVYPLAPGSA---------------         157
C     HYD-YERVFDYWGQGTTLTVSSAKTTPPSVYPLAPGSAAQTNSMVTLGCLVKGYFPE     174
E     DRG-YYYAMDYWGQGTSVTVSSAKTTPPSVYPLAPGSAAQTNSMVTLGCLVKGEF--     172
A     DWG-YYYAMDYWGQGTSVTVSSAKTTPPSVYPLAPGSAAQTNSMVTLGCLVKGEF--     172
          .:  ****** :*****.:************************

D     SEQ ID NO: 104
C     SEQ ID NO: 105
E     SEQ ID NO: 107
A     SEQ ID NO: 106
```

*Fig. 2B*

SEQUENCE LISTING

<160> NUMBER OF SEQ ID NOS: 123

<210> SEQ ID NO 1
<211> LENGTH: 10
<212> TYPE: PRT
<213> ORGANISM: Artificial Sequence
<220> FEATURE:
<223> OTHER INFORMATION: Variable heavy chain CDR-H1 amino acid sequence
     of mouse antibody clone C

<400> SEQUENCE: 1

Gly Phe Thr Phe Ser Ser Tyr Gly Met Ser
1               5                   10

<210> SEQ ID NO 2
<211> LENGTH: 17

```
<212> TYPE: PRT
<213> ORGANISM: Artificial Sequence
<220> FEATURE:
<223> OTHER INFORMATION: Variable heavy chain CDR-H2 amino acid sequence
      of mouse antibody clone C

<400> SEQUENCE: 2

Ile Ile Asn Ser Asn Gly Gly Ser Thr Tyr Tyr Pro Asp Ser Val Lys
1               5                   10                  15

Gly

<210> SEQ ID NO 3
<211> LENGTH: 11
<212> TYPE: PRT
<213> ORGANISM: Artificial Sequence
<220> FEATURE:
<223> OTHER INFORMATION: Variable heavy chain CDR-H3 amino acid sequence
      of mouse antibody clone C

<400> SEQUENCE: 3

Cys His Tyr Asp Tyr Glu Arg Val Phe Asp Tyr
1               5                   10

<210> SEQ ID NO 4
<211> LENGTH: 25
<212> TYPE: PRT
<213> ORGANISM: Artificial Sequence
<220> FEATURE:
<223> OTHER INFORMATION: Variable region heavy chain framework HC-FR1
      amino acid sequence of mouse antibody clone C

<400> SEQUENCE: 4

Glu Val Gln Leu Val Glu Ser Gly Gly Gly Leu Val Gln Pro Gly Gly
1               5                   10                  15

Ser Leu Lys Leu Ser Cys Ala Ala Ser
            20                  25

<210> SEQ ID NO 5
<211> LENGTH: 14
<212> TYPE: PRT
<213> ORGANISM: Artificial Sequence
<220> FEATURE:
<223> OTHER INFORMATION: Variable region heavy chain framework HC-FR2
      amino acid sequence of mouse antibody clone C

<400> SEQUENCE: 5

Trp Val Arg Gln Thr Pro Asp Lys Arg Leu Glu Leu Val Ala
1               5                   10

<210> SEQ ID NO 6
<211> LENGTH: 32
<212> TYPE: PRT
<213> ORGANISM: Artificial Sequence
<220> FEATURE:
<223> OTHER INFORMATION: Variable region heavy chain framework HC-FR3
      amino acid sequence of mouse antibody clone C

<400> SEQUENCE: 6

Arg Phe Thr Ile Ser Arg Asp Asn Asp Lys Asn Ser Leu Tyr Leu Gln
1               5                   10                  15

Met Ser Ser Leu Lys Ser Glu Asp Thr Ala Met Tyr Tyr Cys Val Arg
            20                  25                  30

<210> SEQ ID NO 7
<211> LENGTH: 11
<212> TYPE: PRT
```

-continued

```
<213> ORGANISM: Artificial Sequence
<220> FEATURE:
<223> OTHER INFORMATION: Variable region heavy chain framework HC-FR4
      amino acid sequence of mouse antibody clone C

<400> SEQUENCE: 7

Trp Gly Gln Gly Thr Thr Leu Thr Val Ser Ser
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Variable light chain CDR-L1 amino acid sequence
      of mouse antibody clone C

<400> SEQUENCE: 8

Lys Ala Asn Asp His Ile Asn Asn Trp Leu Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Variable light chain CDR-L2 amino acid sequence
      of mouse antibody clone C

<400> SEQUENCE: 9

Gly Ser Thr Ser Leu Glu Thr
1               5

<210> SEQ ID NO 10
<211> LENGTH: 9
<212> TYPE: PRT
<213> ORGANISM: Artificial Sequence
<220> FEATURE:
<223> OTHER INFORMATION: Variable light chain CDR-L3 amino acid sequence
      of mouse antibody clone C

<400> SEQUENCE: 10

Gln Gln Tyr Trp Ser Thr Pro Phe Thr
1               5

<210> SEQ ID NO 11
<211> LENGTH: 23
<212> TYPE: PRT
<213> ORGANISM: Artificial Sequence
<220> FEATURE:
<223> OTHER INFORMATION: Variable region light chain framework LC-FR1
      amino acid sequence of mouse antibody clone C1

<400> SEQUENCE: 11

Asp Ile Gln Met Thr Gln Ser Ser Ser Tyr Leu Ser Val Ser Leu Gly
1               5                   10                  15

Gly Arg Val Thr Ile Thr Cys
            20

<210> SEQ ID NO 12
<211> LENGTH: 15
<212> TYPE: PRT
<213> ORGANISM: Artificial Sequence
<220> FEATURE:
<223> OTHER INFORMATION: Variable region light chain framework LC-FR2
      amino acid sequence of mouse antibody clone C

<400> SEQUENCE: 12
```

-continued

```
Trp Tyr Gln Gln Lys Pro Gly Asn Ala Pro Arg Leu Leu Ile Ser
1               5                   10                  15

<210> SEQ ID NO 13
<211> LENGTH: 32
<212> TYPE: PRT
<213> ORGANISM: Artificial Sequence
<220> FEATURE:
<223> OTHER INFORMATION: Variable region light chain framework LC-FR3
      amino acid sequence of mouse antibody clone C

<400> SEQUENCE: 13

Gly Val Pro Ser Arg Phe Ser Gly Ser Gly Ser Gly Lys Asp Tyr Thr
1               5                   10                  15

Leu Ser Ile Thr Ser Leu Gln Thr Glu Asp Val Ala Thr Tyr Tyr Cys
                20                  25                  30

<210> SEQ ID NO 14
<211> LENGTH: 10
<212> TYPE: PRT
<213> ORGANISM: Artificial Sequence
<220> FEATURE:
<223> OTHER INFORMATION: Variable region light chain framework LC-FR4
      amino acid sequence of mouse antibody clone C

<400> SEQUENCE: 14

Phe Gly Ser Gly Thr Lys Leu Glu Ile Lys
1               5                   10

<210> SEQ ID NO 15
<211> LENGTH: 120
<212> TYPE: PRT
<213> ORGANISM: Artificial Sequence
<220> FEATURE:
<223> OTHER INFORMATION: Caninized variable heavy chain amino acid
      sequence of mouse antibody clone C

<400> SEQUENCE: 15

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Gly Met Ser Trp Val Arg Gln Ala Pro Gly Lys Arg Leu Glu Leu Val
        35                  40                  45

Ala Ile Ile Asn Ser Asn Gly Gly Ser Thr Tyr Tyr Pro Asp Ser Val
    50                  55                  60

Lys Gly Arg Phe Thr Phe Ser Leu Asp Thr Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Val Arg Cys His Tyr Asp Tyr Glu Arg Val Phe Asp Tyr Trp Gly Gln
            100                 105                 110

Gly Thr Leu Val Thr Val Ser Ser
        115                 120

<210> SEQ ID NO 16
<211> LENGTH: 107
<212> TYPE: PRT
<213> ORGANISM: Artificial Sequence
<220> FEATURE:
<223> OTHER INFORMATION: Caninized variable light chain amino acid
      sequence of mouse antibody clone C
```

-continued

```
<400> SEQUENCE: 16

Asp Ile Gln Met Thr Gln Ser Pro Ala Ser Val Ser Gly Ser Leu Gly
1               5                   10                  15

Asp Lys Val Ser Ile Thr Cys Lys Ala Asn Asp His Ile Asn Asn Trp
            20                  25                  30

Leu Ala Trp Tyr Gln Gln Leu Pro Gly Asn Ala Pro Arg Leu Leu Ile
        35                  40                  45

Ser Gly Ser Thr Ser Leu Glu Ser Gly Val Pro Asp Arg Phe Ser Gly
    50                  55                  60

Ser Lys Ser Gly Ser Ser Phe Thr Leu Thr Ile Ser Gly Leu Gln Pro
65                  70                  75                  80

Glu Asp Phe Ala Thr Tyr Tyr Cys Gln Gln Tyr Trp Ser Thr Pro Phe
                85                  90                  95

Thr Phe Gly Ser Gly Thr Lys Val Glu Ile Lys
            100                 105

<210> SEQ ID NO 17
<211> LENGTH: 450
<212> TYPE: PRT
<213> ORGANISM: Artificial Sequence
<220> FEATURE:
<223> OTHER INFORMATION: Caninized heavy chain sequence from mouse
      antibody clone C and canine IgG-A

<400> SEQUENCE: 17

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Arg Leu Glu Leu Val
        35                  40                  45

Ala Ile Ile Asn Ser Asn Gly Gly Ser Thr Tyr Tyr Pro Asp Ser Val
    50                  55                  60

Lys Gly Arg Phe Thr Phe Ser Leu Asp Thr Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Val Arg Cys His Tyr Asp Tyr Glu Arg Val Phe Asp Tyr Trp Gly Gln
            100                 105                 110

Gly Thr Leu Val Thr Val Ser Ser Ala Ser Thr Thr Ala Pro Ser Val
        115                 120                 125

Phe Pro Leu Ala Pro Ser Cys Gly Ser Thr Ser Gly Ser Thr Val Ala
    130                 135                 140

Leu Ala Cys Leu Val Ser Gly Tyr Phe Pro Glu Pro Val Thr Val Ser
145                 150                 155                 160

Trp Asn Ser Gly Ser Leu Thr Ser Gly Val His Thr Phe Pro Ser Val
            165                 170                 175

Leu Gln Ser Ser Gly Leu His Ser Leu Ser Ser Met Val Thr Val Pro
            180                 185                 190

Ser Ser Arg Trp Pro Ser Glu Thr Phe Thr Cys Asn Val Val His Pro
            195                 200                 205

Ala Ser Asn Thr Lys Val Asp Lys Pro Val Phe Asn Glu Cys Arg Cys
    210                 215                 220

Thr Asp Thr Pro Cys Pro Val Pro Glu Pro Leu Gly Gly Pro Ser Val
225                 230                 235                 240
```

```
Leu Ile Phe Pro Pro Lys Pro Lys Asp Ile Leu Arg Ile Thr Arg Thr
            245         250             255

Pro Glu Val Thr Cys Val Val Leu Asp Leu Gly Arg Glu Asp Pro Glu
            260         265             270

Val Gln Ile Ser Trp Phe Val Asp Gly Lys Glu Val His Thr Ala Lys
            275         280             285

Thr Gln Ser Arg Glu Gln Gln Phe Asn Gly Thr Tyr Arg Val Val Ser
    290         295             300

Val Leu Pro Ile Glu His Gln Asp Trp Leu Thr Gly Lys Glu Phe Lys
305             310             315             320

Cys Arg Val Asn His Ile Asp Leu Pro Ser Pro Ile Glu Arg Thr Ile
            325         330             335

Ser Lys Ala Arg Gly Arg Ala His Lys Pro Ser Val Tyr Val Leu Pro
            340         345             350

Pro Ser Pro Lys Glu Leu Ser Ser Ser Asp Thr Val Ser Ile Thr Cys
            355         360             365

Leu Ile Lys Asp Phe Tyr Pro Pro Asp Ile Asp Val Glu Trp Gln Ser
    370         375             380

Asn Gly Gln Gln Glu Pro Glu Arg Lys His Arg Met Thr Pro Pro Gln
385             390             395             400

Leu Asp Glu Asp Gly Ser Tyr Phe Leu Tyr Ser Lys Leu Ser Val Asp
            405         410             415

Lys Ser Arg Trp Gln Gln Gly Asp Pro Phe Thr Cys Ala Val Met His
            420         425             430

Glu Thr Leu Gln Asn His Tyr Thr Asp Leu Ser Leu Ser His Ser Pro
            435         440             445

Gly Lys
    450
```

<210> SEQ ID NO 18
<211> LENGTH: 455
<212> TYPE: PRT
<213> ORGANISM: Artificial Sequence
<220> FEATURE:
<223> OTHER INFORMATION: Caninized heavy chain sequence from mouse
     antibody clone C and canine IgG-B

<400> SEQUENCE: 18

```
Glu Val Gln Leu Val Glu Ser Gly Gly Gly Leu Val Lys Pro Gly Gly
1           5               10              15

Ser Leu Arg Leu Ser Cys Ala Ala Ser Gly Phe Thr Phe Ser Ser Tyr
            20          25              30

Gly Met Ser Trp Val Arg Gln Ala Pro Gly Lys Arg Leu Glu Leu Val
            35          40              45

Ala Ile Ile Asn Ser Asn Gly Gly Ser Thr Tyr Tyr Pro Asp Ser Val
    50          55              60

Lys Gly Arg Phe Thr Phe Ser Leu Asp Thr Ser Lys Asn Thr Leu Tyr
65          70              75              80

Leu Gln Met Asn Ser Leu Arg Ala Glu Asp Thr Ala Met Tyr Tyr Cys
            85          90              95

Val Arg Cys His Tyr Asp Tyr Glu Arg Val Phe Asp Tyr Trp Gly Gln
            100         105             110

Gly Thr Leu Val Thr Val Ser Ser Ala Ser Thr Thr Ala Pro Ser Val
            115         120             125

Phe Pro Leu Ala Pro Ser Cys Gly Ser Thr Ser Gly Ser Thr Val Ala
    130         135             140
```

-continued

```
Leu Ala Cys Leu Val Ser Gly Tyr Phe Pro Glu Pro Val Thr Val Ser
145                 150                 155                 160

Trp Asn Ser Gly Ser Leu Thr Ser Gly Val His Thr Phe Pro Ser Val
                165                 170                 175

Leu Gln Ser Ser Gly Leu Tyr Ser Leu Ser Ser Met Val Thr Val Pro
                180                 185                 190

Ser Ser Arg Trp Pro Ser Glu Thr Phe Thr Cys Asn Val Ala His Pro
            195                 200                 205

Ala Ser Lys Thr Lys Val Asp Lys Pro Val Pro Lys Arg Glu Asn Gly
        210                 215                 220

Arg Val Pro Arg Pro Pro Asp Cys Pro Lys Cys Pro Ala Pro Glu Met
225                 230                 235                 240

Leu Gly Gly Pro Ser Val Phe Ile Phe Pro Pro Lys Pro Lys Asp Thr
                245                 250                 255

Leu Leu Ile Ala Arg Thr Pro Glu Val Thr Cys Val Val Val Asp Leu
                260                 265                 270

Asp Pro Glu Asp Pro Glu Val Gln Ile Ser Trp Phe Val Asp Gly Lys
            275                 280                 285

Gln Met Gln Thr Ala Lys Thr Gln Pro Arg Glu Glu Gln Phe Asn Gly
        290                 295                 300

Thr Tyr Arg Val Val Ser Val Leu Pro Ile Gly His Gln Asp Trp Leu
305                 310                 315                 320

Lys Gly Lys Gln Phe Thr Cys Lys Val Asn Asn Lys Ala Leu Pro Ser
                325                 330                 335

Pro Ile Glu Arg Thr Ile Ser Lys Ala Arg Gly Gln Ala His Gln Pro
                340                 345                 350

Ser Val Tyr Val Leu Pro Pro Ser Arg Glu Glu Leu Ser Lys Asn Thr
            355                 360                 365

Val Ser Leu Thr Cys Leu Ile Lys Asp Phe Phe Pro Pro Asp Ile Asp
        370                 375                 380

Val Glu Trp Gln Ser Asn Gly Gln Gln Glu Pro Glu Ser Lys Tyr Arg
385                 390                 395                 400

Thr Thr Pro Pro Gln Leu Asp Glu Asp Gly Ser Tyr Phe Leu Tyr Ser
                405                 410                 415

Lys Leu Ser Val Asp Lys Ser Arg Trp Gln Arg Gly Asp Thr Phe Ile
            420                 425                 430

Cys Ala Val Met His Glu Ala Leu His Asn His Tyr Thr Gln Glu Ser
        435                 440                 445

Leu Ser His Ser Pro Gly Lys
    450                 455
```

```
<210> SEQ ID NO 19
<211> LENGTH: 453
<212> TYPE: PRT
<213> ORGANISM: Artificial Sequence
<220> FEATURE:
<223> OTHER INFORMATION: Caninized heavy chain sequence from mouse
      antibody clone C and canine IgG-C

<400> SEQUENCE: 19
```

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Gly Met Ser Trp Val Arg Gln Ala Pro Gly Lys Arg Leu Glu Leu Val
```

-continued

```
               35                      40                      45
Ala Ile Ile Asn Ser Asn Gly Gly Ser Thr Tyr Tyr Pro Asp Ser Val
           50                      55                      60
Lys Gly Arg Phe Thr Phe Ser Leu Asp Thr Ser Lys Asn Thr Leu Tyr
65                      70                      75                      80
Leu Gln Met Asn Ser Leu Arg Ala Glu Asp Thr Ala Met Tyr Tyr Cys
                   85                      90                      95
Val Arg Cys His Tyr Asp Tyr Glu Arg Val Phe Asp Tyr Trp Gly Gln
               100                     105                     110
Gly Thr Leu Val Thr Val Ser Ser Ala Ser Thr Thr Ala Pro Ser Val
               115                     120                     125
Phe Pro Leu Ala Pro Ser Cys Gly Ser Gln Ser Gly Ser Thr Val Ala
       130                     135                     140
Leu Ala Cys Leu Val Ser Gly Tyr Ile Pro Glu Pro Val Thr Val Ser
145                     150                     155                     160
Trp Asn Ser Val Ser Leu Thr Ser Gly Val His Thr Phe Pro Ser Val
                   165                     170                     175
Leu Gln Ser Ser Gly Leu Tyr Ser Leu Ser Ser Met Val Thr Val Pro
               180                     185                     190
Ser Ser Arg Trp Pro Ser Glu Thr Phe Thr Cys Asn Val Ala His Pro
               195                     200                     205
Ala Thr Asn Thr Lys Val Asp Lys Pro Val Ala Lys Glu Cys Glu Cys
       210                     215                     220
Lys Cys Asn Cys Asn Asn Cys Pro Cys Pro Gly Cys Gly Leu Leu Gly
225                     230                     235                     240
Gly Pro Ser Val Phe Ile Phe Pro Pro Lys Pro Lys Asp Ile Leu Val
                   245                     250                     255
Thr Ala Arg Thr Pro Thr Val Thr Cys Val Val Val Asp Leu Asp Pro
               260                     265                     270
Glu Asn Pro Glu Val Gln Ile Ser Trp Phe Val Asp Ser Lys Gln Val
               275                     280                     285
Gln Thr Ala Asn Thr Gln Pro Arg Glu Glu Gln Ser Asn Gly Thr Tyr
       290                     295                     300
Arg Val Val Ser Val Leu Pro Ile Gly His Gln Asp Trp Leu Ser Gly
305                     310                     315                     320
Lys Gln Phe Lys Cys Lys Val Asn Asn Lys Ala Leu Pro Ser Pro Ile
                   325                     330                     335
Glu Glu Ile Ile Ser Lys Thr Pro Gly Gln Ala His Gln Pro Asn Val
                   340                     345                     350
Tyr Val Leu Pro Pro Ser Arg Asp Glu Met Ser Lys Asn Thr Val Thr
               355                     360                     365
Leu Thr Cys Leu Val Lys Asp Phe Phe Pro Pro Glu Ile Asp Val Glu
       370                     375                     380
Trp Gln Ser Asn Gly Gln Gln Glu Pro Glu Ser Lys Tyr Arg Met Thr
385                     390                     395                     400
Pro Pro Gln Leu Asp Glu Asp Gly Ser Tyr Phe Leu Tyr Ser Lys Leu
                   405                     410                     415
Ser Val Asp Lys Ser Arg Trp Gln Arg Gly Asp Thr Phe Ile Cys Ala
               420                     425                     430
Val Met His Glu Ala Leu His Asn His Tyr Thr Gln Ile Ser Leu Ser
           435                     440                     445
His Ser Pro Gly Lys
       450
```

```
<210> SEQ ID NO 20
<211> LENGTH: 451
<212> TYPE: PRT
<213> ORGANISM: Artificial Sequence
<220> FEATURE:
<223> OTHER INFORMATION: Caninized heavy chain sequence from mouse
     antibody clone Clone C and canine IgG-D

<400> SEQUENCE: 20

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Arg Leu Glu Leu Val
        35                  40                  45

Ala Ile Ile Asn Ser Asn Gly Gly Ser Thr Tyr Tyr Pro Asp Ser Val
    50                  55                  60

Lys Gly Arg Phe Thr Phe Ser Leu Asp Thr Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Val Arg Cys His Tyr Asp Tyr Glu Arg Val Phe Asp Tyr Trp Gly Gln
            100                 105                 110

Gly Thr Leu Val Thr Val Ser Ser Ala Ser Thr Thr Ala Pro Ser Val
            115                 120                 125

Phe Pro Leu Ala Pro Ser Cys Gly Ser Thr Ser Gly Ser Thr Val Ala
    130                 135                 140

Leu Ala Cys Leu Val Ser Gly Tyr Phe Pro Glu Pro Val Thr Val Ser
145                 150                 155                 160

Trp Asn Ser Gly Ser Leu Thr Ser Gly Val His Thr Phe Pro Ser Val
                165                 170                 175

Leu Gln Ser Ser Gly Leu Tyr Ser Leu Ser Ser Thr Val Thr Val Pro
            180                 185                 190

Ser Ser Arg Trp Pro Ser Glu Thr Phe Thr Cys Asn Val Val His Pro
            195                 200                 205

Ala Ser Asn Thr Lys Val Asp Lys Pro Val Pro Lys Glu Ser Thr Cys
    210                 215                 220

Lys Cys Ile Ser Pro Cys Pro Val Pro Glu Ser Leu Gly Gly Pro Ser
225                 230                 235                 240

Val Phe Ile Phe Pro Pro Lys Pro Lys Asp Ile Leu Arg Ile Thr Arg
                245                 250                 255

Thr Pro Glu Ile Thr Cys Val Val Leu Asp Leu Gly Arg Glu Asp Pro
            260                 265                 270

Glu Val Gln Ile Ser Trp Phe Val Asp Gly Lys Glu Val His Thr Ala
            275                 280                 285

Lys Thr Gln Pro Arg Glu Gln Gln Phe Asn Ser Thr Tyr Arg Val Val
    290                 295                 300

Ser Val Leu Pro Ile Glu His Gln Asp Trp Leu Thr Gly Lys Glu Phe
305                 310                 315                 320

Lys Cys Arg Val Asn His Ile Gly Leu Pro Ser Pro Ile Glu Arg Thr
                325                 330                 335

Ile Ser Lys Ala Arg Gly Gln Ala His Gln Pro Ser Val Tyr Val Leu
            340                 345                 350

Pro Pro Ser Pro Lys Glu Leu Ser Ser Ser Asp Thr Val Thr Leu Thr
```

-continued

```
           355                   360                   365

Cys Leu Ile Lys Asp Phe Phe Pro Pro Glu Ile Asp Val Glu Trp Gln
    370                   375                   380

Ser Asn Gly Gln Pro Glu Pro Glu Ser Lys Tyr His Thr Thr Ala Pro
385                   390                   395                   400

Gln Leu Asp Glu Asp Gly Ser Tyr Phe Leu Tyr Ser Lys Leu Ser Val
                  405                   410                   415

Asp Lys Ser Arg Trp Gln Gln Gly Asp Thr Phe Thr Cys Ala Val Met
                  420                   425                   430

His Glu Ala Leu Gln Asn His Tyr Thr Asp Leu Ser Leu Ser His Ser
              435                   440                   445

Pro Gly Lys
    450

<210> SEQ ID NO 21
<211> LENGTH: 217
<212> TYPE: PRT
<213> ORGANISM: Artificial Sequence
<220> FEATURE:
<223> OTHER INFORMATION: Caninized light chain sequence from mouse
      antibody clone C and canine light chain constant region

<400> SEQUENCE: 21

Asp Ile Gln Met Thr Gln Ser Pro Ala Ser Val Ser Gly Ser Leu Gly
1               5                   10                  15

Asp Lys Val Ser Ile Thr Cys Lys Ala Asn Asp His Ile Asn Asn Trp
                20                  25                  30

Leu Ala Trp Tyr Gln Gln Leu Pro Gly Asn Ala Pro Arg Leu Leu Ile
            35                  40                  45

Ser Gly Ser Thr Ser Leu Glu Ser Gly Val Pro Asp Arg Phe Ser Gly
    50                  55                  60

Ser Lys Ser Gly Ser Ser Phe Thr Leu Thr Ile Ser Gly Leu Gln Pro
65                  70                  75                  80

Glu Asp Phe Ala Thr Tyr Tyr Cys Gln Gln Tyr Trp Ser Thr Pro Phe
                85                  90                  95

Thr Phe Gly Ser Gly Thr Lys Val Glu Ile Lys Arg Asn Asp Ala Gln
            100                 105                 110

Pro Ala Val Tyr Leu Phe Gln Pro Ser Pro Asp Gln Leu His Thr Gly
            115                 120                 125

Ser Ala Ser Val Val Cys Leu Leu Asn Ser Phe Tyr Pro Lys Asp Ile
    130                 135                 140

Asn Val Lys Trp Lys Val Asp Gly Val Ile Gln Asp Thr Gly Ile Gln
145                 150                 155                 160

Glu Ser Val Thr Glu Gln Asp Lys Asp Ser Thr Tyr Ser Leu Ser Ser
                165                 170                 175

Thr Leu Thr Met Ser Ser Thr Glu Tyr Leu Ser His Glu Leu Tyr Ser
            180                 185                 190

Cys Glu Ile Thr His Lys Ser Leu Pro Ser Thr Leu Ile Lys Ser Phe
            195                 200                 205

Gln Arg Ser Glu Cys Gln Arg Val Asp
    210                 215

<210> SEQ ID NO 22
<211> LENGTH: 131
<212> TYPE: PRT
<213> ORGANISM: Unknown
<220> FEATURE:
```

-continued

<223> OTHER INFORMATION: Mature canine IL17A amino acid sequence

<400> SEQUENCE: 22

Ala Gly Ile Ala Phe Pro Gln Asn Pro Gly Cys Arg Asn Thr Glu Asp
1               5                   10                  15

Lys Asn Phe Pro Gln His Val Lys Val Asn Leu Asn Ile Leu Asn Arg
            20                  25                  30

Asn Thr Asn Ser Arg Arg Pro Ser Asp Tyr Tyr Asn Arg Ser Thr Ser
        35                  40                  45

Pro Trp Asn Leu His Arg Asn Glu Asp Pro Glu Arg Tyr Pro Ser Val
    50                  55                  60

Ile Trp Glu Ala Lys Cys Arg His Leu Gly Cys Val Asn Asn Glu Gly
65                  70                  75                  80

Asn Ile Asn Tyr His Met Asn Ser Val Pro Ile Gln Gln Glu Ile Leu
                85                  90                  95

Val Leu Arg Arg Glu Ser Gln His Cys Pro His Ser Phe Arg Leu Glu
            100                 105                 110

Lys Met Leu Val Ala Val Gly Cys Thr Cys Val Thr Pro Ile Val Arg
            115                 120                 125

His Val Ala
    130

<210> SEQ ID NO 23
<211> LENGTH: 12
<212> TYPE: PRT
<213> ORGANISM: Unknown
<220> FEATURE:
<223> OTHER INFORMATION: Canine IL17A epitope, minimal sequence

<400> SEQUENCE: 23

Arg His Leu Gly Cys Val Asn Asn Glu Gly Asn Ile
1               5                   10

<210> SEQ ID NO 24
<211> LENGTH: 107
<212> TYPE: PRT
<213> ORGANISM: Artificial Sequence
<220> FEATURE:
<223> OTHER INFORMATION: Variable light chain amino acid sequence of
      mouse antibody clone C

<400> SEQUENCE: 24

Asp Ile Gln Met Thr Gln Ser Ser Ser Tyr Leu Ser Val Ser Leu Gly
1               5                   10                  15

Gly Arg Val Thr Ile Thr Cys Lys Ala Asn Asp His Ile Asn Asn Trp
            20                  25                  30

Leu Ala Trp Tyr Gln Gln Lys Pro Gly Asn Ala Pro Arg Leu Leu Ile
        35                  40                  45

Ser Gly Ser Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Phe
                85                  90                  95

Thr Phe Gly Ser Gly Thr Lys Leu Glu Ile Lys
            100                 105

<210> SEQ ID NO 25
<211> LENGTH: 120

-continued

```
<212> TYPE: PRT
<213> ORGANISM: Artificial Sequence
<220> FEATURE:
<223> OTHER INFORMATION: Variable heavy chain amino acid sequence of
      mouse antibody clone C

<400> SEQUENCE: 25

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Leu Val
        35                  40                  45

Ala Ile Ile Asn Ser Asn Gly Gly Ser Thr Tyr Tyr Pro Asp Ser Val
    50                  55                  60

Lys Gly Arg Phe Thr Ile Ser Arg Asp Asn Asp Lys Asn Ser Leu Tyr
65                  70                  75                  80

Leu Gln Met Ser Ser Leu Lys Ser Glu Asp Thr Ala Met Tyr Tyr Cys
                85                  90                  95

Val Arg Cys His Tyr Asp Tyr Glu Arg Val Phe Asp Tyr Trp Gly Gln
                100                 105                 110

Gly Thr Thr Leu Thr Val Ser Ser
        115                 120

<210> SEQ ID NO 26
<211> LENGTH: 217
<212> TYPE: PRT
<213> ORGANISM: Artificial Sequence
<220> FEATURE:
<223> OTHER INFORMATION: Chimeric variable light chain of mouse antibody
      clone C and canine light chain constant region

<400> SEQUENCE: 26

Asp Ile Gln Met Thr Gln Ser Ser Ser Tyr Leu Ser Val Ser Leu Gly
1               5                   10                  15

Gly Arg Val Thr Ile Thr Cys Lys Ala Asn Asp His Ile Asn Asn Trp
            20                  25                  30

Leu Ala Trp Tyr Gln Gln Lys Pro Gly Asn Ala Pro Arg Leu Leu Ile
        35                  40                  45

Ser Gly Ser Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Phe
                85                  90                  95

Thr Phe Gly Ser Gly Thr Lys Leu Glu Ile Lys Arg Asn Asp Ala Gln
                100                 105                 110

Pro Ala Val Tyr Leu Phe Gln Pro Ser Pro Asp Gln Leu His Thr Gly
        115                 120                 125

Ser Ala Ser Val Val Cys Leu Leu Asn Ser Phe Tyr Pro Lys Asp Ile
    130                 135                 140

Asn Val Lys Trp Lys Val Asp Gly Val Ile Gln Asp Thr Gly Ile Gln
145                 150                 155                 160

Glu Ser Val Thr Glu Gln Asp Lys Asp Ser Thr Tyr Ser Leu Ser Ser
                165                 170                 175

Thr Leu Thr Met Ser Ser Thr Glu Tyr Leu Ser His Glu Leu Tyr Ser
                180                 185                 190
```

-continued

```
Cys Glu Ile Thr His Lys Ser Leu Pro Ser Thr Leu Ile Lys Ser Phe
        195                 200                 205

Gln Arg Ser Glu Cys Gln Arg Val Asp
    210                 215

<210> SEQ ID NO 27
<211> LENGTH: 455
<212> TYPE: PRT
<213> ORGANISM: Artificial Sequence
<220> FEATURE:
<223> OTHER INFORMATION: Chimeric variable heavy chain of mouse antibody
      clone C and canine IgG-B

<400> SEQUENCE: 27

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Leu Val
            35                  40                  45

Ala Ile Ile Asn Ser Asn Gly Gly Ser Thr Tyr Tyr Pro Asp Ser Val
        50                  55                  60

Lys Gly Arg Phe Thr Ile Ser Arg Asp Asn Asp Lys Asn Ser Leu Tyr
65                  70                  75                  80

Leu Gln Met Ser Ser Leu Lys Ser Glu Asp Thr Ala Met Tyr Tyr Cys
                85                  90                  95

Val Arg Cys His Tyr Asp Tyr Glu Arg Val Phe Asp Tyr Trp Gly Gln
            100                 105                 110

Gly Thr Thr Leu Thr Val Ser Ser Ala Ser Thr Thr Ala Pro Ser Val
            115                 120                 125

Phe Pro Leu Ala Pro Ser Cys Gly Ser Thr Ser Gly Ser Thr Val Ala
    130                 135                 140

Leu Ala Cys Leu Val Ser Gly Tyr Phe Pro Glu Pro Val Thr Val Ser
145                 150                 155                 160

Trp Asn Ser Gly Ser Leu Thr Ser Gly Val His Thr Phe Pro Ser Val
                165                 170                 175

Leu Gln Ser Ser Gly Leu Tyr Ser Leu Ser Ser Met Val Thr Val Pro
                180                 185                 190

Ser Ser Arg Trp Pro Ser Glu Thr Phe Thr Cys Asn Val Ala His Pro
            195                 200                 205

Ala Ser Lys Thr Lys Val Asp Lys Pro Val Pro Lys Arg Glu Asn Gly
    210                 215                 220

Arg Val Pro Arg Pro Pro Asp Cys Pro Lys Cys Pro Ala Pro Glu Met
225                 230                 235                 240

Leu Gly Gly Pro Ser Val Phe Ile Phe Pro Pro Lys Pro Lys Asp Thr
                245                 250                 255

Leu Leu Ile Ala Arg Thr Pro Glu Val Thr Cys Val Val Val Asp Leu
                260                 265                 270

Asp Pro Glu Asp Pro Glu Val Gln Ile Ser Trp Phe Val Asp Gly Lys
            275                 280                 285

Gln Met Gln Thr Ala Lys Thr Gln Pro Arg Glu Glu Gln Phe Asn Gly
    290                 295                 300

Thr Tyr Arg Val Val Ser Val Leu Pro Ile Gly His Gln Asp Trp Leu
305                 310                 315                 320

Lys Gly Lys Gln Phe Thr Cys Lys Val Asn Asn Lys Ala Leu Pro Ser
                325                 330                 335
```

-continued

```
Pro Ile Glu Arg Thr Ile Ser Lys Ala Arg Gly Gln Ala His Gln Pro
        340                 345             350

Ser Val Tyr Val Leu Pro Pro Ser Arg Glu Glu Leu Ser Lys Asn Thr
        355             360             365

Val Ser Leu Thr Cys Leu Ile Lys Asp Phe Phe Pro Pro Asp Ile Asp
        370             375             380

Val Glu Trp Gln Ser Asn Gly Gln Gln Glu Pro Glu Ser Lys Tyr Arg
385                 390             395                 400

Thr Thr Pro Pro Gln Leu Asp Glu Asp Gly Ser Tyr Phe Leu Tyr Ser
            405             410             415

Lys Leu Ser Val Asp Lys Ser Arg Trp Gln Arg Gly Asp Thr Phe Ile
        420             425             430

Cys Ala Val Met His Glu Ala Leu His Asn His Tyr Thr Gln Glu Ser
        435             440             445

Leu Ser His Ser Pro Gly Lys
    450             455
```

```
<210> SEQ ID NO 28
<211> LENGTH: 155
<212> TYPE: PRT
<213> ORGANISM: Unknown
<220> FEATURE:
<223> OTHER INFORMATION: Canine IL17A precursor amino acid sequence

<400> SEQUENCE: 28

Met Thr Leu Val Thr Thr Ser Ser Met Phe Gln Ser Leu Leu Leu Leu
1               5               10              15

Leu Ser Leu Val Ala Ile Ile Lys Ala Gly Ile Ala Phe Pro Gln Asn
        20              25              30

Pro Gly Cys Arg Asn Thr Glu Asp Lys Asn Phe Pro Gln His Val Lys
        35              40              45

Val Asn Leu Asn Ile Leu Asn Arg Asn Thr Asn Ser Arg Arg Pro Ser
        50              55              60

Asp Tyr Tyr Asn Arg Ser Thr Ser Pro Trp Asn Leu His Arg Asn Glu
65              70              75              80

Asp Pro Glu Arg Tyr Pro Ser Val Ile Trp Glu Ala Lys Cys Arg His
            85              90              95

Leu Gly Cys Val Asn Asn Glu Gly Asn Ile Asn Tyr His Met Asn Ser
        100             105             110

Val Pro Ile Gln Gln Glu Ile Leu Val Leu Arg Arg Glu Ser Gln His
        115             120             125

Cys Pro His Ser Phe Arg Leu Glu Lys Met Leu Val Ala Val Gly Cys
        130             135             140

Thr Cys Val Thr Pro Ile Val Arg His Val Ala
145             150             155
```

```
<210> SEQ ID NO 29
<211> LENGTH: 153
<212> TYPE: PRT
<213> ORGANISM: Equus caballus

<400> SEQUENCE: 29

Met Ala Pro Leu Arg Thr Ser Ser Val Ser Leu Leu Leu Leu Leu Ser
1               5               10              15

Leu Val Ala Ile Val Lys Ala Gly Ile Val Ile Pro Gln Asn Pro Glu
        20              25              30
```

-continued

```
Cys Pro Asn Thr Gly Asp Lys Asn Phe Pro Gln Asn Val Lys Ile Asn
        35              40              45

Leu Asn Val Leu Asn Arg Lys Thr Asn Ser Arg Arg Ala Ser Asp Tyr
    50              55              60

His Asn Arg Ser Thr Ser Pro Trp Asn Leu His Arg Asn Glu Asp Pro
65              70              75              80

Glu Arg Tyr Pro Ser Val Ile Trp Glu Ala Lys Cys Arg His Leu Gly
                85              90              95

Cys Val Asn Ala Glu Gly Lys Val Asp Phe His Met Asn Ser Val Pro
            100             105             110

Ile Gln Gln Glu Ile Leu Val Leu Arg Arg Glu Ser Gln Asn Cys Pro
        115             120             125

His Ser Phe Gln Leu Glu Lys Met Leu Val Ala Val Gly Cys Thr Cys
    130             135             140

Val Thr Pro Ile Val Arg His Met Gly
145             150

<210> SEQ ID NO 30
<211> LENGTH: 155
<212> TYPE: PRT
<213> ORGANISM: Felus catus

<400> SEQUENCE: 30

Met Ala Pro Gly Thr Thr Ser Ser Met Phe Pro Ser Leu Leu Leu Leu
1               5               10              15

Leu Cys Leu Met Ala Ile Val Arg Thr Gly Ile Ala Phe Pro Gln Asn
            20              25              30

Pro Gly Cys Pro Thr Thr Glu Asp Lys Asn Phe Pro Gln His Val Lys
        35              40              45

Val Asn Val Asn Ile Leu Asn Gly Asn Lys Ser Ser Arg Arg Pro Leu
    50              55              60

Asp Tyr Tyr Arg Arg Ser Thr Ser Pro Trp Ser Leu His Arg Asn Glu
65              70              75              80

Asp Pro Glu Arg Tyr Pro Ser Val Ile Trp Glu Ala Lys Cys Leu His
                85              90              95

Trp Gly Cys Val Asn Thr Glu Gly Lys Glu Asp His His Met Asn Ser
            100             105             110

Val Pro Ile Gln Gln Glu Ile Leu Val Leu Arg Arg Glu Ser Arg His
        115             120             125

Cys Pro His Ser Phe Arg Leu Glu Lys Met Leu Val Thr Val Gly Cys
    130             135             140

Thr Cys Val Thr Pro Ile Val Arg His Val Val
145             150             155

<210> SEQ ID NO 31
<211> LENGTH: 157
<212> TYPE: PRT
<213> ORGANISM: Unknown
<220> FEATURE:
<223> OTHER INFORMATION: Canine IL17F precursor amino acid sequence

<400> SEQUENCE: 31

Met Ala Ile Leu Arg Asn Ile Ala Met Val Lys Ser Leu Leu Leu Leu
1               5               10              15

Val Leu Gly Leu Thr Leu Leu Ser Glu Val Ala Ala Arg Lys His Leu
            20              25              30

Lys Ala Gly Glu Thr Ala Leu Cys Pro Pro Leu Glu Asp Asn Ser Val
```

```
          35                  40                  45

Arg Val Asp Ile Arg Ile Leu Arg Gln Asn Arg Gly Ile Ser Ile Ser
     50                  55                  60

Asn Asp Phe Gln Asn Arg Ser Ser Ser Pro Trp Asp Tyr Asn Ile Thr
65                  70                  75                  80

Arg Asp Pro His Arg Phe Pro Ser Glu Ile Ala Glu Ala Gln Cys Arg
                85                  90                  95

His Ser Gly Cys Ile Asn Ala Glu Gly Gln Glu Asp Ser Ser Met Asn
               100                 105                 110

Ser Val Pro Ile Gln Gln Glu Phe Leu Val Leu Arg Arg Glu Pro Gln
               115                 120                 125

Gly Cys Ser Arg Ser Phe Arg Leu Glu Lys Val Leu Val Thr Val Gly
          130                 135                 140

Cys Thr Cys Val Thr Pro Ile Val Arg Tyr Val Arg Ala
145                 150                 155

<210> SEQ ID NO 32
<211> LENGTH: 822
<212> TYPE: PRT
<213> ORGANISM: Unknown
<220> FEATURE:
<223> OTHER INFORMATION: Canine IL17A receptor (IL17Ra) amino acid
      sequence

<400> SEQUENCE: 32

Met Gly Arg Leu Gly Glu Gly Leu Asn Cys Thr Val Lys Asn Ser Thr
1                   5                  10                  15

Cys Leu Asp Asp Ser Trp Ile His Pro Arg Asn Leu Thr Pro Ser Ser
               20                  25                  30

Pro Lys Asp Val Gln Val His Leu Asp Phe Ala Gln Thr Gln His Gly
          35                  40                  45

Asp Leu Leu Pro Ile Ile Gly Ile Arg Trp Thr Leu Gln Thr Asp Ala
     50                  55                  60

Ser Ile Leu Phe Leu Glu Gly Ala Glu Leu Ser Val Leu Gln Leu Asn
65                  70                  75                  80

Thr Asn Glu Arg Val Cys Val Lys Phe Glu Phe Leu Ser Lys Leu Lys
                85                  90                  95

His His His Lys Arg Trp His Phe Thr Phe Ser His Phe Val Val Glu
               100                 105                 110

Pro Gly Gln Glu Tyr Glu Val Thr Val His His Leu Pro Lys Pro Ile
               115                 120                 125

Pro Asp Gly Asp Pro Asn His Gln Ser Lys Asn Phe Leu Val Pro Gly
          130                 135                 140

Cys Glu Asp Pro Arg Met Arg Met Thr Thr Pro Cys Val Ser Ser Gly
145                 150                 155                 160

Ser Leu Trp Asp Pro Asn Ile Thr Ala Glu Ala Leu Glu Ala His Gln
               165                 170                 175

Leu Gln Val His Phe Thr Leu Trp Asn Glu Ser Ala Gln Tyr Gln Ile
               180                 185                 190

Leu Leu Thr Ser Phe Pro His Thr Glu Asn Arg Ser Cys Phe His Arg
          195                 200                 205

Val Leu Met Val Pro Glu Pro Thr Leu Lys Glu His His Gln Arg Ala
     210                 215                 220

Asn Ile Met Leu Thr Gly Ser Ser Ser Asn Trp Cys Cys Arg His Gln
225                 230                 235                 240
```

```
Val Gln Ile Gln Pro Phe Phe Ser Ser Cys Leu Asn Asp Cys Leu Arg
        245             250             255

His Ser Val Thr Val Pro Cys Pro Glu Ile Pro Asp Ala Pro Val Ser
        260             265             270

Ile Ala Asp Tyr Ile Pro Leu Trp Ala Tyr Gly Phe Ile Thr Gly Ile
        275             280             285

Ala Ile Leu Leu Val Gly Ser Val Ile Leu Ile Val Cys Met Ala
    290             295             300

Trp Arg Leu Pro Gly Ser His Cys Glu Lys Tyr Gly Asn Asp Ser Lys
305             310             315             320

Tyr Thr Asp Ile Gln Pro Lys Thr Ser Leu Thr Pro Pro Leu Lys
        325             330             335

Pro Arg Lys Val Trp Ile Val Tyr Ser Ala Asp His Pro Leu Tyr Val
        340             345             350

Asp Val Val Leu Lys Phe Ala Gln Phe Leu Leu Thr Val Cys Gly Thr
        355             360             365

Glu Val Ala Leu Asp Leu Leu Glu Glu Gln Val Ile Ser Glu Val Gly
    370             375             380

Val Met Thr Trp Val Gly Arg Gln Lys Gln Glu Met Val Glu Thr Asn
385             390             395             400

Ser Lys Ile Ile Ile Leu Cys Ser Arg Gly Thr Arg Ala Lys Trp Gln
        405             410             415

Ala Ile Leu Gly Trp Glu Glu Pro Ala Val Gln Leu Arg Cys Asp Arg
        420             425             430

Trp Lys Pro Ser Gly Asp Leu Phe Thr Ala Ala Met Asn Met Ile Leu
        435             440             445

Pro Asp Phe Lys Lys Pro Ala Cys Phe Gly Thr Tyr Ile Ile Cys Tyr
    450             455             460

Phe Arg Asp Ile Ser Ser Glu Ser Asp Ile Pro Asp Leu Phe Asn Ile
465             470             475             480

Thr Ser Arg Tyr Pro Leu Met Asp Lys Phe Glu Glu Val Tyr Phe Arg
        485             490             495

Ile Gln Asp Leu Glu Met Phe Glu Pro Gly Arg Met His Arg Val Gly
        500             505             510

Glu Leu Thr Gly Glu Asn Tyr Leu Gln Ser Pro Ser Gly Trp Gln Leu
        515             520             525

Lys Glu Ala Val Glu Arg Phe Arg Glu Trp Gln Val Arg Cys Pro Asp
    530             535             540

Trp Phe Glu Arg Glu Asn Leu Gly Ser Ala Asp Asp Gln Asp Leu Pro
545             550             555             560

Ser Leu Asp Glu Glu Val Phe Glu Glu Pro Leu Leu Pro Pro Gly Arg
        565             570             575

Gly Ile Val Lys Gln Lys Pro Leu Val His Glu Pro Ala Pro Glu Gly
        580             585             590

Cys Leu Val Ile Asp Leu Leu Val Gly Glu Glu Gly Arg Gly Pro Ser
        595             600             605

Arg Leu Glu Pro Gln Leu Gln Pro Gln Gly Glu Leu Met Ala Gln Thr
    610             615             620

Leu Gln Thr Val Val Phe Pro Val Lys Glu Val Pro Ser Ala Gln Ala
625             630             635             640

Val Glu Pro Val Pro His Thr Val Glu Ser Ser Thr Ala Gly Arg Leu
        645             650             655

Ala Val Val Glu Gly Asp Glu Ala Cys Pro Leu Leu Glu Gly Cys Gly
```

```
                 660              665              670

Pro Trp Arg Asn Ser Val Leu Cys Leu Pro Met Asp Ser Glu Glu Pro
        675              680              685

Pro Leu Cys Arg Thr Pro Met Ala Ser Pro Ser Tyr Leu Pro Glu Asp
        690              695              700

Val Arg Glu Gln Leu Glu Gly Leu Met Phe Ser Leu Leu Glu Gln Ser
705              710              715              720

Leu Ser Cys Gln Ala Gln Glu Gly Trp Asp Arg Ala Ala Val Ala Leu
            725              730              735

Lys Asp Phe Arg Thr Pro Tyr Glu Glu Glu Gln Arg Gln Ser Val Gln
            740              745              750

Ser Asp Gln Gly Tyr Ile Ser Arg Ser Ser Pro Gln Pro Pro Glu Gly
        755              760              765

Leu Met Glu Met Glu Glu Glu Glu Ala Glu Gln Asp Leu Gly Lys Ser
        770              775              780

Ala Lys Gln Leu Ser Pro Glu Asp Leu Glu Ser Leu Arg Ser Leu Gln
785              790              795              800

Arg Gln Leu Phe Phe Gln Glu Leu Gln Thr Asn Ser Gly Trp Asp Ser
            805              810              815

Val Glu Leu Glu Val Pro
            820

<210> SEQ ID NO 33
<211> LENGTH: 279
<212> TYPE: PRT
<213> ORGANISM: Unknown
<220> FEATURE:
<223> OTHER INFORMATION: Canine IL17A receptor (IL17Ra) ECD (binding
      domain fragment) amino acid sequence

<400> SEQUENCE: 33

Met Gly Arg Leu Gly Glu Gly Leu Asn Cys Thr Val Lys Asn Ser Thr
1               5               10              15

Cys Leu Asp Asp Ser Trp Ile His Pro Arg Asn Leu Thr Pro Ser Ser
            20              25              30

Pro Lys Asp Val Gln Val His Leu Asp Phe Ala Gln Thr Gln His Gly
        35              40              45

Asp Leu Leu Pro Ile Ile Gly Ile Arg Trp Thr Leu Gln Thr Asp Ala
        50              55              60

Ser Ile Leu Phe Leu Glu Gly Ala Glu Leu Ser Val Leu Gln Leu Asn
65              70              75              80

Thr Asn Glu Arg Val Cys Val Lys Phe Glu Phe Leu Ser Lys Leu Lys
            85              90              95

His His His Lys Arg Trp His Phe Thr Phe Ser His Phe Val Val Glu
            100             105             110

Pro Gly Gln Glu Tyr Glu Val Thr Val His His Leu Pro Lys Pro Ile
        115             120             125

Pro Asp Gly Asp Pro Asn His Gln Ser Lys Asn Phe Leu Val Pro Gly
        130             135             140

Cys Glu Asp Pro Arg Met Arg Met Thr Thr Pro Cys Val Ser Ser Gly
145             150             155             160

Ser Leu Trp Asp Pro Asn Ile Thr Ala Glu Ala Leu Glu Ala His Gln
            165             170             175

Leu Gln Val His Phe Thr Leu Trp Asn Glu Ser Ala Gln Tyr Gln Ile
        180             185             190
```

```
Leu Leu Thr Ser Phe Pro His Thr Glu Asn Arg Ser Cys Phe His Arg
        195                 200                 205

Val Leu Met Val Pro Glu Pro Thr Leu Lys Glu His His Gln Arg Ala
        210                 215                 220

Asn Ile Met Leu Thr Gly Ser Ser Ser Asn Trp Cys Cys Arg His Gln
225                     230                 235                 240

Val Gln Ile Gln Pro Phe Phe Ser Ser Cys Leu Asn Asp Cys Leu Arg
                245                 250                 255

His Ser Val Thr Val Pro Cys Pro Glu Ile Pro Asp Ala Pro Val Ser
                260                 265                 270

Ile Ala Asp Tyr Ile Pro Leu
        275
```

<210> SEQ ID NO 34
<211> LENGTH: 112
<212> TYPE: PRT
<213> ORGANISM: Artificial Sequence
<220> FEATURE:
<223> OTHER INFORMATION: Variable light chain amino acid sequence of
      mouse antibody clone A

<400> SEQUENCE: 34

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Arg Pro Gly Gln Ser
            35                  40                  45

Pro Asn Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110
```

<210> SEQ ID NO 35
<211> LENGTH: 120
<212> TYPE: PRT
<213> ORGANISM: Artificial Sequence
<220> FEATURE:
<223> OTHER INFORMATION: Variable heavy chain amino acid sequence of
      mouse antibody clone A

<400> SEQUENCE: 35

```
Gln Val Gln Leu Lys Glu Ser Gly Pro Gly Leu Val Ala Pro Ser Gln
1               5                   10                  15

Ser Leu Ser Ile Thr Cys Thr Ile Ser Gly Phe Ser Leu Thr Ser Asn
                20                  25                  30

Gly Val His Trp Val Arg Gln Ser Pro Gly Lys Asp Leu Glu Trp Leu
            35                  40                  45

Val Val Ile Trp Ser Asp Gly Thr Thr Thr Tyr Asn Ser Asp Phe Lys
        50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95
```

Arg His Tyr Asp Trp Gly Tyr Tyr Tyr Ala Met Asp Tyr Trp Gly Gln
        100               105             110

Gly Thr Ser Val Thr Val Ser Ser
        115           120

<210> SEQ ID NO 36
<211> LENGTH: 110
<212> TYPE: PRT
<213> ORGANISM: Artificial Sequence
<220> FEATURE:
<223> OTHER INFORMATION: Variable light chain amino acid sequence of
      mouse antibody clone D

<400> SEQUENCE: 36

Asp Ile Val Leu Thr Gln Ser Pro Ala Ser Leu Ala Val Ser Leu Gly
1               5               10              15

Gln Arg Ala Thr Ile Ser Tyr Arg Ala Ser Lys Ser Val Ser Thr Ser
        20              25              30

Gly Tyr Ser Tyr Met His Trp Asn Gln Gln Lys Pro Gly Gln Pro Pro
        35              40              45

Arg Leu Leu Ile Tyr Leu Val Ser Asn Leu Glu Ser Gly Val Pro Ala
    50              55              60

Arg Phe Ser Gly Ser Gly Ser Gly Thr Asp Phe Thr Leu Asn Ile His
65              70              75              80

Pro Val Glu Glu Glu Asp Ala Ala Thr Tyr Tyr Cys Gln His Ile Arg
            85              90              95

Glu Leu Tyr Thr Phe Gly Gly Gly Thr Lys Leu Glu Ile Lys
        100             105             110

<210> SEQ ID NO 37
<211> LENGTH: 122
<212> TYPE: PRT
<213> ORGANISM: Artificial Sequence
<220> FEATURE:
<223> OTHER INFORMATION: Variable heavy chain amino acid sequence of
      mouse antibody clone D

<400> SEQUENCE: 37

Glu Val Gln Leu Gln Gln Ser Gly Pro Glu Leu Val Lys Thr Gly Ala
1               5               10              15

Ser Val Lys Ile Ser Cys Lys Ala Ser Gly Tyr Ser Phe Thr Tyr Tyr
        20              25              30

Tyr Met His Trp Val Lys Gln Ser His Gly Lys Ser Leu Glu Trp Ile
        35              40              45

Gly Tyr Ile Ser Cys Phe Asn Gly Asp Thr Asn Tyr Asn Gln Glu Phe
        50              55              60

Lys Asp Lys Ala Thr Phe Thr Ala Asp Thr Ser Ser Ser Thr Ala Tyr
65              70              75              80

Met Gln Phe Asn Ser Leu Thr Ser Glu Asp Ser Ala Val Tyr Tyr Cys
            85              90              95

Ala Arg Gly Leu Ser Thr Leu Ile Thr Glu Gly Trp Phe Ala Tyr Trp
        100             105             110

Gly Gln Gly Thr Leu Val Thr Val Ser Ala
        115           120

<210> SEQ ID NO 38
<211> LENGTH: 112
<212> TYPE: PRT
<213> ORGANISM: Artificial Sequence
<220> FEATURE:

<223> OTHER INFORMATION: Variable light chain amino acid sequence of
      mouse antibody clone E

<400> SEQUENCE: 38

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Phe His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ala Pro Phe Thr Phe Gly Ser Gly Thr Lys Leu Glu Ile Lys
            100                 105                 110

<210> SEQ ID NO 39
<211> LENGTH: 120
<212> TYPE: PRT
<213> ORGANISM: Artificial Sequence
<220> FEATURE:
<223> OTHER INFORMATION: Variable heavy chain amino acid sequence of
      mouse antibody clone E

<400> SEQUENCE: 39

Gln Val Gln Leu Lys Glu Ser Gly Pro Gly Leu Val Ala Pro Ser Gln
1               5                   10                  15

Ser Leu Ser Ile Thr Cys Thr Ile Ser Gly Phe Ser Leu Thr Ser Asn
            20                  25                  30

Gly Val His Trp Val Arg Gln Pro Pro Gly Lys Gly Leu Glu Trp Leu
        35                  40                  45

Val Val Ile Trp Ser Asp Gly Thr Thr Thr Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg His Tyr Asp Arg Gly Tyr Tyr Tyr Ala Met Asp Tyr Trp Gly Gln
            100                 105                 110

Gly Thr Ser Val Thr Val Ser Ser
        115                 120

<210> SEQ ID NO 40
<211> LENGTH: 514
<212> TYPE: PRT
<213> ORGANISM: Homo sapiens

<400> SEQUENCE: 40

Ser Leu Arg Leu Leu Asp His Arg Ala Leu Val Cys Ser Gln Pro Gly
1               5                   10                  15

Leu Asn Cys Thr Val Lys Asn Ser Thr Cys Leu Asp Asp Ser Trp Ile
            20                  25                  30

His Pro Arg Asn Leu Thr Pro Ser Ser Pro Lys Asp Leu Gln Ile Gln
        35                  40                  45

Leu His Phe Ala His Thr Gln Gln Gly Asp Leu Phe Pro Val Ala His

-continued

```
                50                      55                      60

Ile Glu Trp Thr Leu Gln Thr Asp Ala Ser Ile Leu Tyr Leu Glu Gly
65                      70                      75                      80

Ala Glu Leu Ser Val Leu Gln Leu Asn Thr Asn Glu Arg Leu Cys Val
                85                      90                      95

Arg Phe Glu Phe Leu Ser Lys Leu Arg His His His Arg Arg Trp Arg
                100                     105                     110

Phe Thr Phe Ser His Phe Val Val Asp Pro Asp Gln Glu Tyr Glu Val
                115                     120                     125

Thr Val His His Leu Pro Lys Pro Ile Pro Asp Gly Asp Pro Asn His
                130                     135                     140

Gln Ser Lys Asn Phe Leu Val Pro Asp Cys Glu His Ala Arg Met Lys
145                     150                     155                     160

Val Thr Thr Pro Cys Met Ser Ser Gly Ser Leu Trp Asp Pro Asp Ile
                165                     170                     175

Thr Val Glu Thr Leu Glu Ala His Gln Leu Arg Val Ser Phe Thr Leu
                180                     185                     190

Trp Asn Glu Ser Thr His Tyr Gln Ile Leu Leu Thr Ser Phe Pro His
                195                     200                     205

Met Glu Asn His Ser Cys Phe Glu His Met His His Ile Pro Ala Pro
        210                     215                     220

Arg Pro Glu Glu Phe His Gln Arg Ser Asp Val Thr Leu Thr Leu Arg
225                     230                     235                     240

Asn Leu Lys Gly Cys Cys Arg His Gln Val Gln Ile Gln Pro Phe Phe
                245                     250                     255

Ser Ser Cys Leu Asn Asp Cys Leu Arg His Ser Ala Thr Val Ser Cys
                260                     265                     270

Pro Glu Met Pro Asp Thr Pro Glu Pro Ile Pro Asp Gly Ser Glu Ser
                275                     280                     285

Lys Tyr Gly Pro Pro Cys Pro Cys Pro Ala Pro Glu Ala Ala Gly
        290                     295                     300

Gly Pro Ser Val Phe Leu Phe Pro Pro Lys Pro Lys Asp Thr Leu Met
305                     310                     315                     320

Ile Ser Arg Thr Pro Glu Val Thr Cys Val Val Val Asp Val Ser Gln
                325                     330                     335

Glu Asp Pro Glu Val Gln Phe Asn Trp Tyr Val Asp Gly Val Glu Val
                340                     345                     350

His Asn Ala Lys Thr Lys Pro Arg Glu Glu Gln Phe Asn Ser Thr Tyr
                355                     360                     365

Arg Val Val Ser Val Leu Thr Val Leu His Gln Asp Trp Leu Asn Gly
                370                     375                     380

Lys Glu Tyr Lys Cys Lys Val Ser Asn Lys Gly Leu Pro Ser Ser Ile
385                     390                     395                     400

Glu Lys Thr Ile Ser Lys Ala Lys Gly Gln Pro Arg Glu Pro Gln Val
                405                     410                     415

Tyr Thr Leu Pro Pro Ser Gln Glu Glu Met Thr Lys Asn Gln Val Ser
                420                     425                     430

Leu Thr Cys Leu Val Lys Gly Phe Tyr Pro Ser Asp Ile Ala Val Glu
                435                     440                     445

Trp Glu Ser Asn Gly Gln Pro Glu Asn Asn Tyr Lys Thr Thr Pro Pro
        450                     455                     460

Val Leu Asp Ser Asp Gly Ser Phe Phe Leu Tyr Ser Arg Leu Thr Val
465                     470                     475                     480
```

-continued

```
Asp Lys Ser Arg Trp Gln Glu Gly Asn Val Phe Ser Cys Ser Val Met
            485             490             495

His Glu Ala Leu His Asn His Tyr Thr Gln Lys Ser Leu Ser Leu Ser
            500             505             510

Leu Gly

<210> SEQ ID NO 41
<211> LENGTH: 516
<212> TYPE: PRT
<213> ORGANISM: Artificial Sequence
<220> FEATURE:
<223> OTHER INFORMATION: Canine IL17Ra ECD-canine IgG-B-Fc

<400> SEQUENCE: 41

Met Gly Arg Leu Gly Glu Gly Leu Asn Cys Thr Val Lys Asn Ser Thr
1               5               10              15

Cys Leu Asp Asp Ser Trp Ile His Pro Arg Asn Leu Thr Pro Ser Ser
            20              25              30

Pro Lys Asp Val Gln Val His Leu Asp Phe Ala Gln Thr Gln His Gly
            35              40              45

Asp Leu Leu Pro Ile Ile Gly Ile Arg Trp Thr Leu Gln Thr Asp Ala
        50              55              60

Ser Ile Leu Phe Leu Glu Gly Ala Glu Leu Ser Val Leu Gln Leu Asn
65              70              75              80

Thr Asn Glu Arg Val Cys Val Lys Phe Glu Phe Leu Ser Lys Leu Lys
                85              90              95

His His His Lys Arg Trp His Phe Thr Phe Ser His Phe Val Val Glu
            100             105             110

Pro Gly Gln Glu Tyr Glu Val Thr Val His His Leu Pro Lys Pro Ile
            115             120             125

Pro Asp Gly Asp Pro Asn His Gln Ser Lys Asn Phe Leu Val Pro Gly
        130             135             140

Cys Glu Asp Pro Arg Met Arg Met Thr Thr Pro Cys Val Ser Ser Gly
145             150             155             160

Ser Leu Trp Asp Pro Asn Ile Thr Ala Glu Ala Leu Glu Ala His Gln
            165             170             175

Leu Gln Val His Phe Thr Leu Trp Asn Glu Ser Ala Gln Tyr Gln Ile
            180             185             190

Leu Leu Thr Ser Phe Pro His Thr Glu Asn Arg Ser Cys Phe His Arg
            195             200             205

Val Leu Met Val Pro Glu Pro Thr Leu Lys Glu His His Gln Arg Ala
        210             215             220

Asn Ile Met Leu Thr Gly Ser Ser Ser Asn Trp Cys Cys Arg His Gln
225             230             235             240

Val Gln Ile Gln Pro Phe Phe Ser Ser Cys Leu Asn Asp Cys Leu Arg
            245             250             255

His Ser Val Thr Val Pro Cys Pro Glu Ile Pro Asp Ala Pro Val Ser
            260             265             270

Ile Ala Asp Tyr Ile Gly Ser Pro Lys Arg Glu Asn Gly Arg Val Pro
            275             280             285

Arg Pro Pro Asp Cys Pro Lys Cys Pro Ala Pro Glu Met Leu Gly Gly
        290             295             300

Pro Ser Val Phe Ile Phe Pro Pro Lys Pro Lys Asp Thr Leu Leu Ile
305             310             315             320
```

-continued

```
Ala Arg Thr Pro Glu Val Thr Cys Val Val Val Asp Leu Asp Pro Glu
            325                 330                 335

Asp Pro Glu Val Gln Ile Ser Trp Phe Val Asp Gly Lys Gln Met Gln
            340                 345                 350

Thr Ala Lys Thr Gln Pro Arg Glu Glu Gln Phe Asn Gly Thr Tyr Arg
            355                 360                 365

Val Val Ser Val Leu Pro Ile Gly His Gln Asp Trp Leu Lys Gly Lys
    370                 375                 380

Gln Phe Thr Cys Lys Val Asn Asn Lys Ala Leu Pro Ser Pro Ile Glu
385                 390                 395                 400

Arg Thr Ile Ser Lys Ala Arg Gly Gln Ala His Gln Pro Ser Val Tyr
            405                 410                 415

Val Leu Pro Pro Ser Arg Glu Glu Leu Ser Lys Asn Thr Val Ser Leu
            420                 425                 430

Thr Cys Leu Ile Lys Asp Phe Phe Pro Pro Asp Ile Asp Val Glu Trp
            435                 440                 445

Gln Ser Asn Gly Gln Gln Glu Pro Glu Ser Lys Tyr Arg Thr Thr Pro
            450                 455                 460

Pro Gln Leu Asp Glu Asp Gly Ser Tyr Phe Leu Tyr Ser Lys Leu Ser
465                 470                 475                 480

Val Asp Lys Ser Arg Trp Gln Arg Gly Asp Thr Phe Ile Cys Ala Val
            485                 490                 495

Met His Glu Ala Leu His Asn His Tyr Thr Gln Glu Ser Leu Ser His
            500                 505                 510

Ser Pro Gly Lys
            515
```

```
<210> SEQ ID NO 42
<211> LENGTH: 545
<212> TYPE: PRT
<213> ORGANISM: Artificial Sequence
<220> FEATURE:
<223> OTHER INFORMATION: Canine IL17Ra ECD-huFc-polyHis

<400> SEQUENCE: 42
```

```
Met Asp Met Arg Val Pro Ala Gln Leu Leu Gly Leu Leu Leu Leu Trp
1               5                   10                  15

Leu Arg Gly Ala Arg Cys Met Gly Arg Leu Gly Glu Gly Leu Asn Cys
            20                  25                  30

Thr Val Lys Asn Ser Thr Cys Leu Asp Asp Ser Trp Ile His Pro Arg
            35                  40                  45

Asn Leu Thr Pro Ser Ser Pro Lys Asp Val Gln Val His Leu Asp Phe
    50                  55                  60

Ala Gln Thr Gln His Gly Asp Leu Leu Pro Ile Ile Gly Ile Arg Trp
65                  70                  75                  80

Thr Leu Gln Thr Asp Ala Ser Ile Leu Phe Leu Glu Gly Ala Glu Leu
            85                  90                  95

Ser Val Leu Gln Leu Asn Thr Asn Glu Arg Val Cys Val Lys Phe Glu
            100                 105                 110

Phe Leu Ser Lys Leu Lys His His His Lys Arg Trp His Phe Thr Phe
            115                 120                 125

Ser His Phe Val Val Glu Pro Gly Gln Glu Tyr Glu Val Thr Val His
    130                 135                 140

His Leu Pro Lys Pro Ile Pro Asp Gly Asp Pro Asn His Gln Ser Lys
145                 150                 155                 160
```

Asn Phe Leu Val Pro Gly Cys Glu Asp Pro Arg Met Arg Met Thr Thr
            165                 170             175

Pro Cys Val Ser Ser Gly Ser Leu Trp Asp Pro Asn Ile Thr Ala Glu
            180             185             190

Ala Leu Glu Ala His Gln Leu Gln Val His Phe Thr Leu Trp Asn Glu
            195             200             205

Ser Ala Gln Tyr Gln Ile Leu Leu Thr Ser Phe Pro His Thr Glu Asn
    210             215             220

Arg Ser Cys Phe His Arg Val Leu Met Val Pro Glu Pro Thr Leu Lys
225             230             235             240

Glu His His Gln Arg Ala Asn Ile Met Leu Thr Gly Ser Ser Ser Asn
            245             250             255

Trp Cys Cys Arg His Gln Val Gln Ile Gln Pro Phe Phe Ser Ser Cys
            260             265             270

Leu Asn Asp Cys Leu Arg His Ser Val Thr Val Pro Cys Pro Glu Ile
            275             280             285

Pro Asp Ala Pro Val Ser Ile Ala Asp Tyr Ile Gly Ser Glu Asn Leu
    290             295             300

Tyr Phe Gln Gly Pro Lys Ser Cys Asp Lys Thr His Thr Cys Pro Pro
305             310             315             320

Cys Pro Ala Pro Glu Leu Leu Gly Gly Pro Ser Val Phe Leu Phe Pro
            325             330             335

Pro Lys Pro Lys Asp Thr Leu Met Ile Ser Arg Thr Pro Glu Val Thr
            340             345             350

Cys Val Val Val Asp Val Ser His Glu Asp Pro Glu Val Lys Phe Asn
            355             360             365

Trp Tyr Val Asp Gly Val Glu Val His Asn Ala Lys Thr Lys Pro Arg
    370             375             380

Glu Glu Gln Tyr Asn Ser Thr Tyr Arg Val Val Ser Val Leu Thr Val
385             390             395             400

Leu His Gln Asp Trp Leu Asn Gly Lys Glu Tyr Lys Cys Lys Val Ser
            405             410             415

Asn Lys Ala Leu Pro Ala Pro Ile Glu Lys Thr Ile Ser Lys Ala Lys
            420             425             430

Gly Gln Pro Arg Glu Pro Gln Val Tyr Thr Leu Pro Pro Ser Arg Asp
            435             440             445

Glu Leu Thr Lys Asn Gln Val Ser Leu Thr Cys Leu Val Lys Gly Phe
    450             455             460

Tyr Pro Ser Asp Ile Ala Val Glu Trp Glu Ser Asn Gly Gln Pro Glu
465             470             475             480

Asn Asn Tyr Lys Thr Thr Pro Pro Val Leu Asp Ser Asp Gly Ser Phe
            485             490             495

Phe Leu Tyr Ser Lys Leu Thr Val Asp Lys Ser Arg Trp Gln Gln Gly
            500             505             510

Asn Val Phe Ser Cys Ser Val Met His Glu Ala Leu His Asn His Tyr
            515             520             525

Thr Gln Lys Ser Leu Ser Leu Ser Pro Gly Lys His His His His
    530             535             540

His
545

<210> SEQ ID NO 43
<211> LENGTH: 525
<212> TYPE: PRT

-continued

<213> ORGANISM: Artificial Sequence
<220> FEATURE:
<223> OTHER INFORMATION: Feline IL17Ra ECD-feline IgG-2-Fc

<400> SEQUENCE: 43

```
Ser Pro Arg Leu Leu Asp Tyr Pro Ala Pro Val Cys Ser Gln Gln Gly
1               5                   10                  15

Leu Asn Cys Val Val Lys Asn Ser Thr Cys Leu Asp Asp Ser Trp Ile
            20                  25                  30

His Leu Arg Asn Leu Thr Pro Ser Ser Pro Lys Asp Val Gln Val His
        35                  40                  45

Leu Asp Phe Val Gln Thr Gln His Gly Asp Leu Leu Pro Val Ala Gly
    50                  55                  60

Ile Arg Trp Thr Leu Gln Thr Asp Ala Ser Ile Leu Tyr Leu Glu Gly
65                  70                  75                  80

Ala Glu Leu Ser Val Leu Gln Leu Asn Thr Asn Glu Arg Leu Cys Val
                85                  90                  95

Lys Phe Glu Phe Leu Thr Arg Leu Lys His His His Lys Arg Trp His
            100                 105                 110

Phe Thr Phe Ser His Phe Val Val Glu Pro Gly Gln Glu Tyr Glu Val
            115                 120                 125

Thr Val His His Leu Pro Lys Pro Ile Pro Asp Gly Asp Pro Asn His
        130                 135                 140

Gln Ser Arg Asn Phe Pro Val Pro Gly Cys Glu Asp Pro Arg Met Lys
145                 150                 155                 160

Met Ile Thr Pro Cys Val Gly Ser Gly Ser Leu Trp Asp Pro Asn Ile
                165                 170                 175

Thr Val Glu Thr Leu Glu Ala Arg Gln Leu Trp Val Ser Phe Thr Leu
            180                 185                 190

Trp Asn Glu Ser Thr His Tyr Gln Ile Leu Leu Thr Ser Phe Pro His
            195                 200                 205

Thr Glu Asn His Ser Cys Phe Gln His Thr Leu Met Val Pro Glu Pro
        210                 215                 220

Ala Tyr Gln Asp Ser Arg Gln Arg Ser Asn Val Thr Leu Thr Leu Ser
225                 230                 235                 240

Asp Ser Asn Trp Cys Cys Arg His Arg Val Gln Ile Gln Pro Phe Phe
                245                 250                 255

Ser Ser Cys Leu Asn Asp Cys Leu Arg His Ser Ile Thr Val Pro Cys
            260                 265                 270

Pro Glu Ile Pro Asp Pro Pro Val Ser Ile Ala Asp Tyr Ile Gly Ser
            275                 280                 285

Pro Lys Thr Ala Ser Thr Ile Glu Ser Lys Thr Gly Glu Cys Pro Lys
        290                 295                 300

Cys Pro Val Pro Glu Ile Pro Gly Ala Pro Ser Val Phe Ile Phe Pro
305                 310                 315                 320

Pro Lys Pro Lys Asp Thr Leu Ser Ile Ser Arg Thr Pro Glu Val Thr
            325                 330                 335

Cys Leu Val Val Asp Leu Gly Pro Asp Asp Ser Asn Val Gln Ile Thr
            340                 345                 350

Trp Phe Val Asp Asn Thr Glu Met His Thr Ala Lys Thr Arg Pro Arg
            355                 360                 365

Glu Glu Gln Phe Asn Ser Thr Tyr Arg Val Val Ser Val Leu Pro Ile
        370                 375                 380

Leu His Gln Asp Trp Leu Lys Gly Lys Glu Phe Lys Cys Lys Val Asn
```

-continued

```
385                 390                 395                 400
Ser Lys Ser Leu Pro Ser Ala Met Glu Arg Thr Ile Ser Lys Ala Lys
            405                 410                 415

Gly Gln Pro His Glu Pro Gln Val Tyr Val Leu Pro Pro Thr Gln Glu
            420                 425                 430

Glu Leu Ser Glu Asn Lys Val Ser Val Thr Cys Leu Ile Lys Gly Phe
            435                 440                 445

His Pro Pro Asp Ile Ala Val Glu Trp Glu Ile Thr Gly Gln Pro Glu
    450                 455                 460

Pro Glu Asn Asn Tyr Gln Thr Thr Pro Pro Gln Leu Asp Ser Asp Gly
465                 470                 475                 480

Thr Tyr Phe Leu Tyr Ser Arg Leu Ser Val Asp Arg Ser His Trp Gln
                485                 490                 495

Arg Gly Asn Thr Tyr Thr Cys Ser Val Ser His Glu Ala Leu His Ser
            500                 505                 510

His His Thr Gln Lys Ser Leu Thr Gln Ser Pro Gly Lys
            515                 520                 525

<210> SEQ ID NO 44
<211> LENGTH: 516
<212> TYPE: PRT
<213> ORGANISM: Artificial Sequence
<220> FEATURE:
<223> OTHER INFORMATION: Equine IL17Ra ECD-equine IgG-2-Fc

<400> SEQUENCE: 44

Ser Pro Arg Leu Leu Glu His Pro Ala Pro Val Cys Ser Gln Gln Gly
1               5                   10                  15

Leu Asn Cys Thr Val Lys Asn Ser Thr Cys Leu Asp Asp Ser Trp Leu
            20                  25                  30

His Pro Pro His Leu Thr Pro Ser Ser Pro Lys Asp Val Gln Ile Gln
            35                  40                  45

Leu His Phe Ala His Thr Gln Gln Gly Asp Leu Leu Pro Val Ile His
    50                  55                  60

Ile Glu Trp Thr Leu Gln Thr Asp Ala Ser Ile Leu Tyr Leu Glu Gly
65                  70                  75                  80

Ala Glu Leu Ser Val Leu Gln Leu Ser Thr Asn Glu Arg Leu Cys Val
                85                  90                  95

Thr Phe Glu Phe Leu Ser Arg Leu Lys His His His Lys Arg Trp Arg
            100                 105                 110

Phe Thr Phe Ala His Phe Val Val Glu Pro Gly Gln Glu Tyr Glu Val
            115                 120                 125

Thr Val His His Leu Pro Lys Pro Phe Pro His Gly Asp Pro Asn His
    130                 135                 140

Gln Ser Arg Asn Phe Leu Val Pro Asp Cys Met Asp Pro Arg Met Arg
145                 150                 155                 160

Ile Thr Thr Pro Cys Val Ser Ser Gly Ser Leu Trp Asp Pro Asn Ile
            165                 170                 175

Thr Val Glu Thr Leu Glu Ala His Arg Leu Arg Val Asp Phe Thr Leu
            180                 185                 190

Trp Asn Glu Ser Ala Arg Tyr Gln Ile Leu Leu Ser Ser Phe Pro His
            195                 200                 205

Met Glu Asn Gln Ser Cys Phe Asp Asp Val Gln Asn Ile Leu Lys His
    210                 215                 220

Thr Pro Glu Ala Ser His Gln Arg Ala Asn Ile Thr Leu Thr Leu Ser
```

-continued

```
225             230             235             240

Asp Phe Asn Trp Cys Cys Arg His His Val Gln Ile Gln Pro Phe Phe
            245             250             255

Ser Ser Cys Leu Asn Asp Cys Leu Arg His Thr Val Thr Val Pro Cys
            260             265             270

Pro Glu Ile Pro Asp Thr Pro Asp Ser Thr Ala Asp Tyr Met Gly Ser
            275             280             285

Asp Met Ser Lys Cys Pro Lys Cys Pro Ala Pro Glu Leu Leu Gly Gly
    290             295             300

Pro Ser Val Phe Ile Phe Pro Pro Asn Pro Lys Asp Ala Leu Met Ile
305             310             315             320

Ser Arg Thr Pro Val Val Thr Cys Val Val Val Asn Leu Ser Asp Gln
            325             330             335

Tyr Pro Asp Val Gln Phe Ser Trp Tyr Val Asp Asn Thr Glu Val His
            340             345             350

Ser Ala Ile Thr Lys Gln Arg Glu Ala Gln Phe Asn Ser Thr Tyr Arg
            355             360             365

Val Val Ser Val Leu Pro Ile Gln His Gln Asp Trp Leu Ser Gly Lys
    370             375             380

Glu Phe Lys Cys Ser Val Thr Asn Val Gly Val Pro Gln Pro Ile Ser
385             390             395             400

Arg Ala Ile Ser Arg Gly Lys Gly Pro Ser Arg Val Pro Gln Val Tyr
            405             410             415

Val Leu Pro Pro His Pro Asp Glu Leu Ala Lys Ser Lys Val Ser Val
            420             425             430

Thr Cys Leu Val Lys Asp Phe Tyr Pro Pro Asp Ile Ser Val Glu Trp
            435             440             445

Gln Ser Asn Arg Trp Pro Glu Leu Glu Gly Lys Tyr Ser Thr Thr Pro
    450             455             460

Ala Gln Leu Asp Gly Asp Gly Ser Tyr Phe Leu Tyr Ser Lys Leu Ser
465             470             475             480

Leu Glu Thr Ser Arg Trp Gln Gln Val Glu Ser Phe Thr Cys Ala Val
            485             490             495

Met His Glu Ala Leu His Asn His Phe Thr Lys Thr Asp Ile Ser Glu
            500             505             510

Ser Leu Gly Lys
        515

<210> SEQ ID NO 45
<211> LENGTH: 237
<212> TYPE: PRT
<213> ORGANISM: Unknown
<220> FEATURE:
<223> OTHER INFORMATION: Canine IgG-B-Fc

<400> SEQUENCE: 45

Pro Lys Arg Glu Asn Gly Arg Val Pro Arg Pro Asp Cys Pro Lys
1               5               10              15

Cys Pro Ala Pro Glu Met Leu Gly Gly Pro Ser Val Phe Ile Phe Pro
            20              25              30

Pro Lys Pro Lys Asp Thr Leu Leu Ile Ala Arg Thr Pro Glu Val Thr
            35              40              45

Cys Val Val Val Asp Leu Asp Pro Glu Asp Pro Glu Val Gln Ile Ser
    50              55              60

Trp Phe Val Asp Gly Lys Gln Met Gln Thr Ala Lys Thr Gln Pro Arg
```

-continued

```
65              70              75              80

Glu Glu Gln Phe Asn Gly Thr Tyr Arg Val Val Ser Val Leu Pro Ile
            85              90              95

Gly His Gln Asp Trp Leu Lys Gly Lys Gln Phe Thr Cys Lys Val Asn
            100             105             110

Asn Lys Ala Leu Pro Ser Pro Ile Glu Arg Thr Ile Ser Lys Ala Arg
            115             120             125

Gly Gln Ala His Gln Pro Ser Val Tyr Val Leu Pro Pro Ser Arg Glu
            130             135             140

Glu Leu Ser Lys Asn Thr Val Ser Leu Thr Cys Leu Ile Lys Asp Phe
145             150             155             160

Phe Pro Pro Asp Ile Asp Val Glu Trp Gln Ser Asn Gly Gln Gln Glu
                165             170             175

Pro Glu Ser Lys Tyr Arg Thr Thr Pro Pro Gln Leu Asp Glu Asp Gly
            180             185             190

Ser Tyr Phe Leu Tyr Ser Lys Leu Ser Val Asp Lys Ser Arg Trp Gln
            195             200             205

Arg Gly Asp Thr Phe Ile Cys Ala Val Met His Glu Ala Leu His Asn
        210             215             220

His Tyr Thr Gln Glu Ser Leu Ser His Ser Pro Gly Lys
225             230             235

<210> SEQ ID NO 46
<211> LENGTH: 235
<212> TYPE: PRT
<213> ORGANISM: Unknown
<220> FEATURE:
<223> OTHER INFORMATION: Canine IgG-C-Fc

<400> SEQUENCE: 46

Ala Lys Glu Cys Glu Cys Lys Cys Asn Cys Asn Asn Cys Pro Cys Pro
1               5               10              15

Gly Cys Gly Leu Leu Gly Gly Pro Ser Val Phe Ile Phe Pro Pro Lys
            20              25              30

Pro Lys Asp Ile Leu Val Thr Ala Arg Thr Pro Thr Val Thr Cys Val
            35              40              45

Val Val Asp Leu Asp Pro Glu Asn Pro Glu Val Gln Ile Ser Trp Phe
        50              55              60

Val Asp Ser Lys Gln Val Gln Thr Ala Asn Thr Gln Pro Arg Glu Glu
65              70              75              80

Gln Ser Asn Gly Thr Tyr Arg Val Val Ser Val Leu Pro Ile Gly His
            85              90              95

Gln Asp Trp Leu Ser Gly Lys Gln Phe Lys Cys Lys Val Asn Asn Lys
            100             105             110

Ala Leu Pro Ser Pro Ile Glu Glu Ile Ile Ser Lys Thr Pro Gly Gln
            115             120             125

Ala His Gln Pro Asn Val Tyr Val Leu Pro Pro Ser Arg Asp Glu Met
        130             135             140

Ser Lys Asn Thr Val Thr Leu Thr Cys Leu Val Lys Asp Phe Phe Pro
145             150             155             160

Pro Glu Ile Asp Val Glu Trp Gln Ser Asn Gly Gln Gln Glu Pro Glu
                165             170             175

Ser Lys Tyr Arg Met Thr Pro Pro Gln Leu Asp Glu Asp Gly Ser Tyr
            180             185             190

Phe Leu Tyr Ser Lys Leu Ser Val Asp Lys Ser Arg Trp Gln Arg Gly
```

-continued

```
          195                 200                 205

Asp Thr Phe Ile Cys Ala Val Met His Glu Ala Leu His Asn His Tyr
    210                 215                 220

Thr Gln Ile Ser Leu Ser His Ser Pro Gly Lys
225                 230                 235

<210> SEQ ID NO 47
<211> LENGTH: 237
<212> TYPE: PRT
<213> ORGANISM: Artificial Sequence
<220> FEATURE:
<223> OTHER INFORMATION: Canine IgG-B-Fc variant 1 (C1q binding mutant)

<400> SEQUENCE: 47

Pro Lys Arg Glu Asn Gly Arg Val Pro Arg Pro Pro Asp Cys Pro Lys
1               5                   10                  15

Cys Pro Ala Pro Glu Met Leu Gly Gly Pro Ser Val Phe Ile Phe Pro
          20                  25                  30

Pro Lys Pro Lys Asp Thr Leu Leu Ile Ala Arg Thr Pro Glu Val Thr
          35                  40                  45

Cys Val Val Val Asp Leu Asp Pro Glu Asp Pro Glu Val Gln Ile Ser
      50                  55                  60

Trp Phe Val Asp Gly Lys Gln Met Gln Thr Ala Lys Thr Gln Pro Arg
65                  70                  75                  80

Glu Glu Gln Phe Asn Gly Thr Tyr Arg Val Val Ser Val Leu Pro Ile
                  85                  90                  95

Gly His Gln Asp Trp Leu Lys Gly Lys Gln Phe Thr Cys Arg Val Asn
              100                 105                 110

Asn Lys Ala Leu Pro Ser Pro Ile Glu Arg Thr Ile Ser Lys Ala Arg
          115                 120                 125

Gly Gln Ala His Gln Pro Ser Val Tyr Val Leu Pro Pro Ser Arg Glu
      130                 135                 140

Glu Leu Ser Lys Asn Thr Val Ser Leu Thr Cys Leu Ile Lys Asp Phe
145                 150                 155                 160

Phe Pro Pro Asp Ile Asp Val Glu Trp Gln Ser Asn Gly Gln Gln Glu
              165                 170                 175

Pro Glu Ser Lys Tyr Arg Thr Thr Pro Pro Gln Leu Asp Glu Asp Gly
              180                 185                 190

Ser Tyr Phe Leu Tyr Ser Lys Leu Ser Val Asp Lys Ser Arg Trp Gln
          195                 200                 205

Arg Gly Asp Thr Phe Ile Cys Ala Val Met His Glu Ala Leu His Asn
    210                 215                 220

His Tyr Thr Gln Glu Ser Leu Ser His Ser Pro Gly Lys
225                 230                 235

<210> SEQ ID NO 48
<211> LENGTH: 235
<212> TYPE: PRT
<213> ORGANISM: Artificial Sequence
<220> FEATURE:
<223> OTHER INFORMATION: Canine IgG-C-Fc variant 1 (C1q binding mutant)

<400> SEQUENCE: 48

Ala Lys Glu Cys Glu Cys Lys Cys Asn Cys Asn Asn Cys Pro Cys Pro
1               5                   10                  15

Gly Cys Gly Leu Leu Gly Gly Pro Ser Val Phe Ile Phe Pro Pro Lys
          20                  25                  30
```

-continued

```
Pro Lys Asp Ile Leu Val Thr Ala Arg Thr Pro Thr Val Thr Cys Val
        35                  40                  45

Val Val Asp Leu Asp Pro Glu Asn Pro Glu Val Gln Ile Ser Trp Phe
    50                  55                  60

Val Asp Ser Lys Gln Val Gln Thr Ala Asn Thr Gln Pro Arg Glu Glu
65                  70                  75                  80

Gln Ser Asn Gly Thr Tyr Arg Val Val Ser Val Leu Pro Ile Gly His
                85                  90                  95

Gln Asp Trp Leu Ser Gly Lys Gln Phe Lys Cys Arg Val Asn Asn Lys
                100                 105                 110

Ala Leu Pro Ser Pro Ile Glu Glu Ile Ile Ser Lys Thr Pro Gly Gln
            115                 120                 125

Ala His Gln Pro Asn Val Tyr Val Leu Pro Pro Ser Arg Asp Glu Met
    130                 135                 140

Ser Lys Asn Thr Val Thr Leu Thr Cys Leu Val Lys Asp Phe Phe Pro
145                 150                 155                 160

Pro Glu Ile Asp Val Glu Trp Gln Ser Asn Gly Gln Gln Glu Pro Glu
                165                 170                 175

Ser Lys Tyr Arg Met Thr Pro Pro Gln Leu Asp Glu Asp Gly Ser Tyr
                180                 185                 190

Phe Leu Tyr Ser Lys Leu Ser Val Asp Lys Ser Arg Trp Gln Arg Gly
                195                 200                 205

Asp Thr Phe Ile Cys Ala Val Met His Glu Ala Leu His Asn His Tyr
    210                 215                 220

Thr Gln Ile Ser Leu Ser His Ser Pro Gly Lys
225                 230                 235

<210> SEQ ID NO 49
<211> LENGTH: 237
<212> TYPE: PRT
<213> ORGANISM: Artificial Sequence
<220> FEATURE:
<223> OTHER INFORMATION: Canine IgG-B-Fc variant 2 (CD16 binding mutant
      1)

<400> SEQUENCE: 49

Pro Lys Arg Glu Asn Gly Arg Val Pro Arg Pro Pro Asp Cys Pro Lys
1                   5                   10                  15

Cys Pro Ala Pro Glu Met Leu Gly Gly Pro Ser Val Phe Ile Phe Pro
            20                  25                  30

Pro Lys Pro Lys Asp Thr Leu Leu Ile Ala Arg Thr Pro Glu Val Thr
            35                  40                  45

Cys Val Val Val Asp Leu Gly Pro Glu Asp Pro Glu Val Gln Ile Ser
    50                  55                  60

Trp Phe Val Asp Gly Lys Gln Met Gln Thr Ala Lys Thr Gln Pro Arg
65                  70                  75                  80

Glu Glu Gln Phe Asn Gly Thr Tyr Arg Val Val Ser Val Leu Pro Ile
                85                  90                  95

Gly His Gln Asp Trp Leu Lys Gly Lys Gln Phe Thr Cys Lys Val Asn
                100                 105                 110

Asn Ile Gly Leu Pro Ser Pro Ile Glu Arg Thr Ile Ser Lys Ala Arg
            115                 120                 125

Gly Gln Ala His Gln Pro Ser Val Tyr Val Leu Pro Pro Ser Arg Glu
    130                 135                 140

Glu Leu Ser Lys Asn Thr Val Ser Leu Thr Cys Leu Ile Lys Asp Phe
145                 150                 155                 160
```

-continued

```
Phe Pro Pro Asp Ile Asp Val Glu Trp Gln Ser Asn Gly Gln Gln Glu
                165             170             175

Pro Glu Ser Lys Tyr Arg Thr Thr Pro Pro Gln Leu Asp Glu Asp Gly
            180             185             190

Ser Tyr Phe Leu Tyr Ser Lys Leu Ser Val Asp Lys Ser Arg Trp Gln
            195             200             205

Arg Gly Asp Thr Phe Ile Cys Ala Val Met His Glu Ala Leu His Asn
        210             215             220

His Tyr Thr Gln Glu Ser Leu Ser His Ser Pro Gly Lys
225             230             235
```

```
<210> SEQ ID NO 50
<211> LENGTH: 235
<212> TYPE: PRT
<213> ORGANISM: Artificial Sequence
<220> FEATURE:
<223> OTHER INFORMATION: Canine IgG-C-Fc variant 2 (CD16 binding mutant
      1)

<400> SEQUENCE: 50
```

```
Ala Lys Glu Cys Glu Cys Lys Cys Asn Cys Asn Asn Cys Pro Cys Pro
1               5               10              15

Gly Cys Gly Leu Leu Gly Gly Pro Ser Val Phe Ile Phe Pro Pro Lys
            20              25              30

Pro Lys Asp Ile Leu Val Thr Ala Arg Thr Pro Thr Val Thr Cys Val
        35              40              45

Val Val Asp Leu Gly Pro Glu Asn Pro Glu Val Gln Ile Ser Trp Phe
    50              55              60

Val Asp Ser Lys Gln Val Gln Thr Ala Asn Thr Gln Pro Arg Glu Glu
65              70              75              80

Gln Ser Asn Gly Thr Tyr Arg Val Val Ser Val Leu Pro Ile Gly His
            85              90              95

Gln Asp Trp Leu Ser Gly Lys Gln Phe Lys Cys Lys Val Asn Asn Ile
            100             105             110

Gly Leu Pro Ser Pro Ile Glu Glu Ile Ile Ser Lys Thr Pro Gly Gln
            115             120             125

Ala His Gln Pro Asn Val Tyr Val Leu Pro Pro Ser Arg Asp Glu Met
        130             135             140

Ser Lys Asn Thr Val Thr Leu Thr Cys Leu Val Lys Asp Phe Phe Pro
145             150             155             160

Pro Glu Ile Asp Val Glu Trp Gln Ser Asn Gly Gln Gln Glu Pro Glu
                165             170             175

Ser Lys Tyr Arg Met Thr Pro Pro Gln Leu Asp Glu Asp Gly Ser Tyr
            180             185             190

Phe Leu Tyr Ser Lys Leu Ser Val Asp Lys Ser Arg Trp Gln Arg Gly
            195             200             205

Asp Thr Phe Ile Cys Ala Val Met His Glu Ala Leu His Asn His Tyr
        210             215             220

Thr Gln Ile Ser Leu Ser His Ser Pro Gly Lys
225             230             235
```

```
<210> SEQ ID NO 51
<211> LENGTH: 14
<212> TYPE: PRT
<213> ORGANISM: Artificial Sequence
<220> FEATURE:
<223> OTHER INFORMATION: Canine IL17A epitope C, expanded sequence
```

<400> SEQUENCE: 51

Cys Arg His Leu Gly Cys Val Asn Asn Glu Gly Asn Ile Asn
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Variable heavy chain CDR-H1 amino acid sequence
      of mouse antibody clone A

<400> SEQUENCE: 52

Gly Phe Ser Leu Thr Ser Asn Gly Val His
1               5                   10

<210> SEQ ID NO 53
<211> LENGTH: 19
<212> TYPE: PRT
<213> ORGANISM: Artificial Sequence
<220> FEATURE:
<223> OTHER INFORMATION: Variable heavy chain CDR-H2 amino acid sequence
      of mouse antibody clone A

<400> SEQUENCE: 53

Trp Leu Val Val Ile Trp Ser Asp Gly Thr Thr Thr Tyr Asn Ser Asp
1               5                   10                  15

Phe Lys Ser

<210> SEQ ID NO 54
<211> LENGTH: 14
<212> TYPE: PRT
<213> ORGANISM: Artificial Sequence
<220> FEATURE:
<223> OTHER INFORMATION: Variable heavy chain CDR-H3 amino acid sequence
      of mouse antibody clone A

<400> SEQUENCE: 54

Ala Arg His Tyr Asp Trp Gly Tyr Tyr Tyr Ala Met Asp Tyr
1               5                   10

<210> SEQ ID NO 55
<211> LENGTH: 25
<212> TYPE: PRT
<213> ORGANISM: Artificial Sequence
<220> FEATURE:
<223> OTHER INFORMATION: Variable region heavy chain framework HC-FR1
      amino acid sequence of mouse antibody clone A

<400> SEQUENCE: 55

Gln Val Gln Leu Lys Glu Ser Gly Pro Gly Leu Val Ala Pro Ser Gln
1               5                   10                  15

Ser Leu Ser Ile Thr Cys Thr Ile Ser
            20                  25

<210> SEQ ID NO 56
<211> LENGTH: 11
<212> TYPE: PRT
<213> ORGANISM: Artificial Sequence
<220> FEATURE:
<223> OTHER INFORMATION: Variable region heavy chain framework HC-FR2
      amino acid sequence of mouse antibody clone A

<400> SEQUENCE: 56

Trp Val Arg Gln Ser Pro Gly Lys Asp Leu Glu

```
1               5                    10
```

<210> SEQ ID NO 57
<211> LENGTH: 30
<212> TYPE: PRT
<213> ORGANISM: Artificial Sequence
<220> FEATURE:
<223> OTHER INFORMATION: Variable region heavy chain framework HC-FR3
      amino acid sequence of mouse antibody clone A

<400> SEQUENCE: 57

```
Arg Leu Ser Ile Ser Lys Asp Asn Ser Lys Ser Gln Val Phe Leu Lys
1               5                    10                  15

Met Asn Ser Leu Gln Thr Asp Asp Thr Ala Met Tyr Tyr Cys
                20                  25                  30
```

<210> SEQ ID NO 58
<211> LENGTH: 11
<212> TYPE: PRT
<213> ORGANISM: Artificial Sequence
<220> FEATURE:
<223> OTHER INFORMATION: Variable region heavy chain framework HC-FR4
      amino acid sequence of mouse antibody clone A

<400> SEQUENCE: 58

```
Trp Gly Gln Gly Thr Ser Val Thr Val Ser Ser
1               5                    10
```

<210> SEQ ID NO 59
<211> LENGTH: 17
<212> TYPE: PRT
<213> ORGANISM: Artificial Sequence
<220> FEATURE:
<223> OTHER INFORMATION: Variable light chain CDR-L1 amino acid sequence
      of mouse antibody clone A

<400> SEQUENCE: 59

```
Ser Ser Gln Ser Leu Val His Ser Asn Gly Asn Thr Tyr Leu His Trp
1               5                    10                  15

Tyr
```

<210> SEQ ID NO 60
<211> LENGTH: 11
<212> TYPE: PRT
<213> ORGANISM: Artificial Sequence
<220> FEATURE:
<223> OTHER INFORMATION: Variable light chain CDR-L2 amino acid sequence
      of mouse antibody clone A

<400> SEQUENCE: 60

```
Leu Leu Ile Tyr Lys Val Ser Asn Arg Phe Ser
1               5                    10
```

<210> SEQ ID NO 61
<211> LENGTH: 9
<212> TYPE: PRT
<213> ORGANISM: Artificial Sequence
<220> FEATURE:
<223> OTHER INFORMATION: Variable light chain CDR-L3 amino acid sequence
      of mouse antibody clone A

<400> SEQUENCE: 61

```
Ser Gln Ser Thr His Val Pro Phe Thr
1               5
```

<210> SEQ ID NO 62

<211> LENGTH: 24
<212> TYPE: PRT
<213> ORGANISM: Artificial Sequence
<220> FEATURE:
<223> OTHER INFORMATION: Variable region light chain framework LC-FR1
      amino acid sequence of mouse antibody clone A

<400> SEQUENCE: 62

Asp Val Val Met Thr Gln Thr Pro Leu Ser Leu Pro Val Ser Leu Gly
1               5                   10                  15

Asp Gln Ala Ser Ile Ser Cys Arg
            20

<210> SEQ ID NO 63
<211> LENGTH: 9
<212> TYPE: PRT
<213> ORGANISM: Artificial Sequence
<220> FEATURE:
<223> OTHER INFORMATION: Variable region light chain framework LC-FR2
      amino acid sequence of mouse antibody clone A

<400> SEQUENCE: 63

Leu Gln Arg Pro Gly Gln Ser Pro Asn
1               5

<210> SEQ ID NO 64
<211> LENGTH: 32
<212> TYPE: PRT
<213> ORGANISM: Artificial Sequence
<220> FEATURE:
<223> OTHER INFORMATION: Variable region light chain framework LC-FR3
      amino acid sequence of mouse antibody clone A

<400> SEQUENCE: 64

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Phe Cys
            20                  25                  30

<210> SEQ ID NO 65
<211> LENGTH: 10
<212> TYPE: PRT
<213> ORGANISM: Artificial Sequence
<220> FEATURE:
<223> OTHER INFORMATION: Variable region light chain framework LC-FR4
      amino acid sequence of mouse antibody clone A

<400> SEQUENCE: 65

Phe Gly Ser Gly Thr Lys Leu Glu Ile Lys
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Variable heavy chain CDR-H1 amino acid sequence
      of mouse antibody clone E

<400> SEQUENCE: 66

Gly Phe Ser Leu Thr Ser Asn Gly Val His
1               5                   10

<210> SEQ ID NO 67
<211> LENGTH: 19
<212> TYPE: PRT
<213> ORGANISM: Artificial Sequence -continued

```
<220> FEATURE:
<223> OTHER INFORMATION: Variable heavy chain CDR-H2 amino acid sequence
      of mouse antibody clone E

<400> SEQUENCE: 67

Trp Leu Val Val Ile Trp Ser Asp Gly Thr Thr Thr Tyr Asn Ser Ala
1               5                   10                  15

Leu Lys Ser

<210> SEQ ID NO 68
<211> LENGTH: 14
<212> TYPE: PRT
<213> ORGANISM: Artificial Sequence
<220> FEATURE:
<223> OTHER INFORMATION: Variable heavy chain CDR-H3 amino acid sequence
      of mouse antibody clone E

<400> SEQUENCE: 68

Ala Arg His Tyr Asp Arg Gly Tyr Tyr Tyr Ala Met Asp Tyr
1               5                   10

<210> SEQ ID NO 69
<211> LENGTH: 25
<212> TYPE: PRT
<213> ORGANISM: Artificial Sequence
<220> FEATURE:
<223> OTHER INFORMATION: Variable region heavy chain framework HC-FR1
      amino acid sequence of mouse antibody clone E

<400> SEQUENCE: 69

Gln Val Gln Leu Lys Glu Ser Gly Pro Gly Leu Val Ala Pro Ser Gln
1               5                   10                  15

Ser Leu Ser Ile Thr Cys Thr Ile Ser
            20                  25

<210> SEQ ID NO 70
<211> LENGTH: 11
<212> TYPE: PRT
<213> ORGANISM: Artificial Sequence
<220> FEATURE:
<223> OTHER INFORMATION: Variable region heavy chain framework HC-FR2
      amino acid sequence of mouse antibody clone E

<400> SEQUENCE: 70

Trp Val Arg Gln Pro Pro Gly Lys Gly Leu Glu
1               5                   10

<210> SEQ ID NO 71
<211> LENGTH: 30
<212> TYPE: PRT
<213> ORGANISM: Artificial Sequence
<220> FEATURE:
<223> OTHER INFORMATION: Variable region heavy chain framework HC-FR3
      amino acid sequence of mouse antibody clone E

<400> SEQUENCE: 71

Arg Leu Ser Ile Ser Lys Asp Asn Ser Lys Ser Gln Val Phe Leu Lys
1               5                   10                  15

Met Asn Ser Leu Gln Thr Asp Asp Thr Ala Met Tyr Tyr Cys
            20                  25                  30

<210> SEQ ID NO 72
<211> LENGTH: 11
<212> TYPE: PRT
<213> ORGANISM: Artificial Sequence
<220> FEATURE:
```

```
<223> OTHER INFORMATION: Variable region heavy chain framework HC-FR4
      amino acid sequence of mouse antibody clone E

<400> SEQUENCE: 72

Trp Gly Gln Gly Thr Ser Val Thr Val Ser Ser
1               5                   10

<210> SEQ ID NO 73
<211> LENGTH: 18
<212> TYPE: PRT
<213> ORGANISM: Artificial Sequence
<220> FEATURE:
<223> OTHER INFORMATION: Variable light chain CDR-L1 amino acid sequence
      of mouse antibody clone E

<400> SEQUENCE: 73

Arg Ser Ser Gln Ser Leu Val His Ser Asn Gly Asn Thr Tyr Phe His
1               5                   10                  15

Trp Tyr

<210> SEQ ID NO 74
<211> LENGTH: 11
<212> TYPE: PRT
<213> ORGANISM: Artificial Sequence
<220> FEATURE:
<223> OTHER INFORMATION: Variable light chain CDR-L2 amino acid sequence
      of mouse antibody clone E

<400> SEQUENCE: 74

Leu Leu Ile Tyr Lys Val Ser Asn Arg Phe Ser
1               5                   10

<210> SEQ ID NO 75
<211> LENGTH: 9
<212> TYPE: PRT
<213> ORGANISM: Artificial Sequence
<220> FEATURE:
<223> OTHER INFORMATION: Variable light chain CDR-L3 amino acid sequence
      of mouse antibody clone E

<400> SEQUENCE: 75

Ser Gln Ser Thr His Ala Pro Phe Thr
1               5

<210> SEQ ID NO 76
<211> LENGTH: 23
<212> TYPE: PRT
<213> ORGANISM: Artificial Sequence
<220> FEATURE:
<223> OTHER INFORMATION: Variable region light chain framework LC-FR1
      amino acid sequence of mouse antibody clone E

<400> SEQUENCE: 76

Asp Val Val Met Thr Gln Thr Pro Leu Ser Leu Pro Val Ser Leu Gly
1               5                   10                  15

Asp Gln Ala Ser Ile Ser Cys
            20

<210> SEQ ID NO 77
<211> LENGTH: 9
<212> TYPE: PRT
<213> ORGANISM: Artificial Sequence
<220> FEATURE:
<223> OTHER INFORMATION: Variable region light chain framework LC-FR2
      amino acid sequence of mouse antibody clone E

<400> SEQUENCE: 77
```

-continued

```
Leu Gln Lys Pro Gly Gln Ser Pro Lys
1               5

<210> SEQ ID NO 78
<211> LENGTH: 32
<212> TYPE: PRT
<213> ORGANISM: Artificial Sequence
<220> FEATURE:
<223> OTHER INFORMATION: Variable region light chain framework LC-FR3
      amino acid sequence of mouse antibody clone E

<400> SEQUENCE: 78

Gly Val Pro Asp Arg Phe Ser Gly Ser Gly Ser Gly Thr Asp Phe Thr
1               5                  10                  15

Leu Lys Ile Ser Arg Val Glu Ala Glu Asp Leu Gly Val Tyr Phe Cys
            20                  25                  30

<210> SEQ ID NO 79
<211> LENGTH: 10
<212> TYPE: PRT
<213> ORGANISM: Artificial Sequence
<220> FEATURE:
<223> OTHER INFORMATION: Variable region light chain framework LC-FR4
      amino acid sequence of mouse antibody clone E

<400> SEQUENCE: 79

Phe Gly Ser Gly Thr Lys Leu Glu Ile Lys
1               5                  10

<210> SEQ ID NO 80
<211> LENGTH: 10
<212> TYPE: PRT
<213> ORGANISM: Artificial Sequence
<220> FEATURE:
<223> OTHER INFORMATION: Variable heavy chain CDR-H1 amino acid sequence
      of mouse antibody clone D

<400> SEQUENCE: 80

Gly Tyr Ser Phe Thr Tyr Tyr Tyr Met His
1               5                  10

<210> SEQ ID NO 81
<211> LENGTH: 20
<212> TYPE: PRT
<213> ORGANISM: Artificial Sequence
<220> FEATURE:
<223> OTHER INFORMATION: Variable heavy chain CDR-H2 amino acid sequence
      of mouse antibody clone D

<400> SEQUENCE: 81

Trp Ile Gly Tyr Ile Ser Cys Phe Asn Gly Asp Thr Asn Tyr Asn Gln
1               5                  10                  15

Glu Phe Lys Asp
            20

<210> SEQ ID NO 82
<211> LENGTH: 15
<212> TYPE: PRT
<213> ORGANISM: Artificial Sequence
<220> FEATURE:
<223> OTHER INFORMATION: Variable heavy chain CDR-H3 amino acid sequence
      of mouse antibody clone D

<400> SEQUENCE: 82

Ala Arg Gly Leu Ser Thr Leu Ile Thr Glu Gly Trp Phe Ala Tyr
1               5                  10                  15
```

-continued

```
<210> SEQ ID NO 83
<211> LENGTH: 25
<212> TYPE: PRT
<213> ORGANISM: Artificial Sequence
<220> FEATURE:
<223> OTHER INFORMATION: Variable region heavy chain framework HC-FR1
      amino acid sequence of mouse antibody clone D

<400> SEQUENCE: 83

Glu Val Gln Leu Gln Gln Ser Gly Pro Glu Leu Val Lys Thr Gly Ala
1               5                   10                  15

Ser Val Lys Ile Ser Cys Lys Ala Ser
            20                  25

<210> SEQ ID NO 84
<211> LENGTH: 11
<212> TYPE: PRT
<213> ORGANISM: Artificial Sequence
<220> FEATURE:
<223> OTHER INFORMATION: Variable region heavy chain framework HC-FR2
      amino acid sequence of mouse antibody clone D

<400> SEQUENCE: 84

Trp Val Lys Gln Ser His Gly Lys Ser Leu Glu
1               5                   10

<210> SEQ ID NO 85
<211> LENGTH: 30
<212> TYPE: PRT
<213> ORGANISM: Artificial Sequence
<220> FEATURE:
<223> OTHER INFORMATION: Variable region heavy chain framework HC-FR3
      amino acid sequence of mouse antibody clone D

<400> SEQUENCE: 85

Lys Ala Thr Phe Thr Ala Asp Thr Ser Ser Ser Thr Ala Tyr Met Gln
1               5                   10                  15

Phe Asn Ser Leu Thr Ser Glu Asp Ser Ala Val Tyr Tyr Cys
            20                  25                  30

<210> SEQ ID NO 86
<211> LENGTH: 11
<212> TYPE: PRT
<213> ORGANISM: Artificial Sequence
<220> FEATURE:
<223> OTHER INFORMATION: Variable region heavy chain framework HC-FR4
      amino acid sequence of mouse antibody clone D

<400> SEQUENCE: 86

Trp Gly Gln Gly Thr Leu Val Thr Val Ser Ala
1               5                   10

<210> SEQ ID NO 87
<211> LENGTH: 17
<212> TYPE: PRT
<213> ORGANISM: Artificial Sequence
<220> FEATURE:
<223> OTHER INFORMATION: Variable light chain CDR-L1 amino acid sequence
      of mouse antibody clone D

<400> SEQUENCE: 87

Arg Ala Ser Lys Ser Val Ser Thr Ser Gly Tyr Ser Tyr Met His Trp
1               5                   10                  15

Asn
```

-continued

```
<210> SEQ ID NO 88
<211> LENGTH: 11
<212> TYPE: PRT
<213> ORGANISM: Artificial Sequence
<220> FEATURE:
<223> OTHER INFORMATION: Variable light chain CDR-L2 amino acid sequence
      of mouse antibody clone D

<400> SEQUENCE: 88

Leu Leu Ile Tyr Leu Val Ser Asn Leu Glu Ser
1               5                   10

<210> SEQ ID NO 89
<211> LENGTH: 8
<212> TYPE: PRT
<213> ORGANISM: Artificial Sequence
<220> FEATURE:
<223> OTHER INFORMATION: Variable light chain CDR-L3 amino acid sequence
      of mouse antibody clone D

<400> SEQUENCE: 89

Gln His Ile Arg Glu Leu Tyr Thr
1               5

<210> SEQ ID NO 90
<211> LENGTH: 23
<212> TYPE: PRT
<213> ORGANISM: Artificial Sequence
<220> FEATURE:
<223> OTHER INFORMATION: Variable region light chain framework LC-FR1
      amino acid sequence of mouse antibody clone D

<400> SEQUENCE: 90

Asp Ile Val Leu Thr Gln Ser Pro Ala Ser Leu Ala Val Ser Leu Gly
1               5                   10                  15

Gln Arg Ala Thr Ile Ser Tyr
            20

<210> SEQ ID NO 91
<211> LENGTH: 9
<212> TYPE: PRT
<213> ORGANISM: Artificial Sequence
<220> FEATURE:
<223> OTHER INFORMATION: Variable region light chain framework LC-FR2
      amino acid sequence of mouse antibody clone D

<400> SEQUENCE: 91

Gln Gln Lys Pro Gly Gln Pro Pro Arg
1               5

<210> SEQ ID NO 92
<211> LENGTH: 32
<212> TYPE: PRT
<213> ORGANISM: Artificial Sequence
<220> FEATURE:
<223> OTHER INFORMATION: Variable region light chain framework LC-FR3
      amino acid sequence of mouse antibody clone D

<400> SEQUENCE: 92

Gly Val Pro Ala Arg Phe Ser Gly Ser Gly Ser Gly Thr Asp Phe Thr
1               5                   10                  15

Leu Asn Ile His Pro Val Glu Glu Glu Asp Ala Ala Thr Tyr Tyr Cys
            20                  25                  30

<210> SEQ ID NO 93
<211> LENGTH: 10
```

-continued

<212> TYPE: PRT
<213> ORGANISM: Artificial Sequence
<220> FEATURE:
<223> OTHER INFORMATION: Variable region light chain framework LC-FR4
      amino acid sequence of mouse antibody clone D

<400> SEQUENCE: 93

Phe Gly Gly Gly Thr Lys Leu Glu Ile Lys
1               5                   10

<210> SEQ ID NO 94
<211> LENGTH: 261
<212> TYPE: PRT
<213> ORGANISM: Artificial Sequence
<220> FEATURE:
<223> OTHER INFORMATION: Truncated canine IL17Ra ECD

<400> SEQUENCE: 94

Leu Gly Glu Gly Leu Asn Cys Thr Val Lys Asn Ser Thr Cys Leu Asp
1               5                   10                  15

Asp Ser Trp Ile His Pro Arg Asn Leu Thr Pro Ser Ser Pro Lys Asp
                20                  25                  30

Val Gln Val His Leu Asp Phe Ala Gln Thr Gln His Gly Asp Leu Leu
        35                  40                  45

Pro Ile Ile Gly Ile Arg Trp Thr Leu Gln Thr Asp Ala Ser Ile Leu
    50                  55                  60

Phe Leu Glu Gly Ala Glu Leu Ser Val Leu Gln Leu Asn Thr Asn Glu
65                  70                  75                  80

Arg Val Cys Val Lys Phe Glu Phe Leu Ser Lys Leu Lys His His His
                85                  90                  95

Lys Arg Trp His Phe Thr Phe Ser His Phe Val Val Glu Pro Gly Gln
                100                 105                 110

Glu Tyr Glu Val Thr Val His His Leu Pro Lys Pro Ile Pro Asp Gly
        115                 120                 125

Asp Pro Asn His Gln Ser Lys Asn Phe Leu Val Pro Gly Cys Glu Asp
    130                 135                 140

Pro Arg Met Arg Met Thr Thr Pro Cys Val Ser Ser Gly Ser Leu Trp
145                 150                 155                 160

Asp Pro Asn Ile Thr Ala Glu Ala Leu Glu Ala His Gln Leu Gln Val
                165                 170                 175

His Phe Thr Leu Trp Asn Glu Ser Ala Gln Tyr Gln Ile Leu Leu Thr
                180                 185                 190

Ser Phe Pro His Thr Glu Asn Arg Ser Cys Phe His Arg Val Leu Met
        195                 200                 205

Val Pro Glu Pro Thr Leu Lys Glu His His Gln Arg Ala Asn Ile Met
    210                 215                 220

Leu Thr Gly Ser Ser Ser Asn Trp Cys Cys Arg His Gln Val Gln Ile
225                 230                 235                 240

Gln Pro Phe Phe Ser Ser Cys Leu Asn Asp Cys Leu Arg His Ser Val
                245                 250                 255

Thr Val Pro Cys Pro
            260

<210> SEQ ID NO 95
<211> LENGTH: 780
<212> TYPE: PRT
<213> ORGANISM: Unknown
<220> FEATURE:
<223> OTHER INFORMATION: IL4R/IL13R-canine IgG-B

<400> SEQUENCE: 95

```
Met Ala Val Leu Gly Leu Leu Phe Cys Leu Val Thr Phe Pro Ser Cys
1               5                   10                  15

Val Leu Ser Thr Glu Thr Gln Pro Pro Val Thr Asn Leu Ser Val Ser
            20                  25                  30

Val Glu Asn Leu Cys Thr Val Ile Trp Thr Trp Asp Pro Pro Glu Gly
        35                  40                  45

Ala Ser Pro Asn Cys Thr Leu Arg Tyr Phe Ser His Phe Asp Asn Lys
    50                  55                  60

Gln Asp Lys Lys Ile Ala Pro Glu Thr His Arg Ser Lys Glu Val Pro
65                  70                  75                  80

Leu Asn Glu Arg Ile Cys Leu Gln Val Gly Ser Gln Cys Ser Thr Asn
                85                  90                  95

Glu Ser Asp Asn Pro Ser Ile Leu Val Glu Lys Cys Thr Pro Pro Pro
            100                 105                 110

Glu Gly Asp Pro Glu Ser Ala Val Thr Glu Leu Gln Cys Val Trp His
        115                 120                 125

Asn Leu Ser Tyr Met Lys Cys Thr Trp Leu Pro Gly Arg Asn Thr Ser
    130                 135                 140

Pro Asp Thr Asn Tyr Thr Leu Tyr Tyr Trp His Ser Ser Leu Gly Lys
145                 150                 155                 160

Ile Leu Gln Cys Glu Asp Ile Tyr Arg Glu Gly Gln His Ile Gly Cys
                165                 170                 175

Ser Phe Ala Leu Thr Asn Leu Lys Asp Ser Ser Phe Glu Gln His Ser
            180                 185                 190

Val Gln Ile Val Val Lys Asp Asn Ala Gly Lys Ile Arg Pro Ser Phe
        195                 200                 205

Asn Ile Val Pro Leu Thr Ser His Val Lys Pro Asp Pro Pro His Ile
    210                 215                 220

Lys Arg Leu Phe Phe Gln Asn Gly Asn Leu Tyr Val Gln Trp Lys Asn
225                 230                 235                 240

Pro Gln Asn Phe Tyr Ser Arg Cys Leu Ser Tyr Gln Val Glu Val Asn
                245                 250                 255

Asn Ser Gln Thr Glu Thr Asn Asp Ile Phe Tyr Val Glu Glu Ala Lys
            260                 265                 270

Cys Gln Asn Ser Glu Phe Glu Gly Asn Leu Glu Gly Thr Ile Cys Phe
        275                 280                 285

Met Val Pro Gly Val Leu Pro Asp Thr Leu Asn Thr Val Arg Ile Arg
    290                 295                 300

Val Arg Thr Asn Lys Leu Cys Tyr Glu Asp Asp Lys Leu Trp Ser Asn
305                 310                 315                 320

Trp Ser Gln Ala Met Ser Ile Gly Glu Asn Thr Asp Pro Thr Gly Gly
                325                 330                 335

Gly Ser Gly Ser Gly Ser Val Lys Val Leu His Glu Pro Ser Cys Phe
            340                 345                 350

Ser Asp Tyr Ile Ser Thr Ser Val Cys Gln Trp Lys Met Asp His Pro
        355                 360                 365

Thr Asn Cys Ser Ala Glu Leu Arg Leu Ser Tyr Gln Leu Asp Phe Met
    370                 375                 380

Gly Ser Glu Asn His Thr Cys Val Pro Glu Asn Arg Glu Asp Ser Val
385                 390                 395                 400

Cys Val Cys Ser Met Pro Ile Asp Asp Ala Val Glu Ala Asp Val Tyr
```

-continued

```
                    405                      410                      415

Gln Leu Asp Leu Trp Ala Gly Gln Gln Leu Leu Trp Ser Gly Ser Phe
            420                      425                      430

Gln Pro Ser Lys His Val Lys Pro Arg Thr Pro Gly Asn Leu Thr Val
            435                      440                      445

His Pro Asn Ile Ser His Thr Trp Leu Leu Met Trp Thr Asn Pro Tyr
        450                      455                      460

Pro Thr Glu Asn His Leu His Ser Glu Leu Thr Tyr Met Val Asn Val
465                      470                      475                      480

Ser Asn Asp Asn Asp Pro Glu Asp Phe Lys Val Tyr Asn Val Thr Tyr
                485                      490                      495

Met Gly Pro Thr Leu Arg Leu Ala Ala Ser Thr Leu Lys Ser Gly Ala
            500                      505                      510

Ser Tyr Ser Ala Arg Val Arg Ala Trp Ala Gln Thr Tyr Asn Ser Thr
            515                      520                      525

Trp Ser Asp Trp Ser Pro Ser Thr Thr Trp Leu Asn Tyr Tyr Glu Pro
        530                      535                      540

Lys Arg Glu Asn Gly Arg Val Pro Arg Pro Asp Cys Pro Lys Cys
545                      550                      555                      560

Pro Ala Pro Glu Met Leu Gly Gly Pro Ser Val Phe Ile Phe Pro Pro
                565                      570                      575

Lys Pro Lys Asp Thr Leu Leu Ile Ala Arg Thr Pro Glu Val Thr Cys
            580                      585                      590

Val Val Val Asp Leu Asp Pro Glu Asp Pro Glu Val Gln Ile Ser Trp
            595                      600                      605

Phe Val Asp Gly Lys Gln Met Gln Thr Ala Lys Thr Gln Pro Arg Glu
        610                      615                      620

Glu Gln Phe Asn Gly Thr Tyr Arg Val Val Ser Val Leu Pro Ile Gly
625                      630                      635                      640

His Gln Asp Trp Leu Lys Gly Lys Gln Phe Thr Cys Lys Val Asn Asn
            645                      650                      655

Lys Ala Leu Pro Ser Pro Ile Glu Arg Thr Ile Ser Lys Ala Arg Gly
            660                      665                      670

Gln Ala His Gln Pro Ser Val Tyr Val Leu Pro Pro Ser Arg Glu Glu
            675                      680                      685

Leu Ser Lys Asn Thr Val Ser Leu Thr Cys Leu Ile Lys Asp Phe Phe
        690                      695                      700

Pro Pro Asp Ile Asp Val Glu Trp Gln Ser Asn Gly Gln Gln Glu Pro
705                      710                      715                      720

Glu Ser Lys Tyr Arg Thr Thr Pro Pro Gln Leu Asp Glu Asp Gly Ser
                725                      730                      735

Tyr Phe Leu Tyr Ser Lys Leu Ser Val Asp Lys Ser Arg Trp Gln Arg
            740                      745                      750

Gly Asp Thr Phe Ile Cys Ala Val Met His Glu Ala Leu His Asn His
            755                      760                      765

Tyr Thr Gln Glu Ser Leu Ser His Ser Pro Gly Lys
            770                      775                      780
```

<210> SEQ ID NO 96
<211> LENGTH: 780
<212> TYPE: PRT
<213> ORGANISM: Artificial Sequence
<220> FEATURE:
<223> OTHER INFORMATION: IL4R/IL13R-canine IgG-B variant 1 (C1q binding mutant)

-continued

<400> SEQUENCE: 96

```
Met Ala Val Leu Gly Leu Leu Phe Cys Leu Val Thr Phe Pro Ser Cys
1               5                   10                  15

Val Leu Ser Thr Glu Thr Gln Pro Pro Val Thr Asn Leu Ser Val Ser
            20                  25                  30

Val Glu Asn Leu Cys Thr Val Ile Trp Thr Trp Asp Pro Pro Glu Gly
        35                  40                  45

Ala Ser Pro Asn Cys Thr Leu Arg Tyr Phe Ser His Phe Asp Asn Lys
        50                  55                  60

Gln Asp Lys Lys Ile Ala Pro Glu Thr His Arg Ser Lys Glu Val Pro
65                  70                  75                  80

Leu Asn Glu Arg Ile Cys Leu Gln Val Gly Ser Gln Cys Ser Thr Asn
                85                  90                  95

Glu Ser Asp Asn Pro Ser Ile Leu Val Glu Lys Cys Thr Pro Pro Pro
                100                 105                 110

Glu Gly Asp Pro Glu Ser Ala Val Thr Glu Leu Gln Cys Val Trp His
            115                 120                 125

Asn Leu Ser Tyr Met Lys Cys Thr Trp Leu Pro Gly Arg Asn Thr Ser
    130                 135                 140

Pro Asp Thr Asn Tyr Thr Leu Tyr Tyr Trp His Ser Ser Leu Gly Lys
145                 150                 155                 160

Ile Leu Gln Cys Glu Asp Ile Tyr Arg Glu Gly Gln His Ile Gly Cys
                165                 170                 175

Ser Phe Ala Leu Thr Asn Leu Lys Asp Ser Ser Phe Glu Gln His Ser
            180                 185                 190

Val Gln Ile Val Val Lys Asp Asn Ala Gly Lys Ile Arg Pro Ser Phe
            195                 200                 205

Asn Ile Val Pro Leu Thr Ser His Val Lys Pro Asp Pro Pro His Ile
    210                 215                 220

Lys Arg Leu Phe Phe Gln Asn Gly Asn Leu Tyr Val Gln Trp Lys Asn
225                 230                 235                 240

Pro Gln Asn Phe Tyr Ser Arg Cys Leu Ser Tyr Gln Val Glu Val Asn
                245                 250                 255

Asn Ser Gln Thr Glu Thr Asn Asp Ile Phe Tyr Val Glu Glu Ala Lys
            260                 265                 270

Cys Gln Asn Ser Glu Phe Glu Gly Asn Leu Glu Gly Thr Ile Cys Phe
            275                 280                 285

Met Val Pro Gly Val Leu Pro Asp Thr Leu Asn Thr Val Arg Ile Arg
    290                 295                 300

Val Arg Thr Asn Lys Leu Cys Tyr Glu Asp Asp Lys Leu Trp Ser Asn
305                 310                 315                 320

Trp Ser Gln Ala Met Ser Ile Gly Glu Asn Thr Asp Pro Thr Gly Gly
            325                 330                 335

Gly Ser Gly Ser Gly Ser Val Lys Val Leu His Glu Pro Ser Cys Phe
            340                 345                 350

Ser Asp Tyr Ile Ser Thr Ser Val Cys Gln Trp Lys Met Asp His Pro
            355                 360                 365

Thr Asn Cys Ser Ala Glu Leu Arg Leu Ser Tyr Gln Leu Asp Phe Met
    370                 375                 380

Gly Ser Glu Asn His Thr Cys Val Pro Glu Asn Arg Glu Asp Ser Val
385                 390                 395                 400

Cys Val Cys Ser Met Pro Ile Asp Asp Ala Val Glu Ala Asp Val Tyr
```

```
                    405                410                415

Gln Leu Asp Leu Trp Ala Gly Gln Gln Leu Leu Trp Ser Gly Ser Phe
            420                425                430

Gln Pro Ser Lys His Val Lys Pro Arg Thr Pro Gly Asn Leu Thr Val
            435                440                445

His Pro Asn Ile Ser His Thr Trp Leu Leu Met Trp Thr Asn Pro Tyr
        450                455                460

Pro Thr Glu Asn His Leu His Ser Glu Leu Thr Tyr Met Val Asn Val
465                470                475                480

Ser Asn Asp Asn Asp Pro Glu Asp Phe Lys Val Tyr Asn Val Thr Tyr
                485                490                495

Met Gly Pro Thr Leu Arg Leu Ala Ala Ser Thr Leu Lys Ser Gly Ala
            500                505                510

Ser Tyr Ser Ala Arg Val Arg Ala Trp Ala Gln Thr Tyr Asn Ser Thr
            515                520                525

Trp Ser Asp Trp Ser Pro Ser Thr Thr Trp Leu Asn Tyr Tyr Glu Pro
        530                535                540

Lys Arg Glu Asn Gly Arg Val Pro Arg Pro Asp Cys Pro Lys Cys
545                550                555                560

Pro Ala Pro Glu Met Leu Gly Gly Pro Ser Val Phe Ile Phe Pro Pro
                565                570                575

Lys Pro Lys Asp Thr Leu Leu Ile Ala Arg Thr Pro Glu Val Thr Cys
            580                585                590

Val Val Val Asp Leu Asp Pro Glu Asp Pro Glu Val Gln Ile Ser Trp
            595                600                605

Phe Val Asp Gly Lys Gln Met Gln Thr Ala Lys Thr Gln Pro Arg Glu
        610                615                620

Glu Gln Phe Asn Gly Thr Tyr Arg Val Val Ser Val Leu Pro Ile Gly
625                630                635                640

His Gln Asp Trp Leu Lys Gly Lys Gln Phe Thr Cys Arg Val Asn Asn
            645                650                655

Lys Ala Leu Pro Ser Pro Ile Glu Arg Thr Ile Ser Lys Ala Arg Gly
            660                665                670

Gln Ala His Gln Pro Ser Val Tyr Val Leu Pro Pro Ser Arg Glu Glu
            675                680                685

Leu Ser Lys Asn Thr Val Ser Leu Thr Cys Leu Ile Lys Asp Phe Phe
        690                695                700

Pro Pro Asp Ile Asp Val Glu Trp Gln Ser Asn Gly Gln Gln Glu Pro
705                710                715                720

Glu Ser Lys Tyr Arg Thr Thr Pro Pro Gln Leu Asp Glu Asp Gly Ser
                725                730                735

Tyr Phe Leu Tyr Ser Lys Leu Ser Val Asp Lys Ser Arg Trp Gln Arg
            740                745                750

Gly Asp Thr Phe Ile Cys Ala Val Met His Glu Ala Leu His Asn His
            755                760                765

Tyr Thr Gln Glu Ser Leu Ser His Ser Pro Gly Lys
770                775                780
```

<210> SEQ ID NO 97
<211> LENGTH: 273
<212> TYPE: PRT
<213> ORGANISM: Homo sapiens

<400> SEQUENCE: 97

```
Ser Leu Arg Leu Leu Asp His Arg Ala Leu Val Cys Ser Gln Pro Gly
1               5                   10                  15

Leu Asn Cys Thr Val Lys Asn Ser Thr Cys Leu Asp Asp Ser Trp Ile
            20                  25                  30

His Pro Arg Asn Leu Thr Pro Ser Ser Pro Lys Asp Leu Gln Ile Gln
        35                  40                  45

Leu His Phe Ala His Thr Gln Gln Gly Asp Leu Phe Pro Val Ala His
    50                  55                  60

Ile Glu Trp Thr Leu Gln Thr Asp Ala Ser Ile Leu Tyr Leu Glu Gly
65                  70                  75                  80

Ala Glu Leu Ser Val Leu Gln Leu Asn Thr Asn Glu Arg Leu Cys Val
                85                  90                  95

Arg Phe Glu Phe Leu Ser Lys Leu Arg His His His Arg Arg Trp Arg
            100                 105                 110

Phe Thr Phe Ser His Phe Val Val Asp Pro Asp Gln Glu Tyr Glu Val
            115                 120                 125

Thr Val His His Leu Pro Lys Pro Ile Pro Asp Gly Asp Pro Asn His
        130                 135                 140

Gln Ser Lys Asn Phe Leu Val Pro Asp Cys Glu His Ala Arg Met Lys
145                 150                 155                 160

Val Thr Thr Pro Cys Met Ser Ser Gly Ser Leu Trp Asp Pro Asp Ile
                165                 170                 175

Thr Val Glu Thr Leu Glu Ala His Gln Leu Arg Val Ser Phe Thr Leu
            180                 185                 190

Trp Asn Glu Ser Thr His Tyr Gln Ile Leu Leu Thr Ser Phe Pro His
            195                 200                 205

Met Glu Asn His Ser Cys Phe Glu His Met His His Ile Pro Ala Pro
    210                 215                 220

Arg Pro Glu Glu Phe His Gln Arg Ser Asp Val Thr Leu Thr Leu Arg
225                 230                 235                 240

Asn Leu Lys Gly Cys Cys Arg His Gln Val Gln Ile Gln Pro Phe Phe
                245                 250                 255

Ser Ser Cys Leu Asn Asp Cys Leu Arg His Ser Ala Thr Val Ser Cys
                260                 265                 270

Pro
```

```
<210> SEQ ID NO 98
<211> LENGTH: 286
<212> TYPE: PRT
<213> ORGANISM: Unknown
<220> FEATURE:
<223> OTHER INFORMATION: Feline IL17Ra ECD

<400> SEQUENCE: 98
```

```
Ser Pro Arg Leu Leu Asp Tyr Pro Ala Pro Val Cys Ser Gln Gln Gly
1               5                   10                  15

Leu Asn Cys Val Val Lys Asn Ser Thr Cys Leu Asp Asp Ser Trp Ile
            20                  25                  30

His Leu Arg Asn Leu Thr Pro Ser Ser Pro Lys Asp Val Gln Val His
        35                  40                  45

Leu Asp Phe Val Gln Thr Gln His Gly Asp Leu Leu Pro Val Ala Gly
    50                  55                  60

Ile Arg Trp Thr Leu Gln Thr Asp Ala Ser Ile Leu Tyr Leu Glu Gly
65                  70                  75                  80

Ala Glu Leu Ser Val Leu Gln Leu Asn Thr Asn Glu Arg Leu Cys Val
```

```
                85                  90                  95
Lys Phe Glu Phe Leu Thr Arg Leu Lys His His His Lys Arg Trp His
            100                 105                 110
Phe Thr Phe Ser His Phe Val Val Glu Pro Gly Gln Glu Tyr Glu Val
            115                 120                 125
Thr Val His His Leu Pro Lys Pro Ile Pro Asp Gly Asp Pro Asn His
            130                 135                 140
Gln Ser Arg Asn Phe Pro Val Pro Gly Cys Glu Asp Pro Arg Met Lys
145                 150                 155                 160
Met Ile Thr Pro Cys Val Gly Ser Gly Ser Leu Trp Asp Pro Asn Ile
                165                 170                 175
Thr Val Glu Thr Leu Glu Ala Arg Gln Leu Trp Val Ser Phe Thr Leu
                180                 185                 190
Trp Asn Glu Ser Thr His Tyr Gln Ile Leu Leu Thr Ser Phe Pro His
                195                 200                 205
Thr Glu Asn His Ser Cys Phe Gln His Thr Leu Met Val Pro Glu Pro
            210                 215                 220
Ala Tyr Gln Asp Ser Arg Gln Arg Ser Asn Val Thr Leu Thr Leu Ser
225                 230                 235                 240
Asp Ser Asn Trp Cys Cys Arg His Arg Val Gln Ile Gln Pro Phe Phe
                245                 250                 255
Ser Ser Cys Leu Asn Asp Cys Leu Arg His Ser Ile Thr Val Pro Cys
                260                 265                 270
Pro Glu Ile Pro Asp Pro Pro Val Ser Ile Ala Asp Tyr Ile
            275                 280                 285

<210> SEQ ID NO 99
<211> LENGTH: 286
<212> TYPE: PRT
<213> ORGANISM: Unknown
<220> FEATURE:
<223> OTHER INFORMATION: Equine IL17Ra ECD

<400> SEQUENCE: 99

Ser Pro Arg Leu Leu Glu His Pro Ala Pro Val Cys Ser Gln Gln Gly
1               5                   10                  15
Leu Asn Cys Thr Val Lys Asn Ser Thr Cys Leu Asp Asp Ser Trp Leu
            20                  25                  30
His Pro Pro His Leu Thr Pro Ser Ser Pro Lys Asp Val Gln Ile Gln
            35                  40                  45
Leu His Phe Ala His Thr Gln Gln Gly Asp Leu Leu Pro Val Ile His
        50                  55                  60
Ile Glu Trp Thr Leu Gln Thr Asp Ala Ser Ile Leu Tyr Leu Glu Gly
65                  70                  75                  80
Ala Glu Leu Ser Val Leu Gln Leu Ser Thr Asn Glu Arg Leu Cys Val
                85                  90                  95
Thr Phe Glu Phe Leu Ser Arg Leu Lys His His His Lys Arg Trp Arg
            100                 105                 110
Phe Thr Phe Ala His Phe Val Val Glu Pro Gly Gln Glu Tyr Glu Val
            115                 120                 125
Thr Val His His Leu Pro Lys Pro Phe Pro His Gly Asp Pro Asn His
            130                 135                 140
Gln Ser Arg Asn Phe Leu Val Pro Asp Cys Met Asp Pro Arg Met Arg
145                 150                 155                 160
Ile Thr Thr Pro Cys Val Ser Ser Gly Ser Leu Trp Asp Pro Asn Ile
```

```
                165             170             175
Thr Val Glu Thr Leu Glu Ala His Arg Leu Arg Val Asp Phe Thr Leu
            180             185             190

Trp Asn Glu Ser Ala Arg Tyr Gln Ile Leu Leu Ser Ser Phe Pro His
        195             200             205

Met Glu Asn Gln Ser Cys Phe Asp Asp Val Gln Asn Ile Leu Lys His
    210             215             220

Thr Pro Glu Ala Ser His Gln Arg Ala Asn Ile Thr Leu Thr Leu Ser
225             230             235             240

Asp Phe Asn Trp Cys Cys Arg His His Val Gln Ile Gln Pro Phe Phe
            245             250             255

Ser Ser Cys Leu Asn Asp Cys Leu Arg His Thr Val Thr Val Pro Cys
        260             265             270

Pro Glu Ile Pro Asp Thr Pro Asp Ser Thr Ala Asp Tyr Met
        275             280             285

<210> SEQ ID NO 100
<211> LENGTH: 174
<212> TYPE: PRT
<213> ORGANISM: Artificial Sequence
<220> FEATURE:
<223> OTHER INFORMATION: Mouse monoclonal antibody Clone C variable
      light chain

<400> SEQUENCE: 100

Met Lys Phe Pro Ser Gln Leu Leu Leu Phe Leu Leu Phe Arg Ile Thr
1               5               10              15

Gly Ile Ile Cys Asp Ile Gln Met Thr Gln Ser Ser Ser Tyr Leu Ser
            20              25              30

Val Ser Leu Gly Gly Arg Val Thr Ile Thr Cys Lys Ala Asn Asp His
        35              40              45

Ile Asn Asn Trp Leu Ala Trp Tyr Gln Gln Lys Pro Gly Asn Ala Pro
    50              55              60

Arg Leu Leu Ile Ser Gly Ser Thr Ser Leu Glu Thr Gly Val Pro Ser
65              70              75              80

Arg Phe Ser Gly Ser Gly Ser Gly Lys Asp Tyr Thr Leu Ser Ile Thr
            85              90              95

Ser Leu Gln Thr Glu Asp Val Ala Thr Tyr Tyr Cys Gln Gln Tyr Trp
        100             105             110

Ser Thr Pro Phe Thr Phe Gly Ser Gly Thr Lys Leu Glu Ile Lys Arg
        115             120             125

Ala Asp Ala Ala Pro Thr Val Ser Ile Phe Pro Pro Ser Ser Glu Gln
    130             135             140

Leu Thr Ser Gly Gly Ala Ser Val Val Leu Gly Val Ile Met Val Ile
145             150             155             160

Ala Val Ser Cys Val Lys Leu Leu Ser Ala His Asn Ser Thr
            165             170

<210> SEQ ID NO 101
<211> LENGTH: 161
<212> TYPE: PRT
<213> ORGANISM: Artificial Sequence
<220> FEATURE:
<223> OTHER INFORMATION: Mouse monoclonal antibody Clone E variable
      light chain

<400> SEQUENCE: 101

Met Lys Leu Pro Val Arg Leu Leu Val Leu Met Phe Trp Ile Pro Ala
```

-continued

```
1               5                   10                  15

Ser Asn Ser Asp Val Val Met Thr Gln Thr Pro Leu Ser Leu Pro Val
                20                  25                  30

Ser Leu Gly Asp Gln Ala Ser Ile Ser Cys Arg Ser Ser Gln Ser Leu
            35                  40                  45

Val His Ser Asn Gly Asn Thr Tyr Phe His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Ala Pro Phe Thr Phe Gly Ser Gly Thr Lys Leu
            115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Ser Arg Ala
145                 150                 155                 160

Asn
```

```
<210> SEQ ID NO 102
<211> LENGTH: 162
<212> TYPE: PRT
<213> ORGANISM: Artificial Sequence
<220> FEATURE:
<223> OTHER INFORMATION: Mouse monoclonal antibody Clone A variable
      light chain

<400> SEQUENCE: 102
```

```
Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
                20                  25                  30

Ser Leu Gly Asp Gln Ala Ser Ile Ser Cys Arg Ser Ser Gln Ser Leu
            35                  40                  45

Val His Ser Asn Gly Asn Thr Tyr Leu His Trp Tyr Leu Gln Arg Pro
    50                  55                  60

Gly Gln Ser Pro Asn Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Phe Thr Phe Gly Ser Gly Thr Lys Leu
            115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Lys Gly
145                 150                 155                 160

Glu Phe
```

```
<210> SEQ ID NO 103
<211> LENGTH: 140
<212> TYPE: PRT
<213> ORGANISM: Artificial Sequence
```

-continued

```
<220> FEATURE:
<223> OTHER INFORMATION: Mouse monoclonal antibody Clone D variable
      light chain

<400> SEQUENCE: 103

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Tyr Arg Ala Ser Lys Ser
        35                  40                  45

Val Ser Thr Ser Gly Tyr Ser Tyr Met His Trp Asn Gln Gln Lys Pro
    50                  55                  60

Gly Gln Pro Pro Arg Leu Leu Ile Tyr Leu Val Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln His Ile Arg Glu Leu Tyr Thr Phe Gly Gly Gly Thr Lys Leu Glu
        115                 120                 125

Ile Lys Arg Ala Asp Ala Ala Pro Thr Val Ser Ile
    130                 135                 140

<210> SEQ ID NO 104
<211> LENGTH: 157
<212> TYPE: PRT
<213> ORGANISM: Artificial Sequence
<220> FEATURE:
<223> OTHER INFORMATION: Mouse monoclonal antibody Clone D variable
      heavy chain

<400> SEQUENCE: 104

Met Gly Trp Ile Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Thr Gly Ala Ser Val Lys Ile Ser Cys Lys Ala Ser Gly Tyr Ser Phe
        35                  40                  45

Thr Tyr Tyr Tyr Met His Trp Val Lys Gln Ser His Gly Lys Ser Leu
    50                  55                  60

Glu Trp Ile Gly Tyr Ile Ser Cys Phe Asn Gly Asp Thr Asn Tyr Asn
65                  70                  75                  80

Gln Glu Phe Lys Asp Lys Ala Thr Phe Thr Ala Asp Thr Ser Ser Ser
                85                  90                  95

Thr Ala Tyr Met Gln Phe Asn Ser Leu Thr Ser Glu Asp Ser Ala Val
            100                 105                 110

Tyr Tyr Cys Ala Arg Gly Leu Ser Thr Leu Ile Thr Glu Gly Trp Phe
        115                 120                 125

Ala Tyr Trp Gly Gln Gly Thr Leu Val Thr Val Ser Ala Ala Lys Thr
    130                 135                 140

Thr Pro Pro Ser Val Tyr Pro Leu Ala Pro Gly Ser Ala
145                 150                 155

<210> SEQ ID NO 105
<211> LENGTH: 174
<212> TYPE: PRT
<213> ORGANISM: Artificial Sequence
```

```
<220> FEATURE:
<223> OTHER INFORMATION: Mouse monoclonal antibody Clone C variable
     heavy chain

<400> SEQUENCE: 105

Met Asn Leu Gly Leu Ser Phe Ile Phe Leu Ala Leu Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Lys Leu Ser Cys Ala Ala Ser Gly Phe Thr Phe
        35                  40                  45

Ser Ser Tyr Gly Met Ser Trp Val Arg Gln Thr Pro Asp Lys Arg Leu
    50                  55                  60

Glu Leu Val Ala Ile Ile Asn Ser Asn Gly Gly Ser Thr Tyr Tyr Pro
65                  70                  75                  80

Asp Ser Val Lys Gly Arg Phe Thr Ile Ser Arg Asp Asn Asp Lys Asn
            85                  90                  95

Ser Leu Tyr Leu Gln Met Ser Ser Leu Lys Ser Glu Asp Thr Ala Met
        100                 105                 110

Tyr Tyr Cys Val Arg Cys His Tyr Asp Tyr Glu Arg Val Phe Asp Tyr
        115                 120                 125

Trp Gly Gln Gly Thr Thr Leu Thr Val Ser Ser Ala Lys Thr Thr Pro
    130                 135                 140

Pro Ser Val Tyr Pro Leu Ala Pro Gly Ser Ala Ala Gln Thr Asn Ser
145                 150                 155                 160

Met Val Thr Leu Gly Cys Leu Val Lys Gly Tyr Phe Pro Glu
                165                 170

<210> SEQ ID NO 106
<211> LENGTH: 172
<212> TYPE: PRT
<213> ORGANISM: Artificial Sequence
<220> FEATURE:
<223> OTHER INFORMATION: Mouse monoclonal antibody Clone A variable
     heavy chain

<400> SEQUENCE: 106

Met Ala Val Leu Gly Leu Leu Leu Cys Leu Val Thr Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Ile Ser Gly Phe Ser Leu
        35                  40                  45

Thr Ser Asn Gly Val His Trp Val Arg Gln Ser Pro Gly Lys Asp Leu
    50                  55                  60

Glu Trp Leu Val Val Ile Trp Ser Asp Gly Thr Thr Thr Tyr Asn Ser
65                  70                  75                  80

Asp Phe Lys Ser Arg Leu Ser Ile Ser Lys Asp Asn Ser Lys Ser Gln
            85                  90                  95

Val Phe Leu Lys Met Asn Ser Leu Gln Thr Asp Asp Thr Ala Met Tyr
        100                 105                 110

Tyr Cys Ala Arg His Tyr Asp Trp Gly Tyr Tyr Tyr Ala Met Asp Tyr
        115                 120                 125

Trp Gly Gln Gly Thr Ser Val Thr Val Ser Ser Ala Lys Thr Thr Pro
    130                 135                 140

Pro Ser Val Tyr Pro Leu Ala Pro Gly Ser Ala Ala Gln Thr Asn Ser
145                 150                 155                 160
```

```
Met Val Thr Leu Gly Cys Leu Val Lys Gly Glu Phe
            165                 170

<210> SEQ ID NO 107
<211> LENGTH: 172
<212> TYPE: PRT
<213> ORGANISM: Artificial Sequence
<220> FEATURE:
<223> OTHER INFORMATION: Mouse monoclonal antibody Clone E variable
      heavy chain

<400> SEQUENCE: 107

Met Ala Val Leu Gly Leu Leu Leu Cys Leu Val Thr Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Ile Ser Gly Phe Ser Leu
        35                  40                  45

Thr Ser Asn Gly Val His Trp Val Arg Gln Pro Pro Gly Lys Gly Leu
    50                  55                  60

Glu Trp Leu Val Val Ile Trp Ser Asp Gly Thr Thr Thr Tyr Asn Ser
65                  70                  75                  80

Ala Leu Lys Ser Arg Leu Ser Ile Ser Lys Asp Asn Ser Lys Ser Gln
            85                  90                  95

Val Phe Leu Lys Met Asn Ser Leu Gln Thr Asp Asp Thr Ala Met Tyr
            100                 105                 110

Tyr Cys Ala Arg His Tyr Asp Arg Gly Tyr Tyr Tyr Ala Met Asp Tyr
        115                 120                 125

Trp Gly Gln Gly Thr Ser Val Thr Val Ser Ser Ala Lys Thr Thr Pro
    130                 135                 140

Pro Ser Val Tyr Pro Leu Ala Pro Gly Ser Ala Ala Gln Thr Asn Ser
145                 150                 155                 160

Met Val Thr Leu Gly Cys Leu Val Lys Gly Glu Phe
            165                 170

<210> SEQ ID NO 108
<211> LENGTH: 7
<212> TYPE: PRT
<213> ORGANISM: Artificial Sequence
<220> FEATURE:
<223> OTHER INFORMATION: Variable light chain CDR-L2 v2 amino acid
      sequence of mouse antibody clone C

<400> SEQUENCE: 108

Gly Ser Thr Ser Leu Glu Ser
1               5

<210> SEQ ID NO 109
<211> LENGTH: 16
<212> TYPE: PRT
<213> ORGANISM: Artificial Sequence
<220> FEATURE:
<223> OTHER INFORMATION: Variable heavy chain CDR-H2 v2 amino acid
      sequence of mouse antibody clone A

<400> SEQUENCE: 109

Val Ile Trp Ser Asp Gly Thr Thr Thr Tyr Asn Ser Asp Phe Lys Ser
1               5                   10                  15

<210> SEQ ID NO 110
<211> LENGTH: 14
```

```
<212> TYPE: PRT
<213> ORGANISM: Artificial Sequence
<220> FEATURE:
<223> OTHER INFORMATION: Variable region heavy chain framework HC-FR2 v2
      amino acid sequence of mouse antibody clone A

<400> SEQUENCE: 110

Trp Val Arg Gln Ser Pro Gly Lys Asp Leu Glu Trp Leu Val
1               5                   10

<210> SEQ ID NO 111
<211> LENGTH: 15
<212> TYPE: PRT
<213> ORGANISM: Artificial Sequence
<220> FEATURE:
<223> OTHER INFORMATION: Variable light chain CDR-L1 v2 amino acid
      sequence of mouse antibody clone A

<400> SEQUENCE: 111

Ser Ser Gln Ser Leu Val His Ser Asn Gly Asn Thr Tyr Leu His
1               5                   10                  15

<210> SEQ ID NO 112
<211> LENGTH: 7
<212> TYPE: PRT
<213> ORGANISM: Artificial Sequence
<220> FEATURE:
<223> OTHER INFORMATION: Variable light chain CDR-L2 v2 amino acid
      sequence of mouse antibody clone A

<400> SEQUENCE: 112

Lys Val Ser Asn Arg Phe Ser
1               5

<210> SEQ ID NO 113
<211> LENGTH: 15
<212> TYPE: PRT
<213> ORGANISM: Artificial Sequence
<220> FEATURE:
<223> OTHER INFORMATION: Variable region light chain framework LC-FR2 v2
      amino acid sequence of mouse antibody clone A

<400> SEQUENCE: 113

Trp Tyr Leu Gln Arg Pro Gly Gln Ser Pro Asn Leu Leu Ile Tyr
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: Variable heavy chain CDR-H2 v2amino acid
      sequence of mouse antibody clone E

<400> SEQUENCE: 114

Val Ile Trp Ser Asp Gly Thr Thr Thr Tyr Asn Ser Ala Leu Lys Ser
1               5                   10                  15

<210> SEQ ID NO 115
<211> LENGTH: 14
<212> TYPE: PRT
<213> ORGANISM: Artificial Sequence
<220> FEATURE:
<223> OTHER INFORMATION: Variable region heavy chain framework HC-FR2 v2
      amino acid sequence of mouse antibody clone E

<400> SEQUENCE: 115

Trp Val Arg Gln Pro Pro Gly Lys Gly Leu Glu Trp Leu Val
```

-continued

```
1               5                  10

<210> SEQ ID NO 116
<211> LENGTH: 16
<212> TYPE: PRT
<213> ORGANISM: Artificial Sequence
<220> FEATURE:
<223> OTHER INFORMATION: Variable light chain CDR-L1 v2 amino acid
      sequence of mouse antibody clone E

<400> SEQUENCE: 116

Arg Ser Ser Gln Ser Leu Val His Ser Asn Gly Asn Thr Tyr Phe His
1               5                  10                  15

<210> SEQ ID NO 117
<211> LENGTH: 7
<212> TYPE: PRT
<213> ORGANISM: Artificial Sequence
<220> FEATURE:
<223> OTHER INFORMATION: Variable light chain CDR-L2 v2 amino acid
      sequence of mouse antibody clone E

<400> SEQUENCE: 117

Lys Val Ser Asn Arg Phe Ser
1               5

<210> SEQ ID NO 118
<211> LENGTH: 15
<212> TYPE: PRT
<213> ORGANISM: Artificial Sequence
<220> FEATURE:
<223> OTHER INFORMATION: Variable region light chain framework LC-FR2 v2
      amino acid sequence of mouse antibody clone E

<400> SEQUENCE: 118

Trp Tyr Leu Gln Lys Pro Gly Gln Ser Pro Lys Leu Leu Ile Tyr
1               5                  10                  15

<210> SEQ ID NO 119
<211> LENGTH: 17
<212> TYPE: PRT
<213> ORGANISM: Artificial Sequence
<220> FEATURE:
<223> OTHER INFORMATION: Variable heavy chain CDR-H2 v2 amino acid
      sequence of mouse antibody clone D

<400> SEQUENCE: 119

Tyr Ile Ser Cys Phe Asn Gly Asp Thr Asn Tyr Asn Gln Glu Phe Lys
1               5                  10                  15

Asp

<210> SEQ ID NO 120
<211> LENGTH: 14
<212> TYPE: PRT
<213> ORGANISM: Artificial Sequence
<220> FEATURE:
<223> OTHER INFORMATION: Variable region heavy chain framework HC-FR2 v2
      amino acid sequence of mouse antibody clone D

<400> SEQUENCE: 120

Trp Val Lys Gln Ser His Gly Lys Ser Leu Glu Trp Ile Gly
1               5                  10

<210> SEQ ID NO 121
<211> LENGTH: 15
<212> TYPE: PRT
<213> ORGANISM: Artificial Sequence
```

-continued

```
<220> FEATURE:
<223> OTHER INFORMATION: Variable light chain CDR-L1 v2 amino acid
      sequence of mouse antibody clone D

<400> SEQUENCE: 121

Arg Ala Ser Lys Ser Val Ser Thr Ser Gly Tyr Ser Tyr Met His
1               5                   10                  15

<210> SEQ ID NO 122
<211> LENGTH: 7
<212> TYPE: PRT
<213> ORGANISM: Artificial Sequence
<220> FEATURE:
<223> OTHER INFORMATION: Variable light chain CDR-L2 v2 amino acid
      sequence of mouse antibody clone D

<400> SEQUENCE: 122

Leu Val Ser Asn Leu Glu Ser
1               5

<210> SEQ ID NO 123
<211> LENGTH: 15
<212> TYPE: PRT
<213> ORGANISM: Artificial Sequence
<220> FEATURE:
<223> OTHER INFORMATION: Variable region light chain framework LC-FR2 v2
      amino acid sequence of mouse antibody clone D

<400> SEQUENCE: 123

Trp Asn Gln Gln Lys Pro Gly Gln Pro Pro Arg Leu Leu Ile Tyr
1               5                   10                  15
```

IL17A ANTIBODIES AND ANTAGONISTS FOR VETERINARY USE

CROSS-REFERENCE TO RELATED APPLICATIONS

This application is a continuation of U.S. application Ser. No. 16/621,012, filed Dec. 10, 2019, which is a national stage application of PCT/US2018/038033, filed Jun. 18, 2018, which claims the benefit of priority to U.S. Provisional Application No. 62/521,514, filed Jun. 18, 2017, each of which is expressly incorporated by reference herein in its entirety for any purpose.

FIELD

This present disclosure relates to anti-IL17A antibodies and IL17Ra ECD polypeptides for binding to IL17A, for example canine, feline, and/or equine IL17A, and methods of using the same, for example, treating IL17-induced conditions or reducing IL17 signaling function in cells, for instance in companion animals, such as canines, felines, and equines. The present disclosure also relates to IgG Fc variant polypeptides having one or more amino acid substitutions for reducing binding to C1q and/or CD16 and methods of using the same. For example, IgG Fc variants and/or polypeptides comprising the IgG Fc variants (e.g., fusion polypeptides comprising the IgG Fc variants and the anti-IL17A antibodies and/or IL17Ra ECD polypeptides described herein) may have reduced complement-mediated immune responses and/or antibody-dependent cell-mediated cytotoxicity.

BACKGROUND

Interleukin 17A (IL17A) is a homodimeric cytokine produced by T helper 17 (Th17) cells and understood to be involved in immune disorders such as plaque psoriasis, psoriatic arthritis, rheumatoid arthritis, airway inflammation, asthma, osteoarthritis, inflammatory bowel disorder, Crohn's disease, ankylosing spondylitis, atopic dermatitis, degenerative myelopathy, multiple sclerosis, and uveitis.

IL17A is understood to function by binding its receptor IL17Ra and activating downstream pathways, such as activation of NFxB, MAPKs, and C/EBPs to induce production of cytokines and chemokines, and induce host defense to microbial infection.

Companion animals such as cats, dogs, and horses suffer from many diseases similar to human diseases. There remains a need for methods and compounds that can be used specifically to bind companion animal IL17A for treating IL17A-induced conditions and for reducing IL17A signaling.

SUMMARY

Embodiment 1. An isolated antibody that binds to canine IL17A, wherein the antibody binds to an epitope within amino acids 65 to 88 of SEQ ID NO: 22. Embodiment 2. The antibody of embodiment 1, wherein the antibody binds to an epitope comprising or within the amino acid sequence of SEQ ID NO: 23 or SEQ ID NO: 51. Embodiment 3. The antibody of embodiment 1 or embodiment 2, wherein the antibody binds to canine IL17A with a dissociation constant ($K_d$) of less than $5\times10^{-6}$ M, less than $1\times10^{-6}$ M, less than $5\times10^{-7}$ M, less than $1\times10^{-7}$ M, less than $5\times10^{-8}$ M, less than $1\times10^{-8}$ M, less than $5\times10^{-9}$ M, less than $1\times10^{-9}$ M, less than $5\times10^{-10}$ M, less than $1\times10^{-10}$ M, less than $5\times10^{-11}$ M, less than $1\times10^{-11}$ M, less than $5\times10^{-12}$ M, or less than $1\times10^{-12}$ M, as measured by biolayer interferometry.

Embodiment 4. The antibody of any one of embodiments 1 to 3, wherein the antibody reduces IL17A signaling function in a companion animal species, as measured by a reduction in I1L6 secretion in a cell-based assay.

Embodiment 5. The antibody of embodiment 4, wherein the companion animal species is canine, feline, or equine.

Embodiment 6. The antibody of any one of embodiments 1 to 5, wherein the antibody binds to feline IL17A or equine IL17A as determined by immunoblot analysis or biolayer interferometry.

Embodiment 7. The antibody of any one of embodiments 1 to 6, wherein the antibody competes with monoclonal Clone A, monoclonal Clone C, or monoclonal Clone E antibody in binding to canine IL17A.

Embodiment 8. The antibody of any one of embodiments 1 to 6, wherein the antibody competes with monoclonal Clone A, monoclonal Clone C, or monoclonal Clone E antibody in binding to feline IL17A or in binding to equine IL17A.

Embodiment 9. The antibody of any one of embodiments 1 to 8, wherein the antibody is a monoclonal antibody.

Embodiment 10. The antibody of any one of embodiments 1 to 9, wherein the antibody is a canine, a caninized, a feline, a felinized, an equine, an equinized, or a chimeric antibody.

Embodiment 11. The antibody of any one of embodiments 1 to 10, wherein the antibody is a chimeric antibody comprising murine variable heavy chain framework regions or murine variable light chain framework regions.

Embodiment 12. The antibody of any one of embodiments 1 to 11, comprising a heavy chain and a light chain, wherein:
  a. (i) the heavy chain comprises a CDR-H1 sequence having at least 85%, at least 90%, at least 95, or at least 98% sequence identity to the amino acid sequence of the amino acid sequence of SEQ ID NO: 1, a CDR-H2 sequence having at least 85%, at least 90%, at least 95, or at least 98% sequence identity to the amino acid sequence of the amino acid sequence of SEQ ID NO: 2, and a CDR-H3 sequence having at least 85%, at least 90%, at least 95, or at least 98% sequence identity to the amino acid sequence of the amino acid sequence of SEQ ID NO: 3, and
  b. (ii) the light chain comprises a CDR-L1 sequence having at least 85%, at least 90%, at least 95, or at least 98% sequence identity to the amino acid sequence of the amino acid sequence of SEQ ID NO: 8, a CDR-L2 sequence having at least 85%, at least 90%, at least 95, or at least 98% sequence identity to the amino acid sequence of the amino acid sequence of SEQ ID NO: 9 or SEQ ID NO: 108, and a CDR-L3 sequence having at least 85%, at least 90%, at least 95, or at least 98% sequence identity to the amino acid sequence of the amino acid sequence of SEQ ID NO: 10; or
  c. (i) the heavy chain comprises a CDR-H1 sequence having at least 85%, at least 90%, at least 95, or at least 98% sequence identity to the amino acid sequence of the amino acid sequence of SEQ ID NO: 52, a CDR-H2 sequence having at least 85%, at least 90%, at least 95, or at least 98% sequence identity to the amino acid sequence of the amino acid sequence of SEQ ID NO: 53 or SEQ ID NO: 109, and a CDR-H3 sequence having at least 85%, at least 90%, at least 95, or at least 98% sequence identity to the amino acid sequence of SEQ ID SEQ ID NO: 54, and d. (ii) the light chain comprises a CDR-L1 sequence having at least 85%, at least 90%, at least 95, or at least 98% sequence identity to the amino acid sequence of the amino acid sequence of SEQ ID NO: 59 or SEQ ID NO: 111, a CDR-L2 sequence having at least 85%, at least 90%, at least 95, or at least 98% sequence identity to the amino acid sequence of the amino acid sequence of SEQ ID NO: 60 or SEQ ID NO: 112, and a CDR-L3 sequence having at least 85%, at least 90%, at least 95, or at least 98% sequence identity to the amino acid sequence of the amino acid sequence of SEQ ID NO: 61; or e. (i) the heavy chain comprises a CDR-H1 sequence having at least 85%, at least 90%, at least 95, or at least 98% sequence identity to the amino acid sequence of the amino acid sequence of SEQ ID NO: 66, a CDR-H2 sequence having at least 85%, at least 90%, at least 95, or at least 98% sequence identity to the amino acid sequence of the amino acid sequence of SEQ ID NO: 67 or SEQ ID NO: 114, and a CDR-H3 sequence having at least 85%, at least 90%, at least 95, or at least 98% sequence identity to the amino acid sequence of the amino acid sequence of SEQ ID NO: 68, and f. (ii) the light chain comprises a CDR-L1 sequence having at least 85%, at least 90%, at least 95, or at least 98% sequence identity to the amino acid sequence of the amino acid sequence of SEQ ID NO: 73 or SEQ ID NO: 116, a CDR-L2 sequence having at least 85%, at least 90%, at least 95, or at least 98% sequence identity to the amino acid sequence of the amino acid sequence of SEQ ID NO: 74 or SEQ ID NO: 117; and a CDR-L3 sequence having at least 85%, at least 90%, at least 95, or at least 98% sequence identity to the amino acid sequence of the amino acid sequence of SEQ ID NO: 75.

Embodiment 13. The antibody of any one of embodiments 1 to 12, comprising a heavy chain and a light chain, wherein:

a. (i) the heavy chain comprises a CDR-H1 sequence having the amino acid sequence of SEQ ID NO: 1, a CDR-H2 sequence having the amino acid sequence of SEQ ID NO: 2, and a CDR-H3 sequence having the amino acid sequence of SEQ ID NO: 3, and b. (ii) the light chain comprises a CDR-L1 sequence having the amino acid sequence of SEQ ID NO: 8, a CDR-L2 sequence having the amino acid sequence of SEQ ID NO: 9 or SEQ ID NO: 108, and a CDR-L3 sequence having the amino acid sequence of SEQ ID NO: 10; or c. (i) the heavy chain comprises a CDR-H1 sequence having the amino acid sequence of SEQ ID NO: 52, a CDR-H2 sequence having the amino acid sequence of SEQ ID NO: 53 or SEQ ID NO: 109, and a CDR-H3 sequence having the amino acid sequence of SEQ ID SEQ ID NO: 54, and d. (ii) the light chain comprises a CDR-L1 sequence having the amino acid sequence of SEQ ID NO: 59 or SEQ ID NO: 111, a CDR-L2 sequence having the amino acid sequence of SEQ ID NO: 60 or SEQ ID NO: 112, and a CDR-L3 sequence having the amino acid sequence of SEQ ID NO: 61; or e. (i) the heavy chain comprises a CDR-H1 sequence having the amino acid sequence of SEQ ID NO: 66, a CDR-H2 sequence having the amino acid sequence of SEQ ID NO: 67 or SEQ ID NO: 114, and a CDR-H3 sequence having the amino acid sequence of SEQ ID NO: 68, and f. (ii) the light chain comprises a CDR-L1 sequence having the amino acid sequence of SEQ ID NO: 73 or SEQ ID NO: 116, a CDR-L2 sequence having the amino acid sequence of SEQ ID NO: 74 or SEQ ID NO: 117; and a CDR-L3 sequence having the amino acid sequence of SEQ ID NO: 75.

Embodiment 14. The antibody of embodiment 12 or embodiment 13, further comprising:

a. one or more of (i) a variable region heavy chain framework 1 (HC-FR1) sequence of SEQ ID NO: 4; (ii) a HC-FR2 sequence of SEQ ID NO: 5; (iii) a HC-FR3 sequence of SEQ ID NO: 6; (iv) a HC-FR4 sequence of SEQ ID NO: 7; (v) a variable region light chain framework 1 (LC-FR1) sequence of SEQ ID NO: 11; (vi) an LC-FR2 sequence of SEQ ID NO: 12; (vii) an LC-FR3 sequence of SEQ ID NO: 13; and/or (vii) an LC-FR4 sequence of SEQ ID NO: 14; or b. one or more of (i) a variable region heavy chain framework 1 (HC-FR1) sequence of SEQ ID NO: 55; (ii) a HC-FR2 sequence of SEQ ID NO: 56 or SEQ ID NO: 110; (iii) a HC-FR3 sequence of SEQ ID NO: 57; (iv) a HC-FR4 sequence of SEQ ID NO: 58; (v) a variable region light chain framework 1 (LC-FR1) sequence of SEQ ID NO: 62; (vi) an LC-FR2 sequence of SEQ ID NO: 63 or SEQ ID NO: 113; (vii) an LC-FR3 sequence of SEQ ID NO: 64; and/or (vii) an LC-FR4 sequence of SEQ ID NO: 65; or c. one or more of (i) a variable region heavy chain framework 1 (HC-FR1) sequence of SEQ ID NO: 69; (ii) a HC-FR2 sequence of SEQ ID NO: 70 or SEQ ID NO: 115; (iii) a HC-FR3 sequence of SEQ ID NO: 71; (iv) a HC-FR4 sequence of SEQ ID NO: 72; (v) a variable region light chain framework 1 (LC-FR1) sequence of SEQ ID NO: 76; (vi) an LC-FR2 sequence of SEQ ID NO: 77 or SEQ ID NO: 118; (vii) an LC-FR3 sequence of SEQ ID NO: 78; and/or (vii) an LC-FR4 sequence of SEQ ID NO: 79.

Embodiment 15. The antibody of any one of embodiments 1 to 14, wherein the antibody comprises:

a. (i) a variable light chain sequence having at least 85%, at least 90%, at least 95%, or at least 98% sequence identity to the amino acid sequence of SEQ ID NO: 24; (ii) a variable heavy chain sequence having at least 85%, at least 90%, at least 95%, or at least 98% sequence identity to the amino acid sequence of SEQ ID NO: 25; or (iii) a variable light chain sequence as in (i) and a variable heavy chain sequence as in (ii); or b. (i) a variable light chain sequence having at least 85%, at least 90%, at least 95%, or at least 98% sequence identity to the amino acid sequence of SEQ ID NO: 16; (ii) a variable heavy chain sequence having at least 85%, at least 90%, at least 95%, or at least 98% sequence identity to the amino acid sequence of SEQ ID NO: 15; or (iii) a variable light chain sequence as in (i) and a variable heavy chain sequence as in (ii); or c. (i) a variable light chain sequence having at least 85%, at least 90%, at least 95%, or at least 98% sequence identity to the amino acid sequence of SEQ ID NO: 34; (ii) a variable heavy chain sequence having at least 85%, at least 90%, at least 95%, or at least 98% sequence identity to the amino acid sequence of SEQ ID NO: 35; or (iii) a variable light chain sequence as in (i) and a variable heavy chain sequence as in (ii); or d. (i) a variable light chain sequence having at least 85%, at least 90%, at least 95%, or at least 98% sequence identity to the amino acid sequence of SEQ ID NO: 38; (ii) a variable heavy chain sequence having at least 85%, at least 90%, at least 95%, or at least 98% sequence identity to the amino acid sequence of SEQ ID NO: 39; or (iii) a variable light chain sequence as in (i) and a variable heavy chain sequence as in (ii).

Embodiment 16. The antibody of any one of embodiments 1 to 15, wherein the antibody comprises a variable light chain sequence of SEQ ID NO: 24; SEQ ID NO: 16; SEQ ID NO: 34; or SEQ ID NO: 38.

Embodiment 17. The antibody of any one of embodiments 1 to 16, wherein the antibody comprises a variable heavy chain sequence of SEQ ID NO: 25, SEQ ID NO: 15; SEQ ID NO: 35; or SEQ ID NO: 39.

Embodiment 18. The antibody of any one of embodiments 1 to 17, wherein the antibody comprises:

a. a variable light chain sequence of SEQ ID NO: 24 and a variable heavy chain sequence of SEQ ID NO: 25; or b. a variable light chain sequence of SEQ ID NO: 16 and a variable heavy chain sequence of SEQ ID NO: 15; or c. a variable light chain sequence of SEQ ID NO: 34 and a variable heavy chain sequence of SEQ ID NO: 35; or d. a variable light chain sequence of SEQ ID NO: 38 and a variable heavy chain sequence of SEQ ID NO: 39.

Embodiment 19. The antibody of any one of embodiments 1 to 18, wherein the antibody comprises a constant heavy chain region or constant light chain region derived from a companion animal.

Embodiment 20. The antibody of any one of embodiments 1 to 19, wherein the antibody comprises (a) a canine heavy chain constant region selected from an IgG-A, IgG-B, IgG-C, and IgG-D constant region; (b) a feline heavy chain constant region selected from an IgG-1a, IgG-1b, and IgG-2 constant region; or (c) an equine heavy chain constant region selected from an IgG-1, IgG-2, IgG-3, IgG-4, IgG-5, IgG-6, and IgG-7 constant region.

Embodiment 21. The antibody of any one of embodiments 1 to 20, wherein the antibody comprises a heavy chain amino acid sequence of SEQ ID NO: 17, SEQ ID NO: 18, SEQ ID NO: 19, SEQ ID NO: 20, or SEQ ID NO: 27.

Embodiment 22. The antibody of any one of embodiments 1 to 21, wherein the antibody comprises a light chain amino acid sequence of SEQ ID NO: 21 or SEQ ID NO: 26.

Embodiment 23. An isolated antibody that binds to feline IL17A, wherein the antibody binds to feline IL17A with a dissociation constant ($K_d$) of less than $5 \times 10^{-6}$ M, less than $1 \times 10^{-6}$ M, less than $5 \times 10^{-7}$ M, less than $1 \times 10^{-7}$ M, less than $5 \times 10^{-8}$ M, less than $1 \times 10^{-8}$ M, less than $5 \times 10^{-9}$ M, less than $1 \times 10^{-9}$ M, less than $5 \times 10^{-10}$ M, less than $1 \times 10^{-10}$ M, less than $5 \times 10^{-11}$ M, less than $1 \times 10^{-11}$ M, less than $5 \times 10^{-12}$ M, or less than $1 \times 10^{-12}$ M, as measured by biolayer interferometry.

Embodiment 24. The antibody of embodiment 23, wherein the antibody reduces IL17A signaling function in a companion animal species, as measured by a reduction in IL6 secretion in a cell-based assay.

Embodiment 25. The antibody of embodiment 24, wherein the companion animal species is canine, feline, or equine.

Embodiment 26. The antibody of any one of embodiments 23 to 25, wherein the antibody binds to canine IL17A or equine IL17A as determined by immunoblot analysis or biolayer interferometry.

Embodiment 27. The antibody of any one of embodiments 23 to 26, wherein the antibody competes with monoclonal Clone D in binding to feline IL17A.

Embodiment 28. The antibody of any one of embodiments 23 to 27, wherein the antibody competes with monoclonal Clone D in binding to canine IL17A or in binding to equine IL17A.

Embodiment 29. The antibody of any one of embodiments 23 to 28, wherein the antibody is a monoclonal antibody.

Embodiment 30. The antibody of any one of embodiments 23 to 29, wherein the antibody is a canine, a caninized, a feline, a felinized, an equine, an equinized, or a chimeric antibody.

Embodiment 31. The antibody of any one of embodiments 23 to 30, wherein the antibody is a chimeric antibody comprising murine variable heavy chain framework regions or murine variable light chain framework regions.

Embodiment 32. The antibody of any one of embodiments 23 to 31, comprising a heavy chain and a light chain, wherein:

a. the heavy chain comprises a CDR-H1 sequence having at least 85%, at least 90%, at least 95, or at least 98% sequence identity to the amino acid sequence of the amino acid sequence of SEQ ID NO: 80, a CDR-H2 sequence having at least 85%, at least 90%, at least 95, or at least 98% sequence identity to the amino acid sequence of the amino acid sequence of SEQ ID NO: 81 or SEQ ID NO: 119, and a CDR-H3 sequence having at least 85%, at least 90%, at least 95, or at least 98% sequence identity to the amino acid sequence of the amino acid sequence of SEQ ID NO: 82, and b. the light chain comprises a CDR-L1 sequence having at least 85%, at least 90%, at least 95, or at least 98% sequence identity to the amino acid sequence of the amino acid sequence of SEQ ID NO: 87 or SEQ ID NO: 121, a CDR-L2 sequence having at least 85%, at least 90%, at least 95, or at least 98% sequence identity to the amino acid sequence of the amino acid sequence of SEQ ID NO: 88 or SEQ ID NO: 122, and a CDR-L3 sequence having at least 85%, at least 90%, at least 95, or at least 98% sequence identity to the amino acid sequence of the amino acid sequence of SEQ ID NO: 89.

Embodiment 33. The antibody of any one of embodiments 23 to 32, comprising a heavy chain and a light chain, wherein:

a. the heavy chain comprises a CDR-H1 sequence having the amino acid sequence of SEQ ID NO: 80, a CDR-H2 sequence having the amino acid sequence of SEQ ID NO: 81 or SEQ ID NO: 119, and a CDR-H3 sequence having the amino acid sequence of SEQ ID NO: 82, and b. the light chain comprises a CDR-L1 sequence having the amino acid sequence of SEQ ID NO: 87 or SEQ ID NO: 121, a CDR-L2 sequence having the amino acid sequence of SEQ ID NO: 88 or SEQ ID NO: 122, and a CDR-L3 sequence having the amino acid sequence of SEQ ID NO: 89.

Embodiment 34. The antibody of embodiment 32 or embodiment 33, further comprising one or more of (a) a variable region heavy chain framework 1 (HC-FR1) sequence of SEQ ID NO: 83; (b) a HC-FR2 sequence of SEQ ID NO: 84 or SEQ ID NO: 120; (c) a HC-FR3 sequence of SEQ ID NO: 85; (d) a HC-FR4 sequence of SEQ ID NO: 86; (e) a variable region light chain framework 1 (LC-FR1) sequence of SEQ ID NO: 90; (f) an LC-FR2 sequence of SEQ ID NO: 91 or SEQ ID NO: 123; (g) an LC-FR3 sequence of SEQ ID NO: 92; and/or (h) an LC-FR4 sequence of SEQ ID NO: 93.

Embodiment 35. The antibody of any one of embodiments 23 to 34, wherein the antibody comprises (a) a variable light chain sequence having at least 85%, at least 90%, at least 95%, or at least 98% sequence identity to the amino acid sequence of SEQ ID NO: 36; (b) a variable heavy chain sequence having at least 85%, at least 90%, at least 95%, or at least 98% sequence identity to the amino acid sequence of SEQ ID NO: 37; or (c) a variable light chain sequence as in (a) and a variable heavy chain sequence as in (b).

Embodiment 36. The antibody of any one of embodiments 23 to 35, wherein the antibody comprises (i) a variable light chain sequence of SEQ ID NO: 36, (ii) a variable heavy chain sequence of SEQ ID NO: 37; or (iii) a variable light chain sequence of SEQ ID NO: 36 and a variable heavy chain sequence of SEQ ID NO: 37.

Embodiment 37. The antibody of any one of embodiments 23 to 36, wherein the antibody comprises a constant heavy chain region or constant light chain region derived from a companion animal.

Embodiment 38. The antibody of any one of embodiments 23 to 37, wherein the antibody comprises (a) a canine heavy chain constant region selected from an IgG-A, IgG-B, IgG-C, and IgG-D constant region; (b) a feline heavy chain constant region selected from an IgG-1a, IgG-1b, and IgG-2 constant region; or (c) an equine heavy chain constant region selected from an IgG-1, IgG-2, IgG-3, IgG-4, IgG-5, IgG-6, and IgG-7 constant region.

Embodiment 39. The antibody of any one of embodiments 1 to 38, wherein the antibody is an antibody fragment, such as an Fv, scFv, Fab, Fab', F(ab')2, or Fab'-SH fragment. Embodiment 40. The antibody of any one of embodiments 1 to 39, wherein the antibody is bi-specific, wherein the antibody binds to IL17A and one or more antigens selected from other members of IL17, IL31, TNFα, CD20, CD19, CD25, IL4, IL13, IL23, IgE, CD11a, IL6R, α4-Intergrin, IL12, IL1β, or BlyS.

Embodiment 41. An isolated nucleic acid encoding the antibody of any one of embodiments 1 to 40.

Embodiment 42. A host cell comprising the nucleic acid of embodiment 41.

Embodiment 43. A method of producing an antibody comprising culturing the host cell of embodiment 42 and isolating the antibody.

Embodiment 44. A pharmaceutical composition comprising the antibody of any one of embodiments 1 to 40 and a pharmaceutically acceptable carrier.

Embodiment 45. A method of treating a companion animal species having an IL17A-induced condition, the method comprising administering to the companion animal species a therapeutically effective amount of the antibody of any one of embodiments 1 to 40 or the pharmaceutical composition of embodiment 45.

Embodiment 46. The method of embodiment 45, wherein the companion animal species is canine, feline, or equine.

Embodiment 47. The method of embodiment 45 or 46, wherein the IL17A-induced condition is plaque psoriasis, psoriatic arthritis, rheumatoid arthritis, airway inflammation, asthma, osteoarthritis, inflammatory bowel disorder, Crohn's disease, ankylosing spondylitis, atopic dermatitis, degenerative myelopathy, multiple sclerosis, or uveitis.

Embodiment 48. The method of any one of embodiments 45 to 47, wherein the antibody or the pharmaceutical composition is administered parenterally.

Embodiment 49. The method of any one of embodiments 45 to 48, wherein the antibody or the pharmaceutical composition is administered by an intramuscular route, an intraperitoneal route, an intracerebrospinal route, a subcutaneous route, an intra-arterial route, an intrasynovial route, an intrathecal route, or an inhalation route.

Embodiment 50. The method of any one of embodiments 45 to 49, wherein the method comprises administering in combination with the antibody or the pharmaceutical composition a NFκB inhibitor, a MAPK inhibitor, and/or a C/EBP inhibitor.

Embodiment 51. The method of any one of embodiments 45 to 50, wherein the method comprises administering in combination with the antibody or the pharmaceutical composition one or more antibodies selected from an anti-IL17A antibody, an anti-TNFα antibody, an anti-CD20 antibody, an anti-IL31 antibody, an anti-CD19 antibody, an anti-CD25 antibody, an anti-IL4 antibody, an anti-IL13 antibody, an anti-IL23 antibody, an anti-IgE antibody, an anti-CD11α antibody, anti-IL6R antibody, anti-α4-Intergrin antibody, an anti-IL12 antibody, an anti-IL1β antibody, and an anti-BlyS antibody.

Embodiment 52. A method of reducing IL17A signaling function in a cell, the method comprising exposing to the cell the antibody of any one of embodiments 1 to 40 or the pharmaceutical composition of embodiment 45 under conditions permissive for binding of the antibody to extracellular IL17A, thereby reducing binding to IL17A receptor and/or reducing IL17A signaling function by the cell.

Embodiment 53. The method of embodiment 52, wherein the cell is exposed to the antibody or the pharmaceutical composition ex vivo.

Embodiment 54. The method of embodiment 52, wherein the cell is exposed to the antibody or the pharmaceutical composition in vivo.

Embodiment 55. The method of embodiment 42, 43, or 44, wherein the cell is a canine cell, a feline cell, or an equine cell.

Embodiment 56. A method for detecting IL17A in a sample from a companion animal species comprising contacting the sample with the antibody of any one of embodiments 1 to 40 or the pharmaceutical composition of embodiment 45 under conditions permissive for binding of the antibody to IL17A, and detecting whether a complex is formed between the antibody and IL17A in the sample.

Embodiment 57. The method of embodiment 56, wherein the sample is a biological sample obtained from a canine, a feline, or an equine.

Embodiment 58. A polypeptide comprising an extracellular domain of an IL17A receptor (IL17Ra) polypeptide comprising the amino acid sequence of SEQ ID NO: 94, SEQ ID NO: 97, SEQ ID NO: 98, or SEQ ID NO: 99.

Embodiment 59. The polypeptide of embodiment 58 comprising the amino acid sequence of SEQ ID NO: 33.

Embodiment 60. The polypeptide of embodiment 58 or embodiment 59, wherein the IL17Ra polypeptide comprises an IgG Fc.

Embodiment 61. The polypeptide of any one of embodiments 58 to 60, wherein the IgG Fc is a. a human IgG1 Fc, IgG2 Fc, IgG3 Fc, or IgG4 Fc;

b. a canine IgG-A Fc, IgG-B Fc, IgG-C Fc, or IgG-D Fc;

c. a feline IgG1a Fc, IgG1b Fc, or IgG2 Fc; or d. an equine IgG1 Fc, IgG2 Fc, IgG3 Fc, IgG4 Fc, IgG5 Fc, IgG6 Fc, or IgG7 Fc.

Embodiment 62. The polypeptide of any one of embodiments 58 to 61, wherein the IL17Ra polypeptide comprises the amino acid sequence of SEQ ID NO: 40, SEQ ID NO: 41, SEQ ID NO: 42, SEQ ID NO: 43, or SEQ ID NO: 44.

Embodiment 63. An isolated nucleic acid encoding the polypeptide of embodiment 58 or embodiment 59.

Embodiment 64. A host cell comprising the nucleic acid of embodiment 60.

Embodiment 65. A method of producing a polypeptide comprising culturing the host cell of embodiment and isolating the polypeptide.

Embodiment 66. A pharmaceutical composition comprising the polypeptide of embodiment 58 or embodiment 59 and a pharmaceutically acceptable carrier.

Embodiment 67. A method of treating a companion animal species having an IL17A-induced condition, the method comprising administering to the subject a therapeutically effective amount of the polypeptide of embodiment 58 or embodiment 59, or the pharmaceutical composition of embodiment 63.

Embodiment 68. The method of embodiment 64, wherein the polypeptide or pharmaceutical composition is administered parenterally.

Embodiment 69. The method of embodiment 64 or embodiment 65, wherein the polypeptide or pharmaceutical composition is administered by an intramuscular route, an intraperitoneal route, an intracerebrospinal route, a subcutaneous route, an intra-arterial route, an intrasynovial route, an intrathecal route, or an inhalation route.

Embodiment 70. The method of any one of embodiments 64 to 66, wherein the companion animal species is feline, canine, or equine.

Embodiment 71. The method of any one of embodiments 64 to 67, wherein the IL17A-induced condition is plaque psoriasis, psoriatic arthritis, rheumatoid arthritis, airway inflammation, asthma, osteoarthritis, inflammation bowel disorder, Crohn's disease, ankylosing spondylitis, atopic dermatitis, degenerative myelopathy, multiple sclerosis, or uveitis.

Embodiment 72. A polypeptide comprising an IgG Fc variant polypeptide comprising at least one amino acid substitution relative to a IgG Fc wild-type polypeptide derived from a companion animal species, wherein the IgG Fc variant polypeptide has reduced binding to C1q and/or CD16 relative to the IgGFc wild-type polypeptide.

Embodiment 73. The polypeptide of embodiment 72, wherein the IgG Fc variant polypeptide binds to C1q and/or CD16 with a dissociation constant ($K_d$) of less than $5 \times 10^{-6}$ M, less than $1 \times 10^{-6}$ M, less than $5 \times 10^{-7}$ M, less than $1 \times 10^{-7}$ M, less than $5 \times 10^{-8}$ M, less than $1 \times 10^{-8}$ M, less than $5 \times 10^{-9}$ M, less than $1 \times 10^{-9}$ M, less than $5 \times 10^{-10}$ M, less than $1 \times 10^{-10}$ M, less than $5 \times 10^{-11}$ M, less than $1 \times 10^{-11}$ M, less than $5 \times 10^{-12}$ M, or less than $1 \times 10^{-12}$ M, as measured by biolayer interferometry.

Embodiment 74. The polypeptide of embodiment 72 or embodiment 73, wherein the companion animal species is canine, feline, or equine.

Embodiment 75. The polypeptide of any one of embodiments 72 to 74, wherein the wild-type IgG Fc polypeptide is a canine IgG-B Fc or canine IgG-C Fc.

Embodiment 76. The polypeptide of any one of embodiments 72 to 75, wherein the IgG Fc variant polypeptide comprises an amino acid substitution at a position corresponding to position 110 of SEQ ID NO: 45 or at a position corresponding to position 108 of SEQ ID NO: 46.

Embodiment 77. The polypeptide of any one of embodiments 72 to 76, wherein the IgG Fc variant polypeptide comprises an amino acid substitution at a position corresponding to position 55 of SEQ ID NO: 45 or at a position corresponding to position 43 of SEQ ID NO: 46.

Embodiment 78. The polypeptide of any one of embodiments 72 to 77, wherein the IgG Fc variant polypeptide comprises an amino acid substitution at a position corresponding to position 114 of SEQ ID NO: 45 or at a position corresponding to position 112 of SEQ ID NO: 46.

Embodiment 79. The polypeptide of any one of embodiments 72 to 78, wherein the IgG Fc variant polypeptide comprises an amino acid substitution at a position corresponding to position 115 at SEQ ID NO: 45 or at a position corresponding to position 113 of SEQ ID NO: 46.

Embodiment 80. The polypeptide of any one of embodiments 72 to 79, wherein the IgG Fc variant polypeptide comprises an amino acid substitution at position 110 of SEQ ID NO: 45 or at position 108 of SEQ ID NO: 46.

Embodiment 81. The polypeptide of any one of embodiments 72 to 80, wherein the IgG Fc variant polypeptide comprises an amino acid substitution at position 55 of SEQ ID NO: 45 or at position 43 of SEQ ID NO: 46.

Embodiment 82. The polypeptide of any one of embodiments 72 to 81, wherein the IgG Fc variant polypeptide comprises an amino acid substitution at position 114 of SEQ ID NO: 45 or at position 112 of SEQ ID NO: 46.

Embodiment 83. The polypeptide of any one of embodiments 72 to 82, wherein the IgG Fc variant polypeptide comprises an amino acid substitution at position 115 at SEQ ID NO: 45 or at position 113 of SEQ ID NO: 46.

Embodiment 84. The polypeptide of any one of embodiments 72 to 83, wherein the IgG Fc variant polypeptide comprises an arginine at position 110 of SEQ ID NO: 45 or at position 108 of SEQ ID NO: 46.

Embodiment 85. The polypeptide of any one of embodiments 72 to 84, wherein the IgG Fc variant polypeptide comprises a glycine at position 55 of SEQ ID NO: 45 or at position 43 of SEQ ID NO: 46.

Embodiment 86. The polypeptide of any one of embodiments 72 to 85, wherein the IgG Fc variant polypeptide comprises an isoleucine at position 114 of SEQ ID NO: 45 or at position 112 of SEQ ID NO: 46.

Embodiment 87. The polypeptide of any one of embodiments 72 to 86, wherein the IgG Fc variant polypeptide comprises a glycine at position 115 at SEQ ID NO: 45 or at position 113 of SEQ ID NO: 46.

Embodiment 88. The polypeptide of any one of embodiments 72 to 87 comprising the amino acid sequence of SEQ ID NO: 47, SEQ ID NO: 48, SEQ ID NO: 49, or SEQ ID NO: 50.

Embodiment 89. The polypeptide of any one of embodiments 72 to 88, wherein the at least one amino acid substitution comprises an amino acid substitution with an amino acid derivative.

Embodiment 90. The polypeptide of any one of embodiments 72 to 89, wherein the polypeptide is an antibody, an antibody fragment, or a fusion polypeptide.

Embodiment 91. The polypeptide of any one of embodiments 72 to 90, wherein the polypeptide comprises the amino acid sequence of SEQ ID NO: 96.

Embodiment 92. The polypeptide of any one of embodiments 72 to 90, wherein the polypeptide comprises the antibody of any one of embodiments 1 to 40 or the polypeptide of any one of embodiments 58 to 62.

Embodiment 93. An isolated nucleic acid encoding the polypeptide of any one of embodiments 72 to 92.

Embodiment 94. A host cell comprising the nucleic acid of embodiment 93.

Embodiment 95. A method of producing a polypeptide comprising culturing the host cell of embodiment 94 and isolating the polypeptide.

Embodiment 96. A pharmaceutical composition comprising the polypeptide of any one of embodiments 72 to 92 and a pharmaceutically acceptable carrier.

Embodiment 97. A method of delivering a polypeptide to a subject comprising administering the polypeptide of any one of embodiments 72 to 92 or the pharmaceutical composition of embodiment 96 parenterally.

Embodiment 98. The method of embodiment 97 comprising administering the polypeptide or the pharmaceutical composition by an intramuscular route, an intraperitoneal route, an intracerebrospinal route, a subcutaneous route, an intra-arterial route, an intrasynovial route, an intrathecal route, or an inhalation route.

Embodiment 99. The method of embodiment 97 or embodiment 98, wherein the species is human.

Embodiment 100. The method of embodiment 97 or embodiment 98, wherein the species is a companion animal species.

Embodiment 101. The method of embodiment 100, wherein the companion animal species is canine, equine, or feline.

BRIEF DESCRIPTION OF THE DRAWINGS

FIGS. 2A-2B show the amino acid sequence alignment of variable light chain (A) and variable heavy chain (B) sequences of Clone D, C, A, and E mouse monoclonal antibodies.

DESCRIPTION OF THE SEQUENCES

Figure 1:
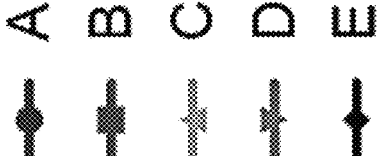
FIG. 1 shows a canine IL17A binding ELISA of Clone A, B, C, D, and E mouse monoclonal antibodies.

Table 1 provides a listing of certain sequences referenced herein.

| SEQ ID NO: | SEQUENCE | DESCRIPTION |
|---|---|---|
| | Description of the Sequences | |
| 1 | GFTFSSYGMS | Variable heavy chain CDR-H1 amino acid sequence of mouse antibody clone C |
| 2 | IINSNGGSTYYPDSVKG | Variable heavy chain CDR-H2 amino acid sequence of mouse antibody clone C |
| 3 | CHYDYERVFDY | Variable heavy chain CDR-H3 amino acid sequence of mouse antibody clone C |
| 4 | EVQLVESGGGLVQPGGSLKLSCAAS | Variable region heavy chain framework HC-FR1 amino acid sequence of mouse antibody clone C |
| 5 | WVRQTPDKRLELVA | Variable region heavy chain framework HC-FR2 amino acid sequence of mouse antibody clone C |
| 6 | RFTISRDNDKNSLYLQMSSLKSEDTAMYYCVR | Variable region heavy chain framework HC-FR3 amino acid sequence of mouse antibody clone C |
| 7 | WGQGTTLTVSS | Variable region heavy chain framework HC-FR4 amino acid sequence of mouse antibody clone C |
| 8 | KANDHINNWLA | Variable light chain CDR-L1 amino acid sequence of mouse antibody clone C |
| 9 | GSTSLET | Variable light chain CDR-L2 amino acid sequence of mouse antibody clone C |

-continued

| | Description of the Sequences | |
|---|---|---|

| SEQ ID NO: | SEQUENCE | DESCRIPTION |
|---|---|---|
| 108 | GSTSLES | Variable light chain CDR-L2 v2 amino acid sequence |
| 10 | QQYWSTPFT | Variable light chain CDR-L3 amino acid sequence of mouse antibody clone C |
| 11 | DIQMTQSSSYLSVSLGGRVTITC | Variable region light chain framework LC-FR1 amino acid sequence of mouse antibody clone C1 |
| 12 | WYQQKPGNAPRLLIS | Variable region light chain framework LC-FR2 amino acid sequence of mouse antibody clone C |
| 13 | GVPSRFSGSGSGKDYTLSITSLQTEDVATYYC | Variable region light chain framework LC-FR3 amino acid sequence of mouse antibody clone C |
| 14 | FGSGTKLEIK | Variable region light chain framework LC-FR4 amino acid sequence of mouse antibody clone C |
| 15 | EVQLVESGGGLVKPGGSLRLSCAASGFTFSSYGMSWV RQAPGKRLELVAIINSNGGSTYYPDSVKGRFTFSLDT SKNTLYLQMNSLRAEDTAMYYCVRCHYDYERVFDYWG QGTLVTVSS | Caninized variable heavy chain amino acid sequence of mouse antibody clone C |
| 16 | DIQMTQSPASVSGSLGDKVSITCKANDHINNWLAWYQ QLPGNAPRLLISGSTSLESGVPDRFSGSKSGSSFTLT ISGLQPEDFATYYCQQYWSTPFTFGSGTKVEIK | Caninized variable light chain amino acid sequence of mouse antibody clone C |
| 17 | EVQLVESGGGLVKPGGSLRLSCAASGFTFSSYGMSWV RQAPGKRLELVAIINSNGGSTYYPDSVKGRFTFSLDT SKNTLYLQMNSLRAEDTAMYYCVRCHYDYERVFDYWG QGTLVTVSSASTTAPSVFPLAPSCGSTSGSTVALACL VSGYFPEPVTVSWNSGSLTSGVHTFPSVLQSSGLHSL SSMVTVPSSRWPSETFTCNVVHPASNTKVDKPVFNEC RCTDTPCPVPEPLGGPSVLIFPPKPKDILRITRTPEV TCVVLDLGREDPEVQISWFVDGKEVHTAKTQSREQQF NGTYRVVSVLPIEHQDWLTGKEFKCRVNHIDLPSPIE RTISKARGRAHKPSVYVLPPSPKELSSSDTVSITCLI KDFYPPDIDVEWQSNGQQEPERKHRMTPPQLDEDGSY FLYSKLSVDKSRWQQGDPFTCAVMHETLQNHYTDLSL SHSPGK | Caninized heavy chain sequence from mouse antibody clone C and canine IgG-A |
| 18 | EVQLVESGGGLVKPGGSLRLSCAASGFTFSSYGMSWV RQAPGKRLELVAIINSNGGSTYYPDSVKGRFTFSLDT SKNTLYLQMNSLRAEDTAMYYCVRCHYDYERVFDYWG QGTLVTVSSASTTAPSVFPLAPSCGSTSGSTVALACL VSGYFPEPVTVSWNSGSLTSGVHTFPSVLQSSGLYSL SSMVTVPSSRWPSETFTCNVAHPASKTKVDKPVPKRE NGRVPRPPDCPKCPAPEMLGGPSVFIFPPKPKDTLLI ARTPEVTCVVVDLDPEDPEVQISWFVDGKQMQTAKTQ PREEQFNGTYRVVSVLPIGHQDWLKGKQFTCKVNNKA LPSPIERTISKARGQAHQPSVYVLPPSREELSKNTVS LTCLIKDFFPPDIDVEWQSNGQQEPESKYRTTPPQLD EDGSYFLYSKLSVDKSRWQRGDTFICAVMHEALHNHY TQESLSHSPGK | Caninized heavy chain sequence from mouse antibody clone C and canine IgG-B |
| 19 | EVQLVESGGGLVKPGGSLRLSCAASGFTFSSYGMSWV RQAPGKRLELVAIINSNGGSTYYPDSVKGRFTFSLDT SKNTLYLQMNSLRAEDTAMYYCVRCHYDYERVFDYWG QGTLVTVSSASTTAPSVFPLAPSCGSQSGSTVALACL VSGYIPEPVTVSWNSVSLTSGVHTFPSVLQSSGLYSL SSMVTVPSSRWPSETFTCNVAHPATNTKVDKPVAKEC ECKCNCNNCPCPGCGLLGGPSVFIFPPKPKDILVTAR TPTVTCVVVDLDPENPEVQISWFVDSKQVQTANTQPR EEQSNGTYRVVSVLPIGHQDWLSGKQFKCKVNNKALP | Caninized heavy chain sequence from mouse antibody clone C and canine IgG-C |

Description of the Sequences

| SEQ ID NO: | SEQUENCE | DESCRIPTION |
|---|---|---|
| | SPIEEIISKTPGQAHQPNVYVLPPSRDEMSKNTVTLT CLVKDFFPPEIDVEWQSNGQQEPESKYRMTPPQLDED GSYFLYSKLSVDKSRWQRGDTFICAVMHEALHNHYTQ ISLSHSPGK | |
| 20 | EVQLVESGGGLVKPGGSLRLSCAASGFTFSSYGMSWV RQAPGKRLELVAIINSNGGGSTYYPDSVKGRFTFSLDT SKNTLYLQMNSLRAEDTAMYYCVRCHYDYERVFDYWG QGTLVTVSSASTTAPSVFPLAPSCGSTSGSTVALACL VSGYFPEPVTVSWNSGSLTSGVHTFPSVLQSSGLYSL SSTVTVPSSRWPSETFTCNVVHPASNTKVDKPVPKES TCKCISPCPVPESLGGPSVFIFPPKPKDILRITRTPE ITCVVLDLGREDPEVQISWFVDGKEVHTAKTQPREQQ FNSTYRVVSVLPIEHQDWLTGKEFKCRVNHIGLPSPI ERTISKARGQAHQPSVYVLPPSPKELSSSDTVTLICL IKDFFPPEIDVEWQSNGQPEPESKYHTTAPQLDEDGS YFLYSKLSVDKSRWQQGDIFTCAVMHEALQNHYTDLS LSHSPGK | Caninized heavy chain sequence from mouse antibody clone Clone C and canine IgG-D |
| 21 | DIQMTQSPASVSGSLGDKVSITCKANDHINNWLAWYQ QLPGNAPRLLISGSTSLESGVPDRFSGSKSGSSFTLT ISGLQPEDFATYYCQQYWSTPFTFGSGTKVEIKRNDA QPAVYLFQPSPDQLHTGSASVVCLLNSFYPKDINVKW KVDGVIQDTGIQESVTEQDKDSTYSLSSTLTMSSTEY LSHELYSCEITHKSLPSTLIKSFQRSECQRVD | Caninized light chain sequence from mouse antibody clone C and canine light chain constant region |
| 22 | AGIAFPQNPGCRNTEDKNFPQHVKVNLNILNRNTNSR RPSDYYNRSTSPWNLHRNEDPERYPSVIWEAKCRHLG CVNNEGNINYHMNSVPIQQEILVLRRESQHCPHSFRL EKMLVAVGCTCVTPIVRHVA | Mature canine IL17A amino acid sequence |
| 23 | RHLGCVNNEGNI | Canine IL17A epitope, minimal sequence |
| 24 | DIQMTQSSSYLSVSLGGRVTITCKANDHINNWLAWYQ QKPGNAPRLLISGSTSLETGVPSRFSGSGSGKDYTLS ITSLQTEDVATYYCQQYWSTPFTFGSGTKLEIK | Variable light chain amino acid sequence of mouse antibody clone C |
| 25 | EVQLVESGGGLVQPGGSLKLSCAASGFTFSSYGMSWV RQTPDKRLELVAIINSNGGGSTYYPDSVKGRFTISRDN DKNSLYLQMSSLKSEDTAMYYCVRCHYDYERVFDYWG QGTTLTVSS | Variable heavy chain amino acid sequence of mouse antibody clone C |
| 26 | DIQMTQSSSYLSVSLGGRVTITCKANDHINNWLAWYQ QKPGNAPRLLISGSTSLETGVPSRFSGSGSGKDYTLS ITSLQTEDVATYYCQQYWSTPFTFGSGTKLEIKRNDA QPAVYLFQPSPDQLHTGSASVVCLLNSFYPKDINVKW KVDGVIQDTGIQESVTEQDKDSTYSLSSTLTMSSTEY LSHELYSCEITHKSLPSTLIKSFQRSECQRVD | Chimeric variable light chain of mouse antibody clone C and canine light chain constant region |
| 27 | EVQLVESGGGLVQPGGSLKLSCAASGFTFSSYGMSWV RQTPDKRLELVAIINSNGGGSTYYPDSVKGRFTISRDN DKNSLYLQMSSLKSEDTAMYYCVRCHYDYERVFDYWG QGTTLTVSSASTTAPSVFPLAPSCGSTSGSTVALACL VSGYFPEPVTVSWNSGSLTSGVHTFPSVLQSSGLYSL SSMVTVPSSRWPSETFTCNVAHPASKTKVDKPVPKRE NGRVPRPPDCPKCPAPEMLGGPSVFIFPPKPKDTLLI ARTPEVTCVVVDLDPEDPEVQISWFVDGKQMQTAKTQ PREEQFNGTYRVVSVLPIGHQDWLKGKQFTCKVNNKA LPSPIERTISKARGQAHQPSVYVLPPSREELSKNTVS LTCLIKDFFPPDIDVEWQSNGQQEPESKYRTTPPQLD EDGSYFLYSKLSVDKSRWQRGDTFICAVMHEALHNHY TQESLSHSPGK | Chimeric variable heavy chain of mouse antibody clone C and canine IgG-B |
| 28 | MTLVTTSSMFQSLLLLLSLVAIIKAGIAFPQNPGCRN TEDKNFPQHVKVNLNILNRNTNSRRPSDYYNRSTSPW NLHRNEDPERYPSVIWEAKCRHLGCVNNEGNINYHMN SVPIQQEILVLRRESQHCPHSFRLEKMLVAVGCTCVT PIVRHVA | Canine IL17A precursor amino acid sequence |

-continued

| | Description of the Sequences | |
|---|---|---|
| SEQ ID NO: | SEQUENCE | DESCRIPTION |
| 29 | MAPLRTSSVSLLLLLSLVAIVKAGIVIPQNPECPNTG DKNFPQNVKINLNVLNRKTNSRRASDYHNRSTSPWNL HRNEDPERYPSVIWEAKCRHLGCVNAEGKVDFHMNSV PIQQEILVLRRESQNCPHSFQLEKMLVAVGCTCVTPI VRHMG | Equine IL17A precursor amino acid sequence |
| 30 | MAPGTTSSMFPSLLLLLCLMAIVRTGIAFPQNPGCPT TEDKNFPQHVKVNVNILNGNKSSRRPLDYYRRSTSPW SLHRNEDPERYPSVIWEAKCLHWGCVNTEGKEDHHMN SVPIQQEILVLRRESRHCPHSFRLEKMLVTVGCTCVT PIVRHVV | Feline IL17A precursor amino acid sequence |
| 31 | MAILRNIAMVKSLLLLVLGLTLLSEVAARKHLKAGET ALCPPLEDNSVRVDIRILRQNRGISISNDFQNRSSSP WDYNITRDPHRFPSEIAEAQCRHSGCINAEGQEDSSM NSVPIQQEFLVLRREPQGCSRSFRLEKVLVTVGCTCV TPIVRYVRA | Canine IL17F precursor amino acid sequence |
| 32 | MGRLGEGLNCTVKNSTCLDDSWIHPRNLTPSSPKDVQ VHLDFAQTQHGDLLPIIGIRWTLQTDASILFLEGAEL SVLQLNTNERVCVKFEFLSKLKHHHKRWHFTFSHFVV EPGQEYEVTVHHLPKPIPDGDPNHQSKNFLVPGCEDP RMRMTTPCVSSGSLWDPNITAEALEAHQLQVHFTLWN ESAQYQILLTSFPHTENRSCFHRVLMVPEPTLKEHHQ RANIMLTGSSSNWCCRHQVQIQPFFSSCLNDCLRHSV TVPCPEIPDAPVSIADYIPLWAYGFITGIAILLVGSV ILLIVCMAWRLPGSHCEKYGNDSKYTDIQPKTSLTPP PLKPRKVWIVYSADHPLYVDVVLKFAQFLLTVCGTEV ALDLLEEQVISEVGVMTWVGRQKQEMVETNSKIIILC SRGTRAKWQAILGWEEPAVQLRCDRWKPSGDLFTAAM NMILPDFKKPACFGTYIICYFRDISSESDIPDLFNIT SRYPLMDKFEEVYFRIQDLEMFEPGRMHRVGELTGEN YLQSPSGWQLKEAVERFREWQVRCPDWFERENLGSAD DQDLPSLDEEVFEEPLLPPGRGIVKQKPLVHEPAPEG CLVIDLLVGEEGRGPSRLEPQLQPQGELMAQTLQTVV FPVKEVPSAQAVEPVPHTVESSTAGRLAVVEGDEACP LLEGCGPWRNSVLCLPMDSEEPPLCRTPMASPSYLPE DVREQLEGLMFSLLEQSLSCQAQEGWDRAAVALKDFR TPYEEEQRQSVQSDQGYISRSSPQPPEGLMEMEEEEA EQDLGKSAKQLSPEDLESLRSLQRQLFFQELQTNSGW DSVELEVP | Canine IL17A receptor (IL17Ra) amino acid sequence |
| 33 | MGRLGEGLNCTVKNSTCLDDSWIHPRNLTPSSPKDVQ VHLDFAQTQHGDLLPIIGIRWTLQTDASILFLEGAEL SVLQLNTNERVCVKFEFLSKLKHHHKRWHFTFSHFVV EPGQEYEVTVHHLPKPIPDGDPNHQSKNFLVPGCEDP RMRMTTPCVSSGSLWDPNITAEALEAHQLQVHFTLWN ESAQYQILLTSFPHTENRSCFHRVLMVPEPTLKEHHQ RANIMLTGSSSNWCCRHQVQIQPFFSSCLNDCLRHSV TVPCPEIPDAPVSIADYIPL | Canine IL17A receptor (IL17Ra) ECD (binding domain fragment) amino acid sequence |
| 34 | DVVMTQTPLSLPVSLGDQASISCRSSQSLVHSNGNTY LHWYLQRPGQSPNLLIYKVSNRFSGVPDRFSGSGSGT DFTLKISRVEAEDLGVYFCSQSTHVPFTFGSGTKLEI K | Variable light chain amino acid sequence of mouse antibody clone A |
| 35 | QVQLKESGPGLVAPSQSLSITCTISGFSLTSNGVHWV RQSPGKDLEWLVVIWSDGTTTYNSDFKSRLSISKDNS KSQVFLKMNSLQTDDTAMYYCARHYDWGYYYAMDYWG QGTSVTVSS | Variable heavy chain amino acid sequence of mouse antibody clone A |
| 36 | DIVLTQSPASLAVSLGQRATISYRASKSVSTSGYSY MHWNQQKPGQPPRLLIYLVSNLESGVPARFSGSGSG TDFTLNIHPVEEEDAATYYCQHIRELYTFGGGTKLE IK | Variable light chain amino acid sequence of mouse antibody clone D |
| 37 | EVQLQQSGPELVKTGASVKISCKASGYSFTYYYMHWV KQSHGKSLEWIGYISCFNGDTNYNQEFKDKATFTADT SSSTAYMQFNSLTSEDSAVYYCARGLSTLITEGWFAY WGQGTLVTVSA | Variable heavy chain amino acid sequence of mouse antibody clone D |

-continued

Description of the Sequences

| SEQ ID NO: | SEQUENCE | DESCRIPTION |
|---|---|---|
| 38 | DVVMTQTPLSLPVSLGDQASISCRSSQSLVHSNGNTY FHWYLQKPGQSPKLLIYKVSNRFSGVPDRFSGSGSGT DFTLKISRVEAEDLGVYFCSQSTHAPFTFGSGTKLEI K | Variable light chain amino acid sequence of mouse antibody clone E |
| 39 | QVQLKESGPGLVAPSQSLSITCTISGFSLTSNGVHWV RQPPGKGLEWLVVIWSDGTTTYNSALKSRLSISKDNS KSQVFLKMNSLQTDDTAMYYCARHYDRGYYYAMDYWG QGTSVTVSS | Variable heavy chain amino acid sequence of mouse antibody clone E |
| 40 | SLRLLDHRALVCSQPGLNCTVKNSTCLDDSWIHPRNL TPSSPKDLQIQLHFAHTQQGDLFPVAHIEWTLQTDAS ILYLEGAELSVLQLNTNERLCVRFEFLSKLRHHHRRW RFTFSHFVVDPDQEYEVTVHHLPKPIPDGDPNHQSKN FLVPDCEHARMKVTTPCMSSGSLWDPDITVETLEAHQ LRVSFTLWNESTHYQILLTSFPHMENHSCFEHMHHIP APRPEEFHQRSDVTLTLRNLKGCCRHQVQIQPFFSSC LNDCLRHSATVSCPEMPDTPEPIPDGSESKYGPPCPP CPAPEAAGGPSVFLFPPKPKDTLMISRTPEVTCVVVD VSQEDPEVQFNWYVDGVEVHNAKTKPREEQFNSTYRV VSVLTVLHQDWLNGKEYKCKVSNKGLPSSIEKTISKA KGQPREPQVYTLPPSQEEMTKNQVSLTCLVKGFYPSD IAVEWESNGQPENNYKTTPPVLDSDGSFFLYSRLTVD KSRWQEGNVFSCSVMHEALHNHYTQKSLSLSLG | HumanIL17Ra ECD-IgG4-Fc |
| 41 | MGRLGEGLNCTVKNSTCLDDSWIHPRNLTPSSPKDVQ VHLDFAQTQHGDLLPIIGIRWTLQTDASILFLEGAEL SVLQLNTNERVCVKFEFLSKLKHHHKRWHFTFSHFVV EPGQEYEVTVHHLPKPIPDGDPNHQSKNFLVPGCEDP RMRMTTPCVSSGSLWDPNITAEALEAHQLVHFTLWN ESAQYQILLTSFPHTENRSCFHRVLMVPEPTLKEHHQ RANIMLTGSSSNWCCRHQVQIQPFFSSCLNDCLRHSV TVPCPEIPDAPVSIADYIGSPKRENGRVPRPPDCPKC PAPEMLGGPSVFIFPPKPKDILLIARTPEVICVVVDL DPEDPEVQISWFVDGKQMQTAKTQPREEQFNGTYRVV SVLPIGHQDWLKGKQFTCKVNNKALPSPIERTISKAR GQAHQPSVYVLPPSREELSKNTVSLTCLIKDFFPPDI DVEWQSNGQQEPESKYRTTPPQLDEDGSYFLYSKLSV DKSRWQRGDTFICAVMHEALHNHYTQESLSHSPGK | Canine IL17Ra ECD-canine IgG-B-Fc |
| 42 | MDMRVPAQLLGLLLLWLRGARCMGRLGEGLNCTVKNS TCLDDSWIHPRNLTPSSPKDVQVHLDFAQTQHGDLLP IIGIRWTLQTDASILFLEGAELSVLQLNTNERVCVKF EFLSKLKHHHKRWHFTFSHFVVEPGQEYEVTVHHLPK PIPDGDPNHQSKNFLVPGCEDPRMRMTTPCVSSGSLW DPNITAEALEAHQLVHFTLWNESAQYQILLTSFPHT ENRSCFHRVLMVPEPTLKEHHQRANIMLTGSSSNWCC RHQVQIQPFFSSCLNDCLRHSVTVPCPEIPDAPVSIA DYIGSENLYFQGPKSCDKTHTCPPCPAPELLGGPSVF LFPPKPKDTLMISRTPEVTCVVVDVSHEDPEVKFNWY VDGVEVHNAKTKPREEQYNSTYRVVSVLTVLHQDWLN GKEYKCKVSNKALPAPIEKTISKAKGQPREPQVYTLP PSRDELTKNQVSLTCLVKGFYPSDIAVEWESNGQPEN NYKTTPPVLDSDGSFFLYSKLTVDKSRWQQGNVFSCS VMHEALHNHYTQKSLSLSPGKHHHHHH | canine IL17Ra ECD-huFc-polyHis |
| 43 | SPRLLDYPAPVCSQQGLNCVVKNSTCLDDSWIHLRNL TPSSPKDVQVHLDFVQTQHGDLLPVAGIRWTLQTDAS ILYLEGAELSVLQLNTNERLCVKFEFLTRLKHHHKRW HFTFSHFVVEPGQEYEVTVHHLPKPIPDGDPNHQSRN FPVPGCEDPRMKMITPCVGSGSLWDPNITVETLEARQ LWVSFTLWNESTHYQILLTSFPHTENHSCFQHTLMVP EPAYQDSRQRSNVTLTLSDSNWCCRHRVQIQPFFSSC LNDCLRHSITVPCPEIPDPPVSIADYIGSPKTASTIE SKTGECPKCPVPEIPGAPSVFIFPPKPKDTLSISRTP EVTCLVVDLGPDDSNVQITWFVDNTEMHTAKTRPREE QFNSTYRVVSVLPILHQDWLKGKEFKCKVNSKSLPSA MERTISKAKGQPHEPQVYVLPPTQEELSENKVSVTCL IKGFHPPDIAVEWEITGQPEPENNYQTTPPQLDSDGT YFLYSRLSVDRSHWQRGNTYTCSVSHEALHSHHTQKS LTQSPGK | Feline IL17Ra ECD-feline IgG-2-Fc |

-continued

Description of the Sequences

| SEQ ID NO: | SEQUENCE | DESCRIPTION |
|---|---|---|
| 44 | SPRLLEHPAPVCSQQGLNCTVKNSTCLDDSWLHPPHL TPSSPKDVQIQLHFAHTQQGDLLPVIHIEWTLQTDAS ILYLEGAELSVLQLSTNERLCVTFEFLSRLKHHHKRW RFTFAHFVVEPGQEYEVTVHHLPKPFPHGDPNHQSRN FLVPDCMDPRMRITIPCVSSGSLWDPNITVETLEAHR LRVDFTLWNESARYQILLSSFPHMENQSCFDDVQNIL KHTPEASHQRANITLTLSDFNWCCRHHVQIQPFFSSC LNDCLRHTVTVPCPEIPDTPDSTADYMGSDMSKCPKC PAPELLGGPSVFIFPPNPKDALMISRIPVVTCVVVNL SDQYPDVQFSWYVDNTEVHSAITKQREAQFNSTYRVV SVLPIQHQDWLSGKEFKCSVTNVGVPQPISRAISRGK GPSRVPQVYVLPPHPDELAKSKVSVTCLVKDFYPPDI SVEWQSNRWPELEGKYSTTPAQLDGDGSYFLYSKLSL ETSRWQQVESFTCAVMHEALHNHFTKTDISESLGK | Equine IL17Ra ECD-equine IgG-2-Fc |
| 45 | PKRENGRVPRPPDCPKCPAPEMLGGPSVFIFPPKPKD ILLIARTPEVTCVVVDLDPEDPEVQISWFVDGKQMQT AKTQPREEQFNGTYRVVSVLPIGHQDWLKGKQFTCKV NNKALPSPIERTISKARGQAHQPSVYVLPPSREELSK NTVSLTCLIKDFFPPDIDVEWQSNGQQEPESKYRTTP PQLDEDGSYFLYSKLSVDKSRWQRGDTFICAVMHEAL HNHYTQESLSHSPGK | canine IgG-B-Fc |
| 46 | AKECECKCNCNNCPCPGCGLLGGPSVFIFPPKPKDIL VTARTPTVTCVVVDLDPENPEVQISWFVDSKQVQTAN TQPREEQSNGTYRVVSVLPIGHQDWLSGKQFKCKVNN KALPSPIEEIISKTPGQAHQPNVYVLPPSRDEMSKNT VTLTCLVKDFFPPEIDVEWQSNGQQEPESKYRMTPPQ LDEDGSYFLYSKLSVDKSRWQRGDTFICAVMHEALHN HYTQISLSHSPGK | canine IgG-C-Fc |
| 47 | PKRENGRVPRPPDCPKCPAPEMLGGPSVFIFPPKPKD ILLIARTPEVTCVVVDLDPEDPEVQISWFVDGKQMQT AKTQPREEQFNGTYRVVSVLPIGHQDWLKGKQFTCRV NNKALPSPIERTISKARGQAHQPSVYVLPPSREELSK NTVSLTCLIKDFFPPDIDVEWQSNGQQEPESKYRTTP PQLDEDGSYFLYSKLSVDKSRWQRGDTFICAVMHEAL HNHYTQESLSHSPGK | canine IgG-B-Fc variant 1 (C1q binding mutant) |
| 48 | AKECECKCNCNNCPCPGCGLLGGPSVFIFPPKPKDIL VTARTPTVTCVVVDLDPENPEVQISWFVDSKQVQTAN TQPREEQSNGTYRVVSVLPIGHQDWLSGKQFKCRVNN KALPSPIEEIISKTPGQAHQPNVYVLPPSRDEMSKNT VTLTCLVKDFFPPEIDVEWQSNGQQEPESKYRMTPPQ LDEDGSYFLYSKLSVDKSRWQRGDTFICAVMHEALHN HYTQISLSHSPGK | canine IgG-C-Fc variant 1 (C1q binding mutant) |
| 49 | PKRENGRVPRPPDCPKCPAPEMLGGPSVFIFPPKPKD TLLIARTPEVTCVVVDLGPEDPEVQISWFVDGKQMQT AKTQPREEQFNGTYRVVSVLPIGHQDWLKGKQFTCKV NNIGLPSPIERTISKARGQAHQPSVYVLPPSREELSK NTVSLTCLIKDFFPPDIDVEWQSNGQQEPESKYRTTP PQLDEDGSYFLYSKLSVDKSRWQRGDTFICAVMHEAL HNHYTQESLSHSPGK | canine IgG-B-Fc variant 2 (CD16 binding mutant 1) |
| 50 | AKECECKCNCNNCPCPGCGLLGGPSVFIFPPKPKDIL VTARTPTVTCVVVDLGPENPEVQISWFVDSKQVQTAN TQPREEQSNGTYRVVSVLPIGHQDWLSGKQFKCKVNN IGLPSPIEEIISKTPGQAHQPNVYVLPPSRDEMSKNT VTLTCLVKDFFPPEIDVEWQSNGQQEPESKYRMTPPQ LDEDGSYFLYSKLSVDKSRWQRGDTFICAVMHEALHN HYTQISLSHSPGK | canine IgG-C-Fc variant 2 (CD16 binding mutant 1) |
| 51 | CRHLGCVNNEGNIN | Canine IL17A epitope C, expanded sequence |
| 52 | GFSLTSNGVH | Variable heavy chain CDR-H1 amino acid sequence of mouse antibody clone A |
| 53 | WLVVIWSDGTTTYNSDFKS | Variable heavy chain CDR-H2 amino acid sequence of mouse antibody clone A |

-continued

| Description of the Sequences | | |
|---|---|---|
| SEQ ID NO: | SEQUENCE | DESCRIPTION |
| 109 | VIWSDGTTTYNSDFKS | Variable heavy chain CDR-H2 v2 amino acid sequence of clone A |
| 54 | ARHYDWGYYYAMDY | Variable heavy chain CDR-H3 amino acid sequence of mouse antibody clone A |
| 55 | QVQLKESGPGLVAPSQSLSITCTIS | Variable region heavy chain framework HC-FR1 amino acid sequence of mouse antibody clone A |
| 56 | WVRQSPGKDLE | Variable region heavy chain framework HC-FR2 amino acid sequence of mouse antibody clone A |
| 110 | WVRQSPGKDLEWLV | Variable region heavy chain framework HC-FR2 v2 amino acid sequence of mouse antibody clone A |
| 57 | RLSISKDNSKSQVFLKMNSLQTDDTAMYYC | Variable region heavy chain framework HC-FR3 amino acid sequence of mouse antibody clone A |
| 58 | WGQGTSVTVSS | Variable region heavy chain framework HC-FR4 amino acid sequence of mouse antibody clone A |
| 59 | SSQSLVHSNGNTYLHWY | Variable light chain CDR-L1 amino acid sequence of mouse antibody clone A |
| 111 | SSQSLVHSNGNTYLH | Variable light chain CDR-L1 v2 amino acid sequence of mouse antibody clone A |
| 60 | LLIYKVSNRFS | Variable light chain CDR-L2 amino acid sequence of mouse antibody clone A |
| 112 | KVSNRFS | Variable light chain CDR-L2 v2 amino acid sequence of mouse antibody clone A |
| 61 | SQSTHVPFT | Variable light chain CDR-L3 amino acid sequence of mouse antibody clone A |
| 62 | DVVMTQTPLSLPVSLGDQASISCR | Variable region light chain framework LC-FR1 amino acid sequence of mouse antibody clone A |
| 63 | LQRPGQSPN | Variable region light chain framework LC-FR2 amino acid sequence of mouse antibody clone A |
| 113 | WYLQRPGQSPNLLIY | Variable region light chain framework LC-FR2 v2 amino acid sequence of mouse antibody clone A |
| 64 | GVPDRFSGSGSGTDFTLKISRVEAEDLGVYFC | Variable region light chain framework LC-FR3 amino acid sequence of mouse antibody clone A |

-continued

| | Description of the Sequences | |
|---|---|---|
| SEQ ID NO: | SEQUENCE | DESCRIPTION |
| 65 | FGSGTKLEIK | Variable region light chain framework LC-FR4 amino acid sequence of mouse antibody clone A |
| 66 | GFSLTSNGVH | Variable heavy chain CDR-H1 amino acid sequence of mouse antibody clone E |
| 67 | WLVVIWSDGTTTYNSALKS | Variable heavy chain CDR-H2 amino acid sequence of mouse antibody clone E |
| 114 | VIWSDGITTYNSALKS | Variable heavy chain CDR-H2 v2 amino acid sequence of mouse antibody clone E |
| 68 | ARHYDRGYYYAMDY | Variable heavy chain CDR-H3 amino acid sequence of mouse antibody clone E |
| 69 | QVQLKESGPGLVAPSQSLSITCTIS | Variable region heavy chain framework HC-FR1 amino acid sequence of mouse antibody clone E |
| 70 | WVRQPPGKGLE | Variable region heavy chain framework HC-FR2 amino acid sequence of mouse antibody clone E |
| 115 | WVRQPPGKGLEWLV | Variable region heavy chain framework HC-FR2 v2 amino acid sequence of mouse antibody clone E |
| 71 | RLSISKDNSKSQVFLKMNSLQTDDTAMYYC | Variable region heavy chain framework HC-FR3 amino acid sequence of mouse antibody clone E |
| 72 | WGQGTSVTVSS | Variable region heavy chain framework HC-FR4 amino acid sequence of mouse antibody clone E |
| 73 | RSSQSLVHSNGNTYFHWY | Variable light chain CDR-L1 amino acid sequence of mouse antibody clone E |
| 116 | RSSQSLVHSNGNTYFH | Variable light chain CDR-L1 v2 amino acid sequence of mouse antibody clone E |
| 74 | LLIYKVSNRFS | Variable light chain CDR-L2 amino acid sequence of mouse antibody clone E |
| 117 | KVSNRFS | Variable light chain CDR-L2 v2 amino acid sequence of mouse antibody clone E |
| 75 | SQSTHAPFT | Variable light chain CDR-L3 amino acid sequence of mouse antibody clone E |
| 76 | DVVMTQTPLSLPVSLGDQASISC | Variable region light chain framework LC-FR1 amino acid sequence of mouse antibody clone E |

-continued

| SEQ ID NO: | SEQUENCE | DESCRIPTION |
|---|---|---|
| 77 | LQKPGQSPK | Variable region light chain framework LC-FR2 amino acid sequence of mouse antibody clone E |
| 118 | WYLQKPGQSPKLLIY | Variable region light chain framework LC-FR2 v2 amino acid sequence of mouse antibody clone E |
| 78 | GVPDRFSGSGSGTDFTLKISRVEAEDLGVYFC | Variable region light chain framework LC-FR3 amino acid sequence of mouse antibody clone E |
| 79 | FGSGTKLEIK | Variable region light chain framework LC-FR4 amino acid sequence of mouse antibody clone E |
| 80 | GYSFTYYYMH | Variable heavy chain CDR-H1 amino acid sequence of mouse antibody clone D |
| 81 | WIGYISCFNGDTNYNQEFKD | Variable heavy chain CDR-H2 amino acid sequence of mouse antibody clone D |
| 119 | YISCFNGDTNYNQEFKD | Variable heavy chain CDR-H2 v2 amino acid sequence of mouse antibody clone D |
| 82 | ARGLSTLITEGWFAY | Variable heavy chain CDR-H3 amino acid sequence of mouse antibody clone D |
| 83 | EVQLQQSGPELVKTGASVKISCKAS | Variable region heavy chain framework HC-FR1 amino acid sequence of mouse antibody clone D |
| 84 | WVKQSHGKSLE | Variable region heavy chain framework HC-FR2 amino acid sequence of mouse antibody clone D |
| 120 | WVKQSHGKSLEWIG | Variable region heavy chain framework HC-FR2 v2 amino acid sequence of mouse antibody clone D |
| 85 | KATFTADTSSSTAYMQFNSLTSEDSAVYYC | Variable region heavy chain framework HC-FR3 amino acid sequence of mouse antibody clone D |
| 86 | WGQGTLVTVSA | Variable region heavy chain framework HC-FR4 amino acid sequence of mouse antibody clone D |
| 87 | RASKSVSTSGYSYMHWN | Variable light chain CDR-L1 amino acid sequence of mouse antibody clone D |
| 121 | RASKSVSTSGYSYMH | Variable light chain CDR-L1 v2 amino acid sequence of mouse antibody clone D |
| 88 | LLIYLVSNLES | Variable light chain CDR-L2 amino acid sequence of mouse antibody clone D |

-continued

| | Description of the Sequences | |
|---|---|---|
| SEQ ID NO: | SEQUENCE | DESCRIPTION |
| 122 | LVSNLES | Variable light chain CDR-L2 v2 amino acid sequence of mouse antibody clone D |
| 89 | QHIRELYT | Variable light chain CDR-L3 amino acid sequence of mouse antibody clone D |
| 90 | DIVLTQSPASLAVSLGQRATISY | Variable region light chain framework LC-FR1 amino acid sequence of mouse antibody clone D |
| 91 | QQKPGQPPR | Variable region light chain framework LC-FR2 amino acid sequence of mouse antibody clone D |
| 123 | WNQQKPGQPPRLLIY | Variable region light chain framework LC-FR2 v2 amino acid sequence of mouse antibody clone D |
| 92 | GVPARFSGSGSGTDFTLNIHPVEEEDAATYYC | Variable region light chain framework LC-FR3 amino acid sequence of mouse antibody clone D |
| 93 | FGGGTKLEIK | Variable region light chain framework LC-FR4 amino acid sequence of mouse antibody clone D |
| 94 | LGEGLNCTVKNSTCLDDSWIHPRNLTPSSPKDVQVHL DFAQTQHGDLLPIIGIRWTLQTDASILFLEGAELSVL QLNTNERVCVKFEELSKLKHHHKRWHFTFSHFVVEPG QEYEVTVHHLPKPIPDGDPNHQSKNFLVPGCEDPRMR MTTPCVSSGSLWDPNITAEALEAHQLQVHFTLWNESA QYQILLTSEPHTENRSCFHRVLMVPEPTLKEHHQRAN IMLIGSSSNWCCRHQVQIQPFFSSCLNDCLRHSVTVP CP | Truncated canine IL17Ra ECD |
| 95 | MAVLGLLFCLVTFPSCVLSTETQPPVTNLSVSVENLC TVIWTWDPPEGASPNCTLRYFSHFDNKQDKKIAPETH RSKEVPLNERICLQVGSQCSTNESDNPSILVEKCTPP PEGDPESAVTELQCVWHNLSYMKCTWLPGRNTSPDTN YTLYYWHSSLGKILQCEDIYREGQHIGCSFALTNLKD SSFEQHSVQIVVKDNAGKIRPSFNIVPLTSHVKPDPP HIKRLFFQNGNLYVQWKNPQNFYSRCLSYQVEVNNSQ TETNDIFYVEEAKCQNSEFEGNLEGTICFMVPGVLPD TLNTVRIRVRTNKLCYEDDKLWSNWSQAMSIGENTDP TGGGSGSGSVKVLHEPSCFSDYISTSVCQWKMDHPTN CSAELRLSYQLDFMGSENHTCVPENREDSVCVCSMPI DDAVEADVYQLDLWAGQQLLWSGSFQPSKHVKPRTPG NLTVHPNISHTWLLMWTNPYPTENHLHSELTYMVNVS NDNDPEDFKVYNVTYMGPTLRLAASTLKSGASYSARV RAWAQTYNSTWSDWSPSTTWLNYYEPKRENGRVPRPP DCPKCPAPEMLGGPSVFIFPPKPKDTLLIARTPEVTC VVVDLDPEDPEVQISWFVDGKQMQTAKTQPREEQFNG TYRVVSVLPIGHQDWLKGKQFTCKVNNKALPSPIERT ISKARGQAHQPSVYVLPPSREELSKNIVSLICLIKDF FPPDIDVEWQSNGQQEPESKYRTTPPQLDEDGSYFLY SKLSVDKSRWQRGDTFICAVMHEALHNHYTQESLSHS PGK | IL4R/IL13R-canine IgG-B |
| 96 | MAVLGLLFCLVTFPSCVLSTETQPPVTNLSVSVENLC TVIWTWDPPEGASPNCTLRYFSHFDNKQDKKIAPETH RSKEVPLNERICLQVGSQCSTNESDNPSILVEKCTPP PEGDPESAVTELQCVWHNLSYMKCTWLPGRNTSPDTN YTLYYWHSSLGKILQCEDIYREGQHIGCSFALTNLKD SSFEQHSVQIVVKDNAGKIRPSFNIVPLTSHVKPDPP HIKRLFFQNGNLYVQWKNPQNFYSRCLSYQVEVNNSQ TETNDIFYVEEAKCQNSEFEGNLEGTICFMVPGVLPD TLNTVRIRVRTNKLCYEDDKLWSNWSQAMSIGENTDP | IL4R/IL13R-canine IgG-B variant 1 (C1q binding mutant) |

| SEQ ID NO: | SEQUENCE | DESCRIPTION |
|---|---|---|
| | TGGGSGSGSVKVLHEPSCFSDYISTSVCQWKMDHPTN CSAELRLSYQLDFMGSENHTCVPENREDSVCVCSMPI DDAVEADVYQLDLWAGQQLLWSGSFQPSKHVKPRTPG NLTVHPNISHTWLLMWTNPYPTENHLHSELTYMVNVS NDNDPEDFKVYNVTYMGPTLRLAASTLKSGASYSARV RAWAQTYNSTWSDWSPSTTWLNYYEPKRENGRVPRPP DCPKCPAPEMLGGPSVFIFPPKPKDTLLIARTPEVTC VVVDLDPEDPEVQISWFVDGKQMQTAKTQPREEQFNG TYRVVSVLPIGHQDWLKGKQFTCRVNNKALPSPIERT ISKARGQAHQPSVYVLPPSREELSKNTVSLTCLIKDF FPPDIDVEWQSNGQQEPESKYRTTPPQLDEDGSYFLY SKLSVDKSRWQRGDTFICAVMHEALHNHYTQESLSHS PGK | |
| 97 | SLRLLDHRALVCSQPGLNCTVKNSTCLDDSWIHPRNL TPSSPKDLQIQLHFAHTQQGDLFPVAHIEWTLQTDAS ILYLEGAELSVLQLNTNERLCVRFEFLSKLRHHHRRW RFTFSHFVVDPDQEYEVTVHHLPKPIPDGDPNHQSKN FLVPDCEHARMKVTTPCMSSGSLWDPDITVETLEAHQ LRVSFTLWNESTHYQILLTSFPHMENHSCFEHMHHIP APRPEEFHQRSDVTLTLRNLKGCCRHQVQIQPFFSSC LNDCLRHSATVSCP | Human IL17Ra ECD |
| 98 | SPRLLDYPAPVCSQQGLNCVVKNSTCLDDSWIHLRNL TPSSPKDVQVHLDFVQTQHGDLLPVAGIRWTLQTDAS ILYLEGAELSVLQLNTNERLCVKFEFLTRLKHHHKRW HFTFSHFVVEPGQEYEVTVHHLPKPIPDGDPNHQSRN FPVPGCEDPRMKMITPCVGSGSLWDPNITVETLEARQ LWVSFTLWNESTHYQILLTSFPHTENHSCFQHTLMVP EPAYQDSRQRSNVTLTLSDSNWCCRHRVQIQPFFSSC LNDCLRHSITVPCPEIPDPPVSIADYI | Feline IL17Ra ECD |
| 99 | SPRLLEHPAPVCSQQGLNCTVKNSTCLDDSWLHPPHL TPSSPKDVQIQLHFAHTQQGDLLPVIHIEWTLQTDAS ILYLEGAELSVLQLSTNERLCVTFEFLSRLKHHHKRW RFTFAHFVVEPGQEYEVTVHHLPKPFPHGDPNHQSRN FLVPDCMDPRMRITTPCVSSGSLWDPNITVETLEAHR LRVDFTLWNESARYQILLSSFPHMENQSCFDDVQNIL KHTPEASHQRANITLTLSDFNWCCRHHVQIQPFFSSC LNDCLRHTVTVPCPEIPDTPDSTADYM | Equine IL17Ra ECD |
| 100 | MKFPSQLLLFLLFRITGIICDIQMTQSSSYLSVSLGG RVTITCKANDHINNWLAWYQQKPGNAPRLLISGSTSL ETGVPSRFSGSGSGKDYTLSITSLQTEDVATYYCQQY WSTPPFTFGSGTKLEIKRADAAPTVSIFPPSSEQLTSG GASVVLGVIMVIAVSCVKLLSAHNST | Mouse monoclonal antibody Clone C variable light chain, with leader sequence and certain C-terminal sequence |
| 101 | MKLPVRLLVLMFWIPASNSDVVMTQTPLSLPVSLGDQ ASISCRSSQSLVHSNGNTYFHWYLQKPGQSPKLLIYK VSNRFSGVPDRFSGSGSGTDFTLKISRVEAEDLGVYF CSQSTHAPFTFGSGTKLEIKRADAAPTVSIFPPSSEQ LTSGGASVVSRAN | Mouse monoclonal antibody Clone E variable light chain, with leader sequence and certain C-terminal sequence |
| 102 | MKLPVRLLVLMFWIPASSSDVVMTQTPLSLPVSLGDQ ASISCRSSQSLVHSNGNTYLHWYLQRPGQSPNLLIYK VSNRFSGVPDRFSGSGSGTDFTLKISRVEAEDLGVYF CSQSTHVPFTFGSGTKLEIKRADAAPTVSIFPPSSEQ LTSGGASVVCKGEF | Mouse monoclonal antibody Clone A variable light chain, with leader sequence and certain C-terminal sequence |
| 103 | METDTLLLWVLLLWVPGSTGDIVLTQSPASLAVSLGQ RATISYRASKSVSTSGYSYMHWNQQKPGQPPRLLIYL VSNLESGVPARFSGSGSGTDFTLNIHPVEEEDAATYY CQHIRELYTFGGGTKLEIKRADAAPTVSI | Mouse monoclonal antibody Clone D variable light chain, with leader sequence and certain C-terminal sequence |
| 104 | MGWIWIFLFLLSGTAGVHSEVQLQQSGPELVKTGASV KISCKASGYSFTYYYMHWVKQSHGKSLEWIGYISCFN GDTNYNQEFKDKATFTADTSSSTAYMQFNSLTSEDSA VYYCARGLSTLITEGWFAYWGQGTLVTVSAAKTTPPS VYPLAPGSA | Mouse monoclonal antibody Clone D variable heavy chain, with leader sequence and certain C-terminal sequence |
| 105 | MNLGLSFIFLALILKGVQCEVQLVESGGGLVQPGGSL KLSCAASGFTFSSYGMSWVRQTPDKRLELVAIINSNG GSTYYPDSVKGRFTISRDNDKNSLYLQMSSLKSEDTA | Mouse monoclonal antibody Clone C variable heavy chain, with leader sequence |

-continued

---

Description of the Sequences

---

| SEQ ID NO: | SEQUENCE | DESCRIPTION |
|---|---|---|
|  | MYYCVRCHYDYERVFDYWGQGTTLTVSSAKTTPPSVY PLAPGSAAQTNSMVTLGCLVKGYFPE | and certain C-terminal sequence |
| 106 | MAVLGLLLCLVTFPSCVLSQVQLKESGPGLVAPSQSL SITCTISGFSLTSNGVHWVRQSPGKDLEWLVVIWSDG TTTYNSDFKSRLSISKDNSKSQVFLKMNSLQTDDTAM YYCARHYDWGYYYAMDYWGQGTSVTVSSAKTTPPSVY PLAPGSAAQTNSMVTLGCLVKGEF | Mouse monoclonal antibody Clone A variable heavy chain, with leader sequence and certain C-terminal sequence |
| 107 | MAVLGLLLCLVTFPSCVLSQVQLKESGPGLVAPSQSL SITCTISGFSLTSNGVHWVRQPPGKGLEWLVVIWSDG TTTYNSALKSRLSISKDNSKSQVFLKMNSLQTDDTAM YYCARHYDRGYYYAMDYWGQGTSVTVSSAKTTPPSVY PLAPGSAAQTNSMVTLGCLVKGEF | Mouse monoclonal antibody Clone E variable heavy chain, with leader sequence and certain C-terminal sequence |

---

DESCRIPTION OF CERTAIN EMBODIMENTS

Antibodies that bind canine IL17A, feline IL17A, or equine IL17A are provided. Antibody heavy chains and light chains that are capable of forming antibodies that bind IL17A are also provided. In addition, antibodies, heavy chains, and light chains comprising one or more particular complementary determining regions (CDRs) are provided. The present disclosure also provides polypeptides comprising an IL17Ra ECD polypeptide that are capable of binding IL17A. Polynucleotides encoding antibodies to IL17A and polypeptides comprising an IL17Ra ECD polypeptide are provided as well as methods of producing and purifying the antibodies and polypeptides. Methods of treatment using antibodies to IL17A and polypeptides comprising an IL17A ECD polypeptide to bind IL17A and inhibit IL17A-mediated signaling are provided. Such methods include, but are not limited to, methods of treating IL17A-induced conditions in a subject, such as companion animal species. Methods of detecting IL17A in a sample from a companion animal species are also provided.

The present disclosure also provides IgG Fc variant polypeptides having one or more amino acid substitutions and reducing binding to C1q and/or CD16 and methods of producing and using the same. For example, IgG Fc variants and/or polypeptides comprising the IgG Fc variants (e.g., fusion polypeptides comprising the IgG Fc variants and the anti-IL17A antibodies and/or IL17Ra ECD polypeptides described herein) may have reduced complement-mediated immune responses and/or antibody-dependent cell-mediated cytotoxicity.

For the convenience of the reader, the following definitions of terms used herein are provided.

As used herein, numerical terms such as Kd are calculated based upon scientific measurements and, thus, are subject to appropriate measurement error. In some instances, a numerical term may include numerical values that are rounded to the nearest significant figure.

As used herein, "a" or "an" means "at least one" or "one or more" unless otherwise specified. As used herein, the term "or" means "and/or" unless specified otherwise. In the context of a multiple dependent claim, the use of "or" when referring back to other claims refers to those claims in the alternative only.

Exemplary Anti-IL17 Antibodies

Novel antibodies directed against IL17A are provided, for example antibodies that bind to canine IL17A, feline IL17A, and/or equine IL17A. Anti-IL17 antibodies provided herein include, but are not limited to, monoclonal antibodies, mouse antibodies, chimeric antibodies, caninized antibodies, felinized antibodies, and equinized antibodies. In some embodiments, an anti-IL17A antibody is an isolated mouse monoclonal antibody such as Clone C, Clone A, Clone D, and Clone E.

A hybridoma bank generated from immunization of mice with human IL17A was screened for affinity to canine IL17A by enzyme linked immunosorbent assay (ELISA). Monoclonal antibodies Clone C, Clone A, Clone D, and Clone E were selected for further investigation. The variable heavy chain (VH) and variable light chain (VL) of each of the four clones were sequenced and analyzed by sequence alignment (FIG. 2).

Provided herein are amino acid sequences of monoclonal antibody Clone C. For example, the variable heavy chain CDRs (SEQ ID NOs: 1-3), variable light chain CDRs (SEQ ID NOs: 8, 9 or 108, and 10), variable region heavy chain framework sequences (SEQ ID NOs: 4-7), and variable region light chain framework sequences (SEQ ID NOs: 11-14) for monoclonal antibody Clone C are provided. The amino acid sequences of the variable light chain and variable heavy chain of monoclonal antibody Clone C are provided (SEQ ID NOs: 24 and 25, respectively).

Also provided herein are amino acid sequences of monoclonal antibody Clone A. For example, the variable heavy chain CDRs (SEQ ID NOs: 52, 53 or 109, and 54), variable light chain CDRs (SEQ ID NOs: 59 or 111, 60 or 112, and 61), variable region heavy chain framework sequences (SEQ ID NOs: 55, 56 or 110, 57, and 58), and variable region light chain framework sequences (SEQ ID NOs: 62, 63 or 113, 64, and 65) for monoclonal antibody Clone A are provided. The amino acid sequences of the variable light chain and variable heavy chain of monoclonal antibody Clone A are provided (SEQ ID NOs: 34 and 35, respectively).

In addition, provided herein are amino acid sequences of monoclonal antibody Clone D. For example, the variable heavy chain CDRs (SEQ ID NOs: 80, 81 or 119, and 82), variable light chain CDRs (SEQ ID NOs: 87 or 121, 88 or 122, and 89), variable region heavy chain framework sequences (SEQ ID NOs: 83, 84 or 120, 85, and 86), and variable region light chain framework sequences (SEQ ID NOs: 90, 91 or 123, 92, and 93) for monoclonal antibody Clone D are provided. The amino acid sequences of the variable light chain and variable heavy chain of monoclonal antibody Clone D are provided (SEQ ID NOs: 36 and 37, respectively).

Provided herein are amino acid sequences of monoclonal antibody Clone E. For example, the variable heavy chain CDRs (SEQ ID NOs: 66, 67 or 114, and 68), variable light chain CDRs (SEQ ID NOs: 73 or 116, 74 or 117, and 75), variable region heavy chain framework sequences (SEQ ID NOs: 69, 70 or 115, 71, and 72), and variable region light chain framework sequences (SEQ ID NOs: 76, 77 or 118, 78, and 79) for monoclonal antibody Clone A are provided. The amino acid sequences of the variable light chain and variable heavy chain of monoclonal antibody Clone A are provided (SEQ ID NOs: 38 and 39, respectively).

Also provided herein are chimeric, caninized, felinized, and equinized antibodies derived from Clone C, A, D, and E antibodies. For example, in some embodiments, amino acid sequences of caninized monoclonal antibody Clone C are provided, such as SEQ ID NOs: 15-21. In some embodiments, amino acid sequences of chimeric antibodies derived from monoclonal antibody Clone C are provided, such as SEQ ID NOs: 26 and 27.

The term "antibody" herein is used in the broadest sense and encompasses various antibody structures, including but not limited to monoclonal antibodies, polyclonal antibodies, multispecific antibodies (for example, bispecific (such as Bi-specific T-cell engagers) and trispecific antibodies), and antibody fragments (such as Fab, F(ab')2, ScFv, minibody, diabody, triabody, and tetrabody) so long as they exhibit the desired antigen-binding activity. Canine, feline, and equine species have different varieties (classes) of antibodies that are shared by many mammalians.

The term antibody includes, but is not limited to, fragments that are capable of binding to an antigen, such as Fv, single-chain Fv (scFv), Fab, Fab', di-scFv, sdAb (single domain antibody) and (Fab')2 (including a chemically linked F(ab')2). Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen combining sites and is still capable of cross-linking antigen. The term antibody also includes, but is not limited to, chimeric antibodies, humanized antibodies, and antibodies of various species such as mouse, human, cynomolgus monkey, canine, feline, equine, etc. Furthermore, for all antibody constructs provided herein, variants having the sequences from other organisms are also contemplated. Thus, if a murine version of an antibody is disclosed, one of skill in the art will appreciate how to transform the murine sequence based antibody into a cat, dog, horse, etc. sequence. Antibody fragments also include either orientation of single chain scFvs, tandem di-scFv, diabodies, tandem tri-sdcFv, minibodies, etc. Antibody fragments also include nanobodies (sdAb, an antibody having a single, monomeric domain, such as a pair of variable domains of heavy chains, without a light chain). An antibody fragment can be referred to as being a specific species in some embodiments (for example, mouse scFv or a canine scFv). This denotes the sequences of at least part of the non-CDR regions, rather than the source of the construct. In some embodiments, the antibodies comprise a label or are conjugated to a second moiety.

The terms "label" and "detectable label" mean a moiety attached to an antibody or its analyte to render a reaction (for example, binding) between the members of the specific binding pair, detectable. The labeled member of the specific binding pair is referred to as "detectably labeled." Thus, the term "labeled binding protein" refers to a protein with a label incorporated that provides for the identification of the binding protein. In some embodiments, the label is a detectable marker that can produce a signal that is detectable by visual or instrumental means, for example, incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Examples of labels for polypeptides include, but are not limited to, the following: radioisotopes or radionuclides (for example, $^{3}$H, $^{14}$C, $^{35}$S $^{90}$Y$^{99}$Tc, $^{111}$In, $^{125}$I, $^{131}$I, $^{177}$Lu, $^{166}$Ho, or $^{153}$Sm); chromogens, fluorescent labels (for example, FITC, rhodamine, lanthanide phosphors), enzymatic labels (for example, horseradish peroxidase, luciferase, alkaline phosphatase); chemiluminescent markers; biotinyl groups; predetermined polypeptide epitopes recognized by a secondary reporter (for example, leucine zipper pair sequences, binding sites for secondary antibodies, metal binding domains, epitope tags); and magnetic agents, such as gadolinium chelates. Representative examples of labels commonly employed for immunoassays include moieties that produce light, for example, acridinium compounds, and moieties that produce fluorescence, for example, fluorescein. In this regard, the moiety itself may not be detectably labeled but may become detectable upon reaction with yet another moiety.

The term "monoclonal antibody" refers to an antibody of a substantially homogeneous population of antibodies, that is, the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. Thus, a sample of monoclonal antibodies can bind to the same epitope on the antigen. The modifier "monoclonal" indicates the character of the antibody as being obtained from a substantially homogeneous population of antibodies, and is not to be construed as requiring production of the antibody by any particular method. For example, the monoclonal antibodies may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

In some embodiments, the monoclonal antibody is an isolated mouse antibody selected from Clone C, Clone A, Clone D, and Clone E.

"Amino acid sequence," means a sequence of amino acids residues in a peptide or protein. The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

"IL17A" as used herein refers to any native IL17A that results from expression and processing of IL17A in a cell. The term includes IL17A from any vertebrate source, including mammals such as primates (e.g., humans and cynomolgus monkeys) and rodents (e.g., mice and rats), and companion animals (e.g., dogs, cats, and equine), unless otherwise indicated. The term also includes naturally occurring variants of IL17A, e.g., splice variants or allelic variants.

The term "companion animal species" refers to an animal suitable to be a companion to humans. In some embodiments, a companion animal species is a small mammal, such as a canine, feline, dog, cat, horse, rabbit, ferret, guinea pig, rodent, etc. In some embodiments, a companion animal species is a farm animal, such as a horse, cow, pig, etc.

In some embodiments, a canine IL17A comprises the amino acid sequence of SEQ ID NO: 22 and SEQ ID NO: 28. In some embodiments, a feline IL17A comprises the amino acid sequence of SEQ ID NO: 30. In some embodiments, an equine IL17A comprises the amino acid sequence of SEQ ID NO: 29.

The term "IL17A binding domain" of an antibody means the binding domain formed by a light chain and heavy chain of an anti-IL17A antibody, which binds IL17A.

In some embodiments, the IL17A binding domain binds IL17A of one or more species. In some embodiments, the IL17A binding domain binds IL17A from one or more companion animal species, such as canine IL17A, feline IL17A or equine IL17A.

As used herein, the term "epitope" refers to a site on a target molecule (for example, an antigen, such as a protein, nucleic acid, carbohydrate or lipid) to which an antigen-binding molecule (for example, an antibody, antibody fragment, or scaffold protein containing antibody binding regions) binds. Epitopes often include a chemically active surface grouping of molecules such as amino acids, polypeptides or sugar side chains and have specific three-dimensional structural characteristics as well as specific charge characteristics. Epitopes can be formed both from contiguous or juxtaposed noncontiguous residues (for example, amino acids, nucleotides, sugars, lipid moiety) of the target molecule. Epitopes formed from contiguous residues (for example, amino acids, nucleotides, sugars, lipid moiety) typically are retained on exposure to denaturing solvents whereas epitopes formed by tertiary folding typically are lost on treatment with denaturing solvents. An epitope may include but is not limited to at least 3, at least 5 or 8-10 residues (for example, amino acids or nucleotides). In some examples an epitope is less than 20 residues (for example, amino acids or nucleotides) in length, less than 15 residues or less than 12 residues. Two antibodies may bind the same epitope within an antigen if they exhibit competitive binding for the antigen. In some embodiments, an epitope can be identified by a certain minimal distance to a CDR residue on the antigen-binding molecule. In some embodiments, an epitope can be identified by the above distance, and further limited to those residues involved in a bond (for example, a hydrogen bond) between an antibody residue and an antigen residue. An epitope can be identified by various scans as well, for example an alanine or arginine scan can indicate one or more residues that the antigen-binding molecule can interact with. Unless explicitly denoted, a set of residues as an epitope does not exclude other residues from being part of the epitope for a particular antibody. Rather, the presence of such a set designates a minimal series (or set of species) of epitopes. Thus, in some embodiments, a set of residues identified as an epitope designates a minimal epitope of relevance for the antigen, rather than an exclusive list of residues for an epitope on an antigen.

In some embodiments, the antibody binds to an epitope within amino acids 65 to 88 of SEQ ID NO: 22. In some embodiments, the epitope comprises the amino acid sequence of SEQ ID NO: 23 or SEQ ID NO: 51.

The term "CDR" means a complementarity determining region as defined by at least one manner of identification to one of skill in the art. In some embodiments, CDRs can be defined in accordance with any of the Chothia numbering schemes, the Kabat numbering scheme, a combination of Kabat and Chothia, the AbM definition, the contact definition, or a combination of the Kabat, Chothia, AbM, or contact definitions. The various CDRs within an antibody can be designated by their appropriate number and chain type, including, without limitation as CDR-H1, CDR-H2, CDR-H3, CDR-L1, CDR-L2, and CDR-L3. The term "CDR" is used herein to also encompass a "hypervariable region" or HVR, including hypervariable loops.

In some embodiments, an anti-IL17A antibody comprises a heavy chain comprising (a) a CDR-H1 comprising the amino acid sequence of SEQ ID NO: 1; (b) a CDR-H2 comprising the amino acid sequence of SEQ ID NO: 2; or (c) a CDR-H3 comprising the amino acid sequence of SEQ ID NO: 3. In some embodiments, an anti-IL17A antibody comprises a light chain comprising (a) a CDR-L1 comprising the amino acid sequence of SEQ ID NO: 8; (b) a CDR-L2 comprising the amino acid sequence of SEQ ID NO: 9 or SEQ ID NO: 108; or (c) a CDR-L3 comprising the amino acid sequence of SEQ ID NO: 10.

In some embodiments, an anti-IL17A antibody comprises a heavy chain comprising (a) a CDR-H1 comprising the amino acid sequence of SEQ ID NO: 52, (b) a CDR-H2 comprising the amino acid sequence of SEQ ID NO: 53 or SEQ ID NO: 109, and (c) a CDR-H3 comprising the amino acid sequence of SEQ ID NO: 54; and a light chain comprising (a) a CDR-L1 comprising the amino acid sequence of SEQ ID NO: 59 or SEQ ID NO: 111, (b) a CDR-L2 comprising the amino acid sequence of SEQ ID NO: 60 or SEQ ID NO: 112, and (c) a CDR-L3 comprising the amino acid sequence of SEQ ID NO: 61.

In some embodiments, an anti-IL17A antibody comprises a heavy chain comprising (a) a CDR-H1 comprising the amino acid sequence of SEQ ID NO: 66, (b) a CDR-H2 comprising the amino acid sequence of SEQ ID NO: 67 or SEQ ID NO: 114, and (c) a CDR-H3 comprising the amino acid sequence of SEQ ID NO: 68; and a light chain comprising (a) a CDR-L1 comprising the amino acid sequence of SEQ ID NO: 73 or SEQ ID NO: 116, (b) a CDR-L2 comprising the amino acid sequence of SEQ ID NO: 74 or SEQ ID NO: 117, and (c) a CDR-L3 comprising the amino acid sequence of SEQ ID NO: 75.

In some embodiments, an anti-IL17A antibody comprises a heavy chain comprising (a) a CDR-H1 comprising the amino acid sequence of SEQ ID NO: 80, (b) a CDR-H2 comprising the amino acid sequence of SEQ ID NO: 81 or SEQ ID NO: 119, and (c) a CDR-H3 comprising the amino acid sequence of SEQ ID NO: 82; and a light chain comprising (a) a CDR-L1 comprising the amino acid sequence of SEQ ID NO: 87 or SEQ ID NO: 121, (b) a CDR-L2 comprising the amino acid sequence of SEQ ID NO: 88 or SEQ ID NO: 122, and (c) a CDR-L3 comprising the amino acid sequence of SEQ ID NO: 89.

The term "variable region" as used herein refers to a region comprising at least three CDRs. In some embodiments, the variable region includes the three CDRs and at least one framework region ("FR"). The terms "heavy chain variable region" or "variable heavy chain" are used interchangeably to refer to a region comprising at least three heavy chain CDRs. The terms "light chain variable region" or "variable light chain" are used interchangeably to refer to a region comprising at least three light chain CDRs.

In some embodiments, the variable heavy chain or variable light chain comprises at least one framework region. In some embodiments, an antibody comprises at least one heavy chain framework region selected from HC-FR1, HC-FR2, HC-FR3, and HC-FR4. In some embodiments, an antibody comprises at least one light chain framework region selected from LC-FR1, LC-FR2, LC-FR3, and LC-FR4. The framework regions may be juxtaposed between light chain CDRs or between heavy chain CDRs. For example, an antibody may comprise a variable heavy chain having the following structure: (HC-FR1)-(CDR-H1)-(HC-FR2)-(CDR-H2)-(HC-FR3)-(CDR-H3)-(HC-FR4). An antibody may comprise a variable heavy chain having the following structure: (CDR-H1)-(HC-FR2)-(CDR-H2)-(HC-FR3)-(CDR-H3). An antibody may also comprise a variable light chain having the following structure: (LC-FR1)-(CDR-L1)-(LC-FR2)-(CDR-L2)-(LC-FR3)-(CDR-L3)-(LC-FR4). An antibody may also comprise a variable light chain having the following structure: (CDR-L1)-(LC-FR2)-(CDR-L2)-(LC-FR3)-(CDR-L3).

In some embodiments, an anti-IL17A antibody comprises one or more of (a) a variable region heavy chain framework 1 (HC-FR1) sequence of SEQ ID NO: 4, (b) a HC-FR2 sequence of SEQ ID NO: 5, (c) a HC-FR3 sequence of SEQ ID NO: 6, (d) a HC-FR4 sequence of SEQ ID NO: 7, (e) a variable region light chain framework 1 (LC-FR1) sequence of SEQ ID NO: 11, (f) an LC-FR2 sequence of SEQ ID NO: 12, (g) an LC-FR3 sequence of SEQ ID NO: 13, or (h) an LC-FR4 sequence of SEQ ID NO: 14.

In some embodiments, an anti-IL17A antibody comprises a variable light chain sequence of (a) SEQ ID NO: 16 or (b) SEQ ID NO: 24. In some embodiments, an anti-IL17A antibody comprises a variable heavy chain sequence of (a) SEQ ID NO: 15 or (b) SEQ ID NO: 25. In some embodiments, an anti-IL17A antibody comprises (a) a variable light chain sequence of SEQ ID NO: 16 and a variable heavy chain sequence of SEQ ID NO: 15 or (b) a variable light chain sequence of SEQ ID NO: 24 and a variable heavy chain sequence of SEQ ID NO: 25.

In some embodiments, an anti-IL17A antibody comprises one or more of (a) a variable region heavy chain framework 1 (HC-FR1) sequence of SEQ ID NO: 55, (b) a HC-FR2 sequence of SEQ ID NO: 56 or SEQ ID NO: 110, (c) a HC-FR3 sequence of SEQ ID NO: 57, (d) a HC-FR4 sequence of SEQ ID NO: 58, (e) a variable region light chain framework 1 (LC-FR1) sequence of SEQ ID NO: 62, (f) an LC-FR2 sequence of SEQ ID NO: 63 or SEQ ID NO: 113, (g) an LC-FR3 sequence of SEQ ID NO: 64, or (h) an LC-FR4 sequence of SEQ ID NO: 65.

In some embodiments, an anti-IL17A antibody comprises a variable light chain sequence of SEQ ID NO: 34. In some embodiments, an anti-IL17A antibody comprises a variable heavy chain sequence of SEQ ID NO: 35. In some embodiments, an anti-IL17A antibody comprises a variable light chain sequence of SEQ ID NO: 34 and a variable heavy chain sequence of SEQ ID NO: 35.

In some embodiments, an anti-IL17A antibody comprises one or more of (a) a variable region heavy chain framework 1 (HC-FR1) sequence of SEQ ID NO: 69, (b) a HC-FR2 sequence of SEQ ID NO: 70 or SEQ ID NO: 115, (c) a HC-FR3 sequence of SEQ ID NO: 71, (d) a HC-FR4 sequence of SEQ ID NO: 72, (e) a variable region light chain framework 1 (LC-FR1) sequence of SEQ ID NO: 76, (f) an LC-FR2 sequence of SEQ ID NO: 77 or SEQ ID NO: 118, (g) an LC-FR3 sequence of SEQ ID NO: 78, or (h) an LC-FR4 sequence of SEQ ID NO: 79.

In some embodiments, an anti-IL17A antibody comprises a variable light chain sequence of SEQ ID NO: 38. In some embodiments, an anti-IL17A antibody comprises a variable heavy chain sequence of SEQ ID NO: 39. In some embodiments, an anti-IL17A antibody comprises a variable light chain sequence of SEQ ID NO: 38 and a variable heavy chain sequence of SEQ ID NO: 39.

In some embodiments, an anti-IL17A antibody comprises one or more of (a) a variable region heavy chain framework 1 (HC-FR1) sequence of SEQ ID NO: 83, (b) a HC-FR2 sequence of SEQ ID NO: 84 or SEQ ID NO: 120, (c) a HC-FR3 sequence of SEQ ID NO: 85, (d) a HC-FR4 sequence of SEQ ID NO: 86, (e) a variable region light chain framework 1 (LC-FR1) sequence of SEQ ID NO: 90, (f) an LC-FR2 sequence of SEQ ID NO: 91 or SEQ ID NO: 123, (g) an LC-FR3 sequence of SEQ ID NO: 92, or (h) an LC-FR4 sequence of SEQ ID NO: 93.

In some embodiments, an anti-IL17A antibody comprises a variable light chain sequence of SEQ ID NO: 36. In some embodiments, an anti-IL17A antibody comprises a variable heavy chain sequence of SEQ ID NO: 37. In some embodiments, an anti-IL17A antibody comprises a variable light chain sequence of SEQ ID NO: 36 and a variable heavy chain sequence of SEQ ID NO: 37.

The term "constant region" as used herein refers to a region comprising at least three constant domains. The terms "heavy chain constant region" or "constant heavy chain" are used interchangeably to refer to a region comprising at least three heavy chain constant domains, CH1, CH2, and CH3. Nonlimiting exemplary heavy chain constant regions include γ, δ, α, ε, and μ. Each heavy chain constant region corresponds to an antibody isotype. For example, an antibody comprising a γ constant region is an IgG antibody, an antibody comprising a δ constant region is an IgD antibody, an antibody comprising an α constant region is an IgA antibody, an antibody comprising a constant region is an IgM antibody, and an antibody comprising an ε constant region is an IgE antibody. Certain isotypes can be further subdivided into subclasses. For example, IgG antibodies include, but are not limited to, IgG1 (comprising a $\gamma_1$ constant region), IgG2 (comprising a $\gamma_2$ constant region), IgG3 (comprising a $\gamma_3$ constant region), and IgG4 (comprising a $\gamma_4$ constant region) antibodies; IgA antibodies include, but are not limited to, IgAQ1 (comprising an $\alpha_1$ constant region) and IgA2 (comprising an $\alpha_2$ constant region) antibodies; and IgM antibodies include, but are not limited to IgM1 and IgM2. The terms "light chain constant region" or "constant light chain" are used interchangeably to refer to a region comprising a light chain constant domain, CL. Nonlimiting exemplary light chain constant regions include X and K. Non-function-altering deletions and alterations within the domains are encompassed within the scope of the term "constant region" unless designated otherwise. Canine, feline, and equine have antibody classes such as IgG, IgA, IgD, IgE, and IgM. Within the canine IgG antibody class are IgG-A, IgG-B, IgG-C, and IgG-D. Within the feline IgG antibody class are IgG1a, IgG1b, and IgG2. Within the equine IgG antibody class are IgG1, IgG2, IgG3, IgG4, IgG5, IgG6, and IgG7.

The term "chimeric antibody" or "chimeric" refers to an antibody in which a portion of the heavy chain or light chain is derived from a particular source or species, while at least a part of the remainder of the heavy chain or light chain is derived from a different source or species. In some embodiments, a chimeric antibody refers to an antibody comprising at least one variable region from a first species (such as mouse, rat, cynomolgus monkey, etc.) and at least one constant region from a second species (such as human, dog, cat, equine, etc.). In some embodiments, a chimeric antibody comprises at least one mouse variable region and at least one canine constant region. In some embodiments, a chimeric antibody comprises at least one mouse variable region and at least one feline constant region. In some embodiments, all of the variable regions of a chimeric antibody are from a first species and all of the constant regions of the chimeric antibody are from a second species. In some embodiments, a chimeric antibody comprises a constant heavy chain region or constant light chain region from a companion animal. In some embodiments, a chimeric antibody comprises a mouse variable heavy and light chains and a companion animal constant heavy and light chains. For example, a chimeric antibody may comprise a mouse variable heavy and light chains and a canine constant heavy and light chains; a chimeric antibody may comprise a mouse variable heavy and light chains and a feline constant heavy and light chains; or a chimeric antibody may comprise a mouse variable heavy and light chains and an equine constant heavy and light chains.

In some embodiments, an anti-IL17A antibody comprises a light chain sequence of SEQ ID NO: 26. In some embodiments, an anti-IL17A antibody comprises a heavy chain sequence of SEQ ID NO: 27. In some embodiments, an anti-IL17A antibody comprises a light chain sequence of SEQ ID NO: 26 and a variable heavy chain sequence of SEQ ID NO: 27.

A "canine chimeric" or "canine chimeric antibody" refers to a chimeric antibody having at least a portion of a heavy chain or a portion of a light chain derived from a dog. A "feline chimeric" or "feline chimeric antibody" refers to a chimeric antibody having at least a portion of a heavy chain or a portion of a light chain derived from a cat. An "equine chimeric" or "equine chimeric antibody" refers to a chimeric antibody having at least a portion of a heavy chain or a portion of a light chain derived from a horse. In some embodiments, a canine chimeric antibody comprises a mouse variable heavy and light chains and a canine constant heavy and light chains. In some embodiments, a feline chimeric antibody comprises a mouse variable heavy and light chains and a feline constant heavy and light chains. In some embodiments, an equine chimeric antibody comprises a mouse variable heavy and light chains and an equine constant heavy and light chains. In some embodiments, the antibody is a chimeric antibody comprising murine variable heavy chain framework regions or murine variable light chain framework regions.

A "canine antibody" as used herein encompasses antibodies produced in a canine; antibodies produced in non-canine animals that comprise canine immunoglobulin genes or comprise canine immunoglobulin peptides; or antibodies selected using in vitro methods, such as phage display, wherein the antibody repertoire is based on a canine immunoglobulin sequence. The term "canine antibody" denotes the genus of sequences that are canine sequences. Thus, the term is not designating the process by which the antibody was created, but the genus of sequences that are relevant.

In some embodiments, an anti-IL17A antibody comprises a canine heavy chain constant region selected from an IgG-A, IgG-B, IgG-C, and IgG-D constant region. In some embodiments, an anti-IL17A antibody is a canine IgG-A, IgG-B, IgG-C, or IgG-D antibody. In some embodiments, an anti-IL17A antibody comprises (a) a heavy chain amino acid sequence of SEQ ID NO: 17; (b) a heavy chain amino acid sequence of SEQ ID NO: 18; (c) a heavy chain amino acid sequence of SEQ ID NO: 19; or (d) a heavy chain amino acid sequence of SEQ ID NO: 20.

A "feline antibody" as used herein encompasses antibodies produced in a feline; antibodies produced in non-feline animals that comprise feline immunoglobulin genes or comprise feline immunoglobulin peptides; or antibodies selected using in vitro methods, such as phage display, wherein the antibody repertoire is based on a feline immunoglobulin sequence. The term "feline antibody" denotes the genus of sequences that are feline sequences. Thus, the term is not designating the process by which the antibody was created, but the genus of sequences that are relevant.

In some embodiments, an anti-IL17A antibody comprises a feline heavy chain constant region selected from an IgG1a, IgG1b, and IgG2 constant region. In some embodiments, an anti-IL17A antibody is a feline IgG1a, IgG1b, or IgG2 antibody.

An "equine antibody" as used herein encompasses antibodies produced in an equine; antibodies produced in non-equine animals that comprise equine immunoglobulin genes or comprise equine immunoglobulin peptides; or antibodies selected using in vitro methods, such as phage display, wherein the antibody repertoire is based on an equine immunoglobulin sequence. The term "equine antibody" denotes the genus of sequences that are equine sequences. Thus, the term is not designating the process by which the antibody was created, but the genus of sequences that are relevant.

In some embodiments, an anti-IL17A antibody comprises an equine heavy chain constant region selected from an IgG1, IgG2, IgG3, IgG4, IgG5, IgG6 and IgG7 constant region. In some embodiments, an anti-IL17A antibody is an equine IgG1, IgG2, IgG3, IgG4, IgG5, IgG6 and IgG7 antibody.

A "caninized antibody" means an antibody in which at least one amino acid in a portion of a non-canine variable region has been replaced with the corresponding amino acid from a canine variable region. In some embodiments, a caninized antibody comprises at least one canine constant region (e.g., a γ constant region, an α constant region, a δ constant region, an ε constant region, a constant region, or etc.) or fragment thereof. In some embodiments, a caninized antibody is an antibody fragment, such as Fab, scFv, (Fab')₂, etc. The term "caninized" also denotes forms of non-canine (for example, murine) antibodies that are chimeric immunoglobulins, immunoglobulin chains, or fragments thereof (such as Fv, Fab, Fab', F(ab')2 or other antigen-binding sequences of antibodies) that contain minimal sequence of non-canine immunoglobulin. Caninized antibodies can include canine immunoglobulins (recipient antibody) in which residues from a CDR of the recipient are substituted by residues from a CDR of a non-canine species (donor antibody) such as mouse, rat, or rabbit having the desired specificity, affinity, and capacity. In some instances, Fv framework region (FR) residues of the canine immunoglobulin are replaced by corresponding non-canine residues. Furthermore, the caninized antibody can comprise residues that are found neither in the recipient antibody nor in the imported CDR or framework sequences, but are included to further refine and optimize antibody performance.

In some embodiments, at least one amino acid residue in a portion of a mouse variable heavy chain or a mouse variable light chain has been replaced with the corresponding amino acid from a canine variable region. In some embodiments, the modified chain is fused to a canine constant heavy chain or a canine constant light chain. In some embodiments, an anti-IL17A antibody comprises (a) a heavy chain sequence of SEQ ID NO: 15; (b) a heavy chain sequence of SEQ ID NO: 17; (c) a heavy chain sequence of SEQ ID NO: 18; (d) a heavy chain sequence of SEQ ID NO: 19; (e) a heavy chain sequence of SEQ ID NO: 20; or (f) a light chain sequence of SEQ ID NO: 16; or (g) a light chain sequence of SEQ ID NO: 21.

A "felinized antibody" means an antibody in which at least one amino acid in a portion of a non-feline variable region has been replaced with the corresponding amino acid from a feline variable region. In some embodiments, a felinized antibody comprises at least one feline constant region (e.g., a γ constant region, an α constant region, a δ constant region, an ε constant region, a constant region, or etc.) or fragment thereof. In some embodiments, a felinized antibody is an antibody fragment, such as Fab, scFv, (Fab')$_2$, etc. The term "felinized" also denotes forms of non-feline (for example, murine) antibodies that are chimeric immunoglobulins, immunoglobulin chains, or fragments thereof (such as Fv, Fab, Fab', F(ab')$_2$ or other antigen-binding sequences of antibodies) that contain minimal sequence of non-feline immunoglobulin. Felinized antibodies can include feline immunoglobulins (recipient antibody) in which residues from a CDR of the recipient are substituted by residues from a CDR of a non-feline species (donor antibody) such as mouse, rat, or rabbit having the desired specificity, affinity, and capacity. In some instances, Fv framework region (FR) residues of the feline immunoglobulin are replaced by corresponding non-feline residues. Furthermore, the felinized antibody can comprise residues that are found neither in the recipient antibody nor in the imported CDR or framework sequences, but are included to further refine and optimize antibody performance.

An "equinized antibody" means an antibody in which at least one amino acid in a portion of a non-equine variable region has been replaced with the corresponding amino acid from an equine variable region. In some embodiments, an equinized antibody comprises at least one equine constant region (e.g., a γ constant region, an α constant region, a δ constant region, an F constant region, a constant region, or etc.) or fragment thereof. In some embodiments, an equinized antibody is an antibody fragment, such as Fab, scFv, (Fab')$_2$, etc. The term "equinized" also denotes forms of non-equine (for example, murine) antibodies that are chimeric immunoglobulins, immunoglobulin chains, or fragments thereof (such as Fv, Fab, Fab', F(ab')$_2$ or other antigen-binding sequences of antibodies) that contain minimal sequence of non-equine immunoglobulin. Equinized antibodies can include equine immunoglobulins (recipient antibody) in which residues from a CDR of the recipient are substituted by residues from a CDR of a non-equine species (donor antibody) such as mouse, rat, or rabbit having the desired specificity, affinity, and capacity. In some instances, Fv framework region (FR) residues of the equine immunoglobulin are replaced by corresponding non-equine residues. Furthermore, the equinized antibody can comprise residues that are found neither in the recipient antibody nor in the imported CDR or framework sequences, but are included to further refine and optimize antibody performance.

In some embodiments, at least one amino acid residue in a portion of a mouse variable heavy chain or a mouse variable light chain has been replaced with the corresponding amino acid from an equine variable region. In some embodiments, the modified chain is fused to an equine constant heavy chain or a canine constant light chain.

The term "IgX Fc" means the Fc region is derived from a particular antibody isotype (e.g., IgG, IgA, IgD, IgE, IgM, etc.), where "X" denotes the antibody isotype. Thus, "IgG Fc" denotes the Fc region of a γ chain, "IgA Fc" denotes the Fc region of an α chain, "IgD Fc" denotes the Fc region of a δ chain, "IgE Fc" denotes the Fc region of an ε chain, "IgM Fc" denotes the Fc region of a chain, etc. In some embodiments, the IgG Fc region comprises CH1, hinge, CH2, CH3, and CL1. "IgX-N-Fc" denotes that the Fc region is derived from a particular subclass of antibody isotype (such as canine IgG subclass A, B, C, or D; feline IgG subclass 1a, 1b, or 2; or equine IgG subclass IgG1, IgG2, IgG3, IgG4, IgG5, IgG6, or IgG7, etc.), where "N" denotes the subclass. In some embodiments, IgX Fc or IgX-N-Fc regions are derived from a companion animal, such as a dog, a cat, or a horse. In some embodiments, IgG Fc regions are isolated from canine 7 heavy chains, such as IgG-A, IgG-B, IgG-C, or IgG-D. In some instances, IgG Fc regions are isolated from feline 7 heavy chains, such as IgG1a, IgG1b, or IgG2. Antibodies comprising an Fc region of IgG-A, IgG-B, IgG-C, or IgG-D may provide for higher expression levels in recombination production systems.

As used herein, "percent (%) amino acid sequence identity" and "homology" with respect to a peptide, polypeptide, or antibody sequence are defined as the percentage of amino acid residues in a candidate sequence that are identical with the amino acid residues in the specific peptide or polypeptide sequence, after aligning the sequences and introducing gaps, if necessary to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, or MEGALINE (DNASTAR) software. Those skilled in the art can determine appropriate parameters for measuring alignment, including any algorithms needed to achieve maximal alignment over the full length of sequences being compared.

An amino acid substitution may include but is not limited to the replacement of one amino acid in a polypeptide with another amino acid. Exemplary substitutions are shown in Table 2. Amino acid substitutions may be introduced into an antibody of interest and the products screened for a desired activity, for example, retained/improved antigen binding, decreased immunogenicity, or improved ADCC or CDC.

TABLE 2

| Original Residue | Exemplary Substitutions |
|---|---|
| Ala (A) | Val; Leu; Ile |
| Arg (R) | Lys; Gln; Asn |
| Asn (N) | Gln; His; Asp; Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |

TABLE 2-continued

| Original Residue | Exemplary Substitutions |
| --- | --- |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes with another class.

In some embodiments, an anti-IL17A antibody comprises a heavy chain and a light chain, wherein:

(a) (i) the heavy chain comprises a CDR-H1 sequence having at least 85%, at least 90%, at least 95, or at least 98% sequence identity to the amino acid sequence of the amino acid sequence of SEQ ID NO: 1, a CDR-H2 sequence having at least 85%, at least 90%, at least 95, or at least 98% sequence identity to the amino acid sequence of the amino acid sequence of SEQ ID NO: 2, and a CDR-H3 sequence having at least 85%, at least 90%, at least 95, or at least 98% sequence identity to the amino acid sequence of the amino acid sequence of SEQ ID NO: 3, and (ii) the light chain comprises a CDR-L1 sequence having at least 85%, at least 90%, at least 95, or at least 98% sequence identity to the amino acid sequence of the amino acid sequence of SEQ ID NO: 8, a CDR-L2 sequence having at least 85%, at least 90%, at least 95, or at least 98% sequence identity to the amino acid sequence of the amino acid sequence of SEQ ID NO: 9 or SEQ ID NO: 108, and a CDR-L3 sequence having at least 85%, at least 90%, at least 95, or at least 98% sequence identity to the amino acid sequence of the amino acid sequence of SEQ ID NO: 10; or (b) (i) the heavy chain comprises a CDR-H1 sequence having at least 85%, at least 90%, at least 95, or at least 98% sequence identity to the amino acid sequence of the amino acid sequence of SEQ ID NO: 52, a CDR-H2 sequence having at least 85%, at least 90%, at least 95, or at least 98% sequence identity to the amino acid sequence of the amino acid sequence of SEQ ID NO: 53 or SEQ ID NO: 109, and a CDR-H3 sequence having at least 85%, at least 90%, at least 95, or at least 98% sequence identity to the amino acid sequence of the amino acid sequence of SEQ ID SEQ ID NO: 54, and (ii) the light chain comprises a CDR-L1 sequence having at least 85%, at least 90%, at least 95, or at least 98% sequence identity to the amino acid sequence of the amino acid sequence of SEQ ID NO: 59 or SEQ ID NO: 111, a CDR-L2 sequence having at least 85%, at least 90%, at least 95, or at least 98% sequence identity to the amino acid sequence of the amino acid sequence of SEQ ID NO: 60 or SEQ ID NO: 112, and a CDR-L3 sequence having at least 85%, at least 90%, at least 95, or at least 98% sequence identity to the amino acid sequence of the amino acid sequence of SEQ ID NO: 61; or (c) (i) the heavy chain comprises a CDR-H1 sequence having at least 85%, at least 90%, at least 95, or at least 98% sequence identity to the amino acid sequence of the amino acid sequence of SEQ ID NO: 66, a CDR-H2 sequence having at least 85%, at least 90%, at least 95, or at least 98% sequence identity to the amino acid sequence of the amino acid sequence of SEQ ID NO: 67 or SEQ ID NO: 114, and a CDR-H3 sequence having at least 85%, at least 90%, at least 95, or at least 98% sequence identity to the amino acid sequence of the amino acid sequence of SEQ ID NO: 68, and (ii) the light chain comprises a CDR-L1 sequence having at least 85%, at least 90%, at least 95, or at least 98% sequence identity to the amino acid sequence of the amino acid sequence of SEQ ID NO: 73 or SEQ ID NO: 116, a CDR-L2 sequence having at least 85%, at least 90%, at least 95, or at least 98% sequence identity to the amino acid sequence of the amino acid sequence of SEQ ID NO: 74 or SEQ ID NO: 117; and a CDR-L3 sequence having at least 85%, at least 90%, at least 95, or at least 98% sequence identity to the amino acid sequence of the amino acid sequence of SEQ ID NO: 75; or (d) (i) the heavy chain comprises a CDR-H1 sequence having at least 85%, at least 90%, at least 95, or at least 98% sequence identity to the amino acid sequence of the amino acid sequence of SEQ ID NO: 80, a CDR-H2 sequence having at least 85%, at least 90%, at least 95, or at least 98% sequence identity to the amino acid sequence of the amino acid sequence of SEQ ID NO: 81 or SEQ ID NO: 119, and a CDR-H3 sequence having at least 85%, at least 90%, at least 95, or at least 98% sequence identity to the amino acid sequence of the amino acid sequence of SEQ ID NO: 82, and (ii) the light chain comprises a CDR-L1 sequence having at least 85%, at least 90%, at least 95, or at least 98% sequence identity to the amino acid sequence of the amino acid sequence of SEQ ID NO: 87 or SEQ ID NO: 121, a CDR-L2 sequence having at least 85%, at least 90%, at least 95, or at least 98% sequence identity to the amino acid sequence of the amino acid sequence of SEQ ID NO: 88 or SEQ ID NO: 122, and a CDR-L3 sequence having at least 85%, at least 90%, at least 95, or at least 98% sequence identity to the amino acid sequence of the amino acid sequence of SEQ ID NO: 89.

In some embodiments, an anti-IL17A antibody comprises a heavy chain and a light chain, wherein:

(a) (i) a variable light chain sequence having at least 85%, at least 90%, at least 95%, or at least 98% sequence identity to the amino acid sequence of SEQ ID NO: 24;

(ii) a variable heavy chain sequence having at least 85%, at least 90%, at least 95%, or at least 98% sequence identity to the amino acid sequence of SEQ ID NO: 25; or (iii) a variable light chain sequence as in (i) and a variable heavy chain sequence as in (ii); or (b) (i) a variable light chain sequence having at least 85%, at least 90%, at least 95%, or at least 98% sequence identity to the amino acid sequence of SEQ ID NO: 16;
(ii) a variable heavy chain sequence having at least
85%, at least 90%, at least 95%, or at least 98%
sequence identity to the amino acid sequence of SEQ
ID NO: 15; or (iii) a variable light chain sequence as in
(i) and a variable heavy chain sequence as in (ii); or
(c) (i) a variable light chain sequence having at least 85%,
at least 90%, at least 95%, or at least 98% sequence
identity to the amino acid sequence of SEQ ID NO: 34;
(ii) a variable heavy chain sequence having at least
85%, at least 90%, at least 95%, or at least 98%
sequence identity to the amino acid sequence of SEQ
ID NO: 35; or (iii) a variable light chain sequence as in
(i) and a variable heavy chain sequence as in (ii); or
(d) (i) a variable light chain sequence having at least 85%,
at least 90%, at least 95%, or at least 98% sequence
identity to the amino acid sequence of SEQ ID NO: 38;
(ii) a variable heavy chain sequence having at least
85%, at least 90%, at least 95%, or at least 98%
sequence identity to the amino acid sequence of SEQ
ID NO: 39; or (iii) a variable light chain sequence as in
(i) and a variable heavy chain sequence as in (ii); or
(e) (i) a variable light chain sequence having at least 85%,
at least 90%, at least 95%, or at least 98% sequence
identity to the amino acid sequence of SEQ ID NO: 36;
(ii) a variable heavy chain sequence having at least
85%, at least 90%, at least 95%, or at least 98%
sequence identity to the amino acid sequence of SEQ
ID NO: 37; or (iii) a variable light chain sequence as in
(i) and a variable heavy chain sequence as in (ii).

Exemplary IL17Ra Polypeptides

"IL17Ra," as used herein, is a polypeptide comprising the
entirety or a fragment of IL17A receptor that binds to
IL17A.

For example, "IL17Ra" refers to an IL17Ra polypeptide
from any vertebrate source, including mammals such as
primates (e.g., humans and cynomolgus monkeys), rodents
(e.g., mice and rats), and companion animals (e.g., dogs,
cats, and equine), unless otherwise indicated. In some
embodiments, IL17Ra is an extracellular domain fragment
that binds IL17A. In some such embodiments, the IL17Ra
may be referred to as an IL17Ra extracellular domain
(ECD). In some embodiments, IL4R comprises the amino
acid sequence of SEQ ID NO: 32, SEQ ID NO: 33, SEQ ID
NO: SEQ ID NO: 94, SEQ ID NO: 97, SEQ ID NO: 98, or
SEQ ID NO: 99.

An "extracellular domain" ("ECD") is the portion of a
polypeptide that extends beyond the transmembrane domain
into the extracellular space. The term "extracellular
domain," as used herein, may comprise a complete extra-
cellular domain or may comprise a truncated extracellular
domain missing one or more amino acids, that binds to its
ligand. The composition of the extracellular domain may
depend on the algorithm used to determine which amino
acids are in the membrane. Different algorithms may predict,
and different systems may express, different extracellular
domains for a given protein.

An extracellular domain of an IL17Ra polypeptide may
comprise a complete extracellular domain or a truncated
extracellular domain of IL17Ra that binds IL17A. As used
herein, the terms "extracellular domain of an IL17Ra poly-
peptide," "IL17Ra ECD," and similar terms refer to an
IL17Ra polypeptide that does not comprise a transmem-
brane domain or cytoplasmic domain, even if the term
follows an open transitional word, such as "comprising,"
"comprises," and the like. In some embodiments, an extra-
cellular domain of an IL17Ra polypeptide is an extracellular domain of an IL17Ra polypeptide derived from a companion
species animal or a human. For example, in some embodi-
ments, an extracellular domain of an IL17Ra polypeptide is
derived from canine IL17Ra, feline IL17Ra or equine
IL17Ra. In some embodiments, an extracellular domain of
an IL17Ra polypeptide comprises the amino acid sequence
of SEQ ID NO: 33, SEQ ID NO: 94, SEQ ID NO: 97, SEQ
ID NO: 98, SEQ ID NO: 99, or any fragment thereof.

A polypeptide of the invention may comprise an extra-
cellular domain of an IL17Ra polypeptide, wherein the
polypeptides are derived from a human or a companion
animal species. For example, a polypeptide may comprise an
extracellular domain of an IL17Ra polypeptide from a
human, a dog, a cat, or a horse.

Polypeptides comprising an extracellular domain of an
IL17Ra polypeptide can function as decoy receptors for
trapping IL17A and inhibiting its interaction with IL17Ra on
cell surfaces. Decoy receptors, such as those of the inven-
tion, recognize their ligands with high affinity and specificity
but are structurally incapable of signaling. They compete
with wild-type receptors for ligand binding and participate
in ligand/receptor interactions, thus modulating the activity
of or the number of functioning receptors and/or the cellular
activity downstream from the receptors. Decoy receptors
can act as molecular traps for agonist ligands and thereby
inhibit ligand-induced receptor activation.

"Wild-type" refers to a non-mutated version of a poly-
peptide that occurs in nature, or a fragment thereof. A
wild-type polypeptide may be produced recombinantly. A
"wild-type IL17Ra ECD" refers to a protein having an
amino acid sequence that is identical to the same portion of
an extracellular domain of an IL17Ra that occurs in nature.

A "variant," as used herein is a polypeptide that differs
from a reference polypeptide by single or multiple amino
acid substitutions, deletions, and/or additions and substan-
tially retains at least one biological activity of the reference
polypeptide.

A "biologically active" entity, or an entity having "bio-
logical activity," is an entity having any function related to
or associated with a metabolic or physiological process,
and/or having structural, regulatory, or biochemical func-
tions of a naturally-occurring molecule. Biologically active
polynucleotide fragments are those exhibiting similar activ-
ity, but not necessarily identical, to an activity of a poly-
nucleotide of the present invention. A biologically active
polypeptide or fragment thereof includes one that can par-
ticipate in a biological reaction, including, but not limited to,
a ligand-receptor interaction or antigen-antibody binding.
The biological activity can include an improved desired
activity, or a decreased undesirable activity. An entity may
demonstrate biological activity when it participates in a
molecular interaction with another molecule, such as hybrid-
ization, when it has therapeutic value in alleviating a disease
condition, when it has prophylactic value in inducing an
immune response, when it has diagnostic and/or prognostic
value in determining the presence of a molecule, such as a
biologically active fragment of a polynucleotide that may be
detected as unique for the polynucleotide molecule, and
when it can be used as a primer in a polymerase chain
reaction (PCR).

In some embodiments, a variant has at least about 50%
amino acid sequence identity, at least about 60% amino acid
sequence identity, at least about 65% amino acid sequence
identity, at least about 70% amino acid sequence identity, at
least about 75% amino acid sequence identity, at least about
80% amino acid sequence identity, at least about 85% amino
acid sequence identity, at least about 90% amino acid sequence identity, at least about 95% amino acid sequence identity, or at least 99% amino acid sequence identity with the native sequence polypeptide.

In some embodiments, an IL17Ra ECD polypeptide has at least 85%, at least 90%, at least 95%, at least 98% sequence identity to the amino acid sequence of SEQ ID NO: 33, SEQ ID NO: 94, SEQ ID NO: 97, SEQ ID NO: 98, or SEQ ID NO: 99.

Exemplary IgG Fc Variants

Novel IgG Fc variants are provided, for example IgG Fc variants with altered binding affinity (e.g., reduced binding affinity) to C1q and CD16.

A "fragment crystallizable polypeptide" or "Fc polypeptide" is the portion of an antibody molecule that interacts with effector molecules and cells. It comprises the C-terminal portions of the immunoglobulin heavy chains. As used herein, an Fc polypeptide includes fragments of the Fc domain having one or more biological activity of an entire Fc polypeptide.

An "IgG Fc variant" as used herein is an IgG Fc polypeptide that differs from a reference IgG Fc polypeptide by single or multiple amino acid substitutions, deletions, and/or additions and substantially retains at least one biological activity of the reference IgG Fc polypeptide.

In some embodiments, an IgG Fc variant may have reduced complement fixation and/or antibody-dependent cellular cytotoxicity (ADCC) induction. In some embodiments, an IgG Fc variant has reduced binding affinity to C1q and/or CD16.

In some embodiments, an IgG Fc variant polypeptide comprises an amino acid substitution at a position corresponding to position 110 of SEQ ID NO: 45 or at a position corresponding to position 108 of SEQ ID NO: 46. In some embodiments, an IgG Fc variant polypeptide comprises an amino acid substitution at a position corresponding to position 55 of SEQ ID NO: 45 or at a position corresponding to position 43 of SEQ ID NO: 46. In some embodiments, an IgG Fc variant polypeptide comprises an amino acid substitution at a position corresponding to position 114 of SEQ ID NO: 45 or at a position corresponding to position 112 of SEQ ID NO: 46. In some embodiments, an IgG Fc variant polypeptide comprises an amino acid substitution at a position corresponding to position 115 at SEQ ID NO: 45 or at a position corresponding to position 113 of SEQ ID NO: 46.

In some embodiments, an IgG Fc variant polypeptide comprises an amino acid substitution at position 110 of SEQ ID NO: 45 or at position 108 of SEQ ID NO: 46. In some embodiments, an IgG Fc variant polypeptide comprises an amino acid substitution at position 55 of SEQ ID NO: 45 or at position 43 of SEQ ID NO: 46. In some embodiments, an IgG Fc variant polypeptide comprises an amino acid substitution at position 114 of SEQ ID NO: 45 or at position 112 of SEQ ID NO: 46. In some embodiments, an IgG Fc variant polypeptide comprises an amino acid substitution at position 115 at SEQ ID NO: 45 or at position 113 of SEQ ID NO: 46.

In some embodiments, an IgG Fc variant polypeptide comprises an arginine at position 110 of SEQ ID NO: 45 or at position 108 of SEQ ID NO: 46. In some embodiments, an IgG Fc variant polypeptide comprises a glycine at position 55 of SEQ ID NO: 45 or at position 43 of SEQ ID NO: 46. In some embodiments, an IgG Fc variant polypeptide comprises an isoleucine at position 114 of SEQ ID NO: 45 or at position 112 of SEQ ID NO: 46. In some embodiments, an IgG Fc variant polypeptide comprises a glycine at position 115 at SEQ ID NO: 45 or at position 113 of SEQ ID NO: 46.

In some embodiments, an IgG Fc variant polypeptide comprises the amino acid sequence of SEQ ID NO: 47, SEQ ID NO: 48, SEQ ID NO: 49, or SEQ ID NO: 50. In some embodiments, the polypeptide comprising an IgG Fc variant polypeptide comprises the amino acid sequence of SEQ ID NO: 96.

An "amino acid derivative," as used herein, refers to any amino acid, modified amino acid, and/or amino acid analogue, that is not one of the 20 common natural amino acids found in humans. Exemplary amino acid derivatives include natural amino acids not found in humans (e.g., seleno cysteine and pyrrolysine, which may be found in some microorganisms) and unnatural amino acids. Exemplary amino acid derivatives, include, but are not limited to, amino acid derivatives commercially available through chemical product manufacturers and distributors (e.g., sigmaaldrich. com, accessed on May 6, 2017, which is incorporated herein by reference). One or more amino acid derivative maybe incorporated into a polypeptide at a specific location using translation systems that utilize host cells, orthogonal aminoacyl-tRNA synthetases derived from eubacterial synthetases, orthogonal tRNAs, and an amino acid derivative. For further descriptions, see, e.g., U.S. Pat. No. 9,624,485.

In some embodiments, an IgG Fc variant polypeptide or other polypeptide described herein comprises an amino acid substitution with an amino acid derivative.

A "fusion partner," as used herein, refers to an additional component of a polypeptide, such as albumin, an albumin binding fragment, or a fragment of an immunoglobulin molecule. A fusion partner may comprise an oligomerization domain such as an Fc domain of a heavy chain immunoglobulin.

In some embodiments, an IgG Fc variant polypeptide is a fusion partner to an IL17A antibody or IL17Ra ECD polypeptide as described herein. In some embodiments, a polypeptide comprises an IgG Fc variant polypeptide and an IL17A antibody and/or IL17Ra ECD polypeptide as described herein. In some embodiments, a polypeptide comprises an IgG Fc variant polypeptide and another polypeptide. In some embodiments, a polypeptide comprises the amino acid sequence of SEQ ID NO: 96.

Exemplary Target Binding Affinity

The term "affinity" means the strength of the sum total of noncovalent interactions between a single binding site of a molecule (for example, an antibody) and its binding partner (for example, an antigen). The affinity of a molecule X for its partner Y can generally be represented by the dissociation constant ($K_d$). Affinity can be measured by common methods known in the art, such as, for example, immunoblot, ELISA KD, KinEx A, biolayer interferometry (BLI), or surface plasmon resonance devices.

The terms "$K_d$," "KD," "$K_d$" or "$K_d$ value" as used interchangeably to refer to the equilibrium dissociation constant of an antibody-antigen interaction. In some embodiments, the $K_d$ of the antibody is measured by using biolayer interferometry assays using a biosensor, such as an OCTET System (Pall ForteBio LLC, Fremont, CA) according to the supplier's instructions. Briefly, biotinylated antigen is bound to the sensor tip and the association of antibody is monitored for ninety seconds and the dissociation is monitored for 600 seconds. The buffer for dilutions and binding steps is 20 mM phosphate, 150 mM NaCl, pH 7.2. A buffer only blank curve is subtracted to correct for any drift. The data are fit to a 1:1 binding model using FORTEBIO data analysis software to determine association rate constant ($k_{on}$), dissociation rate constant ($k_{off}$), and the $K_d$. The equilibrium dissociation constant ($K_d$) is calculated as the ratio of $k_{off}/k_{on}$. The term "$k_{on}$" refers to the rate constant for association of an antibody to an antigen and the term "$k_{off}$" refers to the rate constant for dissociation of an antibody from the antibody/antigen complex.

The term "binds" to an antigen or epitope is a term that is well understood in the art, and methods to determine such binding are also well known in the art. A molecule is said to exhibit "binding" if it reacts, associates with, or has affinity for a particular cell or substance and the reaction, association, or affinity is detectable by one or more methods known in the art, such as, for example, immunoblot, ELISA KD, KinEx A, biolayer interferometry (BLI), surface plasmon resonance devices, or etc.

"Surface plasmon resonance" denotes an optical phenomenon that allows for the analysis of real-time biospecific interactions by detection of alterations in protein concentrations within a biosensor matrix, for example using the BIACORE system (BIAcore International AB, a GE Healthcare company, Uppsala, Sweden and Piscataway, N.J.). For further descriptions, see Jonsson et al. (1993) *Ann. Biol. Clin.* 51: 19-26.

"Biolayer interferometry" refers to an optical analytical technique that analyzes the interference pattern of light reflected from a layer of immobilized protein on a biosensor tip and an internal reference layer. Changes in the number of molecules bound to the biosensor tip cause shifts in the interference pattern that can be measured in real-time. A nonlimiting exemplary device for biolayer interferometry is an OCTET system (Pall ForteBio LLC). See, e.g., Abdiche et al., 2008, *Anal. Biochem.* 377: 209-277.

In some embodiments, an anti-IL17A antibody or an IL17Ra ECD binds to IL17A, such as canine IL17A, feline IL17A, or equine IL17A with a dissociation constant ($K_d$) of less than $5 \times 10^{-6}$ M, less than $1 \times 10^{-6}$ M, less than $5 \times 10^{-7}$ M, less than $1 \times 10^{-7}$ M, less than $5 \times 10^{-8}$ M, less than $1 \times 10^{-8}$ M, less than $5 \times 10^{-9}$ M, less than $1 \times 10^{-9}$ M, less than $5 \times 10^{-10}$ M, less than $1 \times 10^{-10}$ M, less than $5 \times 10^{-11}$ M, less than $1 \times 10^{-11}$ M, less than $5 \times 10^{-12}$ M, or less than $1 \times 10^{-12}$ M, as measured by biolayer interferometry. In some embodiments, an anti-IL17A antibody or an IL17Ra ECD binds to canine IL17A, feline IL17A, or equine IL17A with a $K_d$ of between $5 \times 10^{-6}$ M and $1 \times 10^{-6}$ M, between $5 \times 10^{-6}$ M and $5 \times 10^{-7}$ M, between $5 \times 10^{-6}$ M and $1 \times 10^{-7}$ M, between $5 \times 10^{-6}$ M and $5 \times 10^{-8}$ M, $5 \times 10^{-6}$ M and $1 \times 10^{-8}$ M, between $5 \times 10^{-6}$ M and $5 \times 10^{-9}$ M, between $5 \times 10^{-6}$ M and $1 \times 10^{-9}$ M, between $5 \times 10^{-6}$ M and $5 \times 10^{-10}$ M, between $5 \times 10^{-6}$ M and $1 \times 10^{-10}$ M, between $5 \times 10^{-6}$ M and $5 \times 10^{-11}$ M, between $5 \times 10^{-6}$ M and $1 \times 10^{-11}$ M, between $5 \times 10^{-6}$ M and $5 \times 10^{-12}$ M, between $5 \times 10^{-6}$ M and $1 \times 10^{-12}$ M, between $1 \times 10^{-6}$ M and $5 \times 10^{-7}$ M, between $1 \times 10^{-6}$ M and $1 \times 10^{-7}$ M, between $1 \times 10^{-6}$ M and $5 \times 10^{-8}$ M, $1 \times 10^{-6}$ M and $1 \times 10^{-8}$ M, between $1 \times 10^{-6}$ M and $5 \times 10^{-9}$ M, between $1 \times 10^{-6}$ M and $1 \times 10^{-9}$ M, between $1 \times 10^{-6}$ M and $5 \times 10^{-10}$ M, between $1 \times 10^{-6}$ M and $1 \times 10^{-10}$ M, between $1 \times 10^{-6}$ M and $5 \times 10^{-11}$ M, between $1 \times 10^{-6}$ M and $1 \times 10^{-11}$ M, between $1 \times 10^{-6}$ M and $5 \times 10^{-12}$ M, between $1 \times 10^{-6}$ M and $1 \times 10^{-12}$ M, between $5 \times 10^{-7}$ M and $1 \times 10^{-7}$ M, between $5 \times 10^{-7}$ M and $5 \times 10^{-8}$ M, $5 \times 10^{-7}$ M and $1 \times 10^{-8}$ M, between $5 \times 10^{-7}$ M and $5 \times 10^{-9}$ M, between $5 \times 10^{-7}$ M and $1 \times 10^{-9}$ M, between $5 \times 10^{-7}$ M and $5 \times 10^{-10}$ M, between $5 \times 10^{-7}$ M and $1 \times 10^{-10}$ M, between $5 \times 10^{-7}$ M and $5 \times 10^{-11}$ M, between $5 \times 10^{-7}$ M and $1 \times 10^{-11}$ M, between $5 \times 10^{-7}$ M and $5 \times 10^{-12}$ M, between $5 \times 10^{-7}$ M and $1 \times 10^{-12}$ M, between $1 \times 10^{-7}$ M and $5 \times 10^{-8}$ M, $1 \times 10^{-7}$ M and $1 \times 10^{-8}$ M, between $1 \times 10^{-7}$ M and $5 \times 10^{-9}$ M, between $1 \times 10^{-7}$ M and $1 \times 10^{-9}$ M, between $1 \times 10^{-7}$ M and $5 \times 10^{-10}$ M, between $1 \times 10^{-7}$ M and $1 \times 10^{-10}$ M, between $1 \times 10^{-7}$ M and $5 \times 10^{-11}$ M, between $1 \times 10^{-7}$ M and $1 \times 10^{-11}$ M, between $1 \times 10^{-7}$ M and $5 \times 10^{-12}$ M, between $1 \times 10^{-7}$ M and $1 \times 10^{-12}$ M, between $5 \times 10^{-8}$ M and $1 \times 10^{-8}$ M, between $5 \times 10^{-8}$ M and $5 \times 10^{-9}$ M, between $5 \times 10^{-8}$ M and $1 \times 10^{-9}$ M, between $5 \times 10^{-8}$ M and $5 \times 10^{-10}$ M, between $5 \times 10^{-8}$ M and $1 \times 10^{-10}$ M, between $5 \times 10^{-8}$ M and $5 \times 10^{-11}$ M, between $5 \times 10^{-8}$ M and $1 \times 10^{-11}$ M, between $5 \times 10^{-8}$ M and $5 \times 10^{-12}$ M, between $5 \times 10^{-8}$ M and $1 \times 10^{-12}$ M, $1 \times 10^{-8}$ M and $5 \times 10^{-9}$ M, between $1 \times 10^{-8}$ M and $1 \times 10^{-9}$ M, between $1 \times 10^{-8}$ M and $5 \times 10^{-10}$ M, between $1 \times 10^{-8}$ M and $1 \times 10^{-10}$ M, between $1 \times 10^{-8}$ M and $5 \times 10^{-11}$ M, between $1 \times 10^{-8}$ M and $1 \times 10^{-11}$ M, between $1 \times 10^{-8}$ M and $5 \times 10^{-12}$ M, between $1 \times 10^{-8}$ M and $1 \times 10^{-12}$ M, between $5 \times 10^{-9}$ M and $1 \times 10^{-9}$ M, between $5 \times 10^{-9}$ M and $5 \times 10^{-10}$ M, between $5 \times 10^{-9}$ M and $1 \times 10^{-10}$ M, between $5 \times 10^{-9}$ M and $5 \times 10^{-11}$ M, between $5 \times 10^{-9}$ M and $1 \times 10^{-11}$ M, between $5 \times 10^{-9}$ M and $5 \times 10^{-12}$ M, between $5 \times 10^{-9}$ M and $1 \times 10^{-12}$ M, between $1 \times 10^{-9}$ M and $5 \times 10^{-10}$ M, between $1 \times 10^{-9}$ M and $1 \times 10^{-10}$ M, between $1 \times 10^{-9}$ M and $5 \times 10^{-11}$ M, between $1 \times 10^{-9}$ M and $1 \times 10^{-11}$ M, between $1 \times 10^{-9}$ M and $5 \times 10^{-12}$ M, between $1 \times 10^{-9}$ M and $1 \times 10^{-12}$ M, between $5 \times 10^{-1\circ}$ M and $1 \times 10^{-10}$ M, between $5 \times 10^{-1\circ}$ M and $5 \times 10^{-11}$ M, between, $1 \times 10^{-10}$ M and $5 \times 10^{-11}$ M, $1 \times 10^{-10}$ M and $1 \times 10^{-11}$ M, between $1 \times 10^{-10}$ M and $5 \times 10^{-12}$ M, between $1 \times 10^{-10}$ M and $1 \times 10^{-12}$ M, between $5 \times 10^{-11}$ M and $1 \times 10^{-12}$ M, between $5 \times 10^{-11}$ M and $5 \times 10^{-12}$ M, between $5 \times 10^{-11}$ M and $1 \times 10^{-12}$ M, between $1 \times 10^{-11}$ M and $5 \times 10^{-12}$ M, or between $1 \times 10^{-11}$ M and $1 \times 10^{-12}$ M, as measured by biolayer interferometry. In some embodiments, an anti-IL17A antibody or IL17Ra ECD binds to canine IL17A, feline IL17A, or equine IL17A, as determined by immunoblot analysis.

In some embodiments, an anti-IL17A antibody is provided that competes with an anti-IL17A antibody described herein (such as Clone C, Clone A, Clone D, or Clone E) for binding to IL17A. In some embodiments, an antibody that competes with binding with any of the antibodies provided herein can be made or used. In some embodiments, an anti-IL17A antibody is provided that competes with monoclonal Clone C, Clone A, Clone D, or Clone E antibody in binding to canine IL17A, feline IL17A, or equine IL17A.

The term "IL17A signaling function" refers to any one of or combination of the downstream activities that occurs when IL17A binds its receptor or receptor complex.

In some embodiments, the IL17A signaling function comprises activation of NFκB, MAPKs and/or C/EBPs to induce cytokines, chemokines, and/or host defense to microbial infection. In some embodiments, the IL17A signaling function comprises activating production of IL6.

To "reduce" or "inhibit" means to decrease, reduce, or arrest an activity, function, or amount as compared to a reference. In some embodiments, by "reduce" or "inhibit" is meant the ability to cause an overall decrease of 20% or greater. In some embodiments, by "reduce" or "inhibit" is meant the ability to cause an overall decrease of 50% or greater. In some embodiments, by "reduce" or "inhibit" is meant the ability to cause an overall decrease of 75%, 85%, 90%, 95%, or greater. In some embodiments, the amount noted above is inhibited or decreased over a period of time, relative to a control dose (such as a placebo) over the same period of time.

To "increase" or "stimulate" means to increase, improve, or augment an activity, function, or amount as compared to a reference. In some embodiments, by "reduce" or "inhibit" is meant the ability to cause an overall increase of 20% or greater. In some embodiments, by "increase" or "stimulate" is meant the ability to cause an overall increase of 50% or greater. In some embodiments, by "increase" or "stimulate" is meant the ability to cause an overall increase of 75%, 85%, 90%, 95%, or greater. In some embodiments, the amount noted above is stimulated or increased over a period of time, relative to a control dose (such as a placebo) over the same period of time.

A "reference" as used herein, refers to any sample, standard, or level that is used for comparison purposes. A reference may be obtained from a healthy or non-diseased sample. In some examples, a reference is obtained from a non-diseased or non-treated sample of a companion animal. In some examples, a reference is obtained from one or more healthy animals of a particular species, which are not the animal being tested or treated.

The term "substantially reduced," as used herein, denotes a sufficiently high degree of reduction between a numeric value and a reference numeric value such that one of skill in the art would consider the difference between the two values to be of statistical significance within the context of the biological characteristic measured by said values. In some embodiments, the substantially reduced numeric values is reduced by greater than about any one of 10%, 15% 20%, 25%, 30%, 35%, 40%, 45%, 50%, 60%, 70%, 80%, 90%, or 100% compared to the reference value.

In some embodiments, an IL17A antibody or an IL17Ra ECD polypeptide may reduce IL17A signaling function in a companion animal species by at least 10%, at least 15%, at least 20%, at least 25%, at least 30%, at least 35%, at least 40%, at least 45%, at least 50%, at least 60%, at least 70%, at least 80%, at least 90%, or 100% compared to IL17A signaling function in the absence of the IL17A antibody or IL17Ra ECD polypeptide, as measured by a reduction in IL6 production. In some embodiments, the reduction in IL17A signaling function or the reduction in IL6 production is between 10% and 15%, between 10% and 20%, between 10% and 25%, between 10% and 30%, between 10% and 35%, between 10% and 40%, between 10% and 45%, between 10% and 50%, between 10% and 60%, between 10% and 70%, between 10% and 80%, between 10% and 90%, between 10% and 100%, between 15% and 20%, between 15% and 25%, between 15% and 30%, between 15% and 35%, between 15% and 40%, between 15% and 45%, between 15% and 50%, between 15% and 60%, between 15% and 70%, between 15% and 80%, between 15% and 90%, between 15% and 100%, between 20% and 25%, between 20% and 30%, between 20% and 35%, between 20% and 40%, between 20% and 45%, between 20% and 50%, between 20% and 60%, between 20% and 70%, between 20% and 80%, between 20% and 90%, between 20% and 100%, between 25% and 30%, between 25% and 35%, between 25% and 40%, between 25% and 45%, between 25% and 50%, between 25% and 60%, between 25% and 70%, between 25% and 80%, between 25% and 90%, between 25% and 100%, between 30% and 35%, between 30% and 40%, between 30% and 45%, between 30% and 50%, between 30% and 60%, between 30% and 70%, between 30% and 80%, between 30% and 90%, between 30% and 100%, between 35% and 40%, between 35% and 45%, between 35% and 50%, between 35% and 60%, between 35% and 70%, between 35% and 80%, between 35% and 90%, between 35% and 100%, between 40% and 45%, between 40% and 50%, between 40% and 60%, between 40% and 70%, between 40% and 80%, between 40% and 90%, between 40% and 100%, between 45% and 50%, between 45% and 60%, between 45% and 70%, between 45% and 80%, between 45% and 90%, between 45% and 100%, between 50% and 60%, between 50% and 70%, between 50% and 80%, between 50% and 90%, between 50% and 100%, between 60% and 70%, between 60% and 80%, between 60% and 90%, between 60% and 100%, between 70% and 80%, between 70% and 90%, between 70% and 100%, between 80% and 90%, between 80% and 100%, or between 90% and 100%.

Exemplary Antibody and Polypeptide Expression and Production

Polynucleotide sequences that encode all or part of a polypeptide with or without a signal sequence are provided. If a homologous signal sequence (e.g., a signal sequence of native IL-17Ra) is not used in the construction of the nucleic acid molecule, then another signal sequence may be used, for example, any one of the signal sequences described in PCT US06/02951.

Typically, nucleotide sequence encoding the polypeptide of interest, such as an IL17A antibody, an IL17Ra ECD polypeptide, an IgG Fc variant polypeptide, or a polypeptide comprising such, is inserted into an expression vector, suitable for expression in a selected host cell.

The term "vector" is used to describe a polynucleotide that can be engineered to contain a cloned polynucleotide or polynucleotides that can be propagated in a host cell. A vector can include one or more of the following elements: an origin of replication, one or more regulatory sequences (such as, for example, promoters or enhancers) that regulate the expression of the polypeptide of interest, or one or more selectable marker genes (such as, for example, antibiotic resistance genes and genes that can be used in colorimetric assays, for example, β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6@cells (Crucell), 293 cells, and CHO cells, and their derivatives, such as 293-6E, DG44, CHO-S, and CHO-K cells. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) encoding an amino acid sequence(s) provided herein.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, for example, in the case of an RNA polynucleotide. Thus, a DNA polynucleotide that is contained in a vector inside a host cell may be referred to as "isolated." In some embodiments, an IL17A antibody, an IL17Ra ECD polypeptide, an IgG Fc variant polypeptide, or a polypeptide comprising such, is purified using chromatography, such as size exclusion chromatography, ion exchange chromatography, protein A column chromatography, hydrophobic interaction chromatography, and CHT chromatography.

Exemplary Pharmaceutical Compositions

The terms "pharmaceutical formulation" and "pharmaceutical composition" refer to a preparation which is in such form as to permit the biological activity of the active ingredient(s) to be effective, and which contains no additional components that are unacceptably toxic to a subject to which the formulation would be administered.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. Examples of pharmaceutically acceptable carriers include alumina; aluminum stearate; lecithin; serum proteins, such as human serum albumin, canine or other animal albumin; buffers such as phosphate, citrate, tromethamine or HEPES buffers; glycine; sorbic acid; potassium sorbate; partial glyceride mixtures of saturated vegetable fatty acids; water; salts or electrolytes, such as protamine sulfate, disodium hydrogen phosphate, potassium hydrogen phosphate, sodium chloride, zinc salts, colloidal silica, or magnesium trisilicate; polyvinyl pyrrolidone, cellulose-based substances; polyethylene glycol; sucrose; mannitol; or amino acids including, but not limited to, arginine.

The pharmaceutical composition can be stored in lyophilized form. Thus, in some embodiments, the preparation process includes a lyophilization step. The lyophilized composition may then be reformulated, typically as an aqueous composition suitable for parenteral administration, prior to administration to the dog, cat, or horse. In other embodiments, particularly where the antibody is highly stable to thermal and oxidative denaturation, the pharmaceutical composition can be stored as a liquid, i.e., as an aqueous composition, which may be administered directly, or with appropriate dilution, to the dog, cat, or horse. A lyophilized composition can be reconstituted with sterile Water for Injection (WFI). Bacteriostatic reagents, such benzyl alcohol, may be included. Thus, the invention provides pharmaceutical compositions in solid or liquid form.

The pH of the pharmaceutical compositions may be in the range of from about pH 5 to about pH 8, when administered. The compositions of the invention are sterile if they are to be used for therapeutic purposes. Sterility can be achieved by any of several means known in the art, including by filtration through sterile filtration membranes (e.g., 0.2 micron membranes). Sterility may be maintained with or without anti-bacterial agents.

Certain Uses of Antibodies and Pharmaceutical Compositions

The antibodies or pharmaceutical compositions comprising the antibodies of the invention may be useful for treating an IL-17A-induced condition. As used herein, an "IL17A-induced condition" means a disease associated with, caused by, or characterized by, elevated levels or altered gradients of IL17A concentration. Such IL17A-induced conditions include, but are not limited to, proinflammatory functions, such as plaque psoriasis, psoriatic arthritis, rheumatoid arthritis, airway inflammation, asthma, osteoarthritis, inflammatory bowel disorder, Crohn's disease, ankylosing spondylitis, atopic dermatitis, degenerative myelopathy, multiple sclerosis, and uveitis. An IL17A-induced condition may be exhibited in a human or a companion animal, including, but not limited to, canine, feline, or equine.

As used herein, "treatment" is an approach for obtaining beneficial or desired clinical results. "Treatment" as used herein, covers any administration or application of a therapeutic for disease in a mammal, including a companion animal. For purposes of this disclosure, beneficial or desired clinical results include, but are not limited to, any one or more of: alleviation of one or more symptoms, diminishment of extent of disease, preventing or delaying spread of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods provided herein contemplate any one or more of these aspects of treatment. In-line with the above, the term treatment does not require one-hundred percent removal of all aspects of the disorder.

In some embodiments, an anti-IL17A antibody, an IL17Ra ECD polypeptide, an IgG Fc variant polypeptide, or a polypeptide or pharmaceutical composition comprising such can be utilized in accordance with the methods herein to treat IL17A-induced conditions. In some embodiments, an antibody, polypeptide, or pharmaceutical composition is administered to a human or to a companion animal, such as a canine, a feline, or equine, to treat an IL17A-induced condition.

A "therapeutically effective amount" of a substance/molecule, agonist or antagonist may vary according to factors such as the type of disease to be treated, the disease state, the severity and course of the disease, the type of therapeutic purpose, any previous therapy, the clinical history, the response to prior treatment, the discretion of the attending veterinarian, age, sex, and weight of the animal, and the ability of the substance/molecule, agonist or antagonist to elicit a desired response in the animal. A therapeutically effective amount is also one in which any toxic or detrimental effects of the substance/molecule, agonist or antagonist are outweighed by the therapeutically beneficial effects. A therapeutically effective amount may be delivered in one or more administrations. A therapeutically effective amount refers to an amount effective, at dosages and for periods of time necessary, to achieve the desired therapeutic or prophylactic result.

In some embodiments, an anti-IL17A antibody, an IL17Ra ECD polypeptide, an IgG Fc variant polypeptide, or a polypeptide or pharmaceutical composition comprising such is administered parenterally, by subcutaneous administration, intravenous infusion, or intramuscular injection. In some embodiments, an anti-IL17A antibody, an IL17Ra ECD polypeptide, an IgG Fc variant polypeptide, or a polypeptide or pharmaceutical composition comprising such is administered as a bolus injection or by continuous infusion over a period of time. In some embodiments, an anti-IL17A antibody, an IL17Ra ECD polypeptide, an IgG Fc variant polypeptide, or a polypeptide or pharmaceutical composition comprising such is administered by an intramuscular, an intraperitoneal, an intracerebrospinal, a subcutaneous, an intra-arterial, an intrasynovial, an intrathecal, or an inhalation route.

Anti-IL17A antibodies, IL17Ra ECD polypeptides, IgG Fc variant polypeptides, or polypeptides or pharmaceutical compositions comprising such may be administered in an amount in the range of 0.1 mg/kg body weight to 100 mg/kg body weight per dose. In some embodiments, anti-IL17A antibodies, IL17Ra ECD polypeptides, IgG Fc variant polypeptides, or polypeptides or pharmaceutical compositions may be administered in an amount in the range of 0.5 mg/kg body weight to 50 mg/kg body weight per dose. In some embodiments, anti-IL17A antibodies, IL17Ra ECD polypeptides, IgG Fc variant polypeptides, or polypeptides or pharmaceutical compositions may be administered in an amount in the range of 1 mg/kg body weight to 10 mg/kg body weight per dose. In some embodiments, anti-IL17A antibodies, IL17Ra ECD polypeptides, IgG Fc variant polypeptides, or polypeptides or pharmaceutical compositions may be administered in an amount in the range of 0.5 mg/kg body weight to 100 mg/kg body, in the range of 1 mg/kg body weight to 100 mg/kg body weight, in the range of 5 mg/kg body weight to 100 mg/kg body weight, in the range of 10 mg/kg body weight to 100 mg/kg body weight, in the range of 20 mg/kg body weight to 100 mg/kg body weight, in the range of 50 mg/kg body weight to 100 mg/kg body weight, in the range of 1 mg/kg body weight to 10 mg/kg body weight, in the range of 5 mg/kg body weight to 10 mg/kg body weight, in the range of 0.5 mg/kg body weight to 10 mg/kg body weight, or in the range of 5 mg/kg body weight to 50 mg/kg body weight.

In some embodiments, an anti-IL17A antibody, an IL17Ra ECD polypeptide, an IgG Fc variant polypeptide, or a polypeptide or pharmaceutical composition comprising such can be administered to a companion animal at one time or over a series of treatments. For example, an anti-IL17A antibody, an IL17Ra ECD polypeptide, an IgG Fc variant polypeptide, or a polypeptide or pharmaceutical composition comprising such may be administered at least once, more than once, at least twice, at least three times, at least four times, or at least five times.

In some embodiments, the dose is administered once per week for at least two or three consecutive weeks, and in some embodiments, this cycle of treatment is repeated two or more times, optionally interspersed with one or more weeks of no treatment. In other embodiments, the therapeutically effective dose is administered once per day for two to five consecutive days, and in some embodiments, this cycle of treatment is repeated two or more times, optionally interspersed with one or more days or weeks of no treatment.

Administration "in combination with" one or more further therapeutic agents includes simultaneous (concurrent) and consecutive or sequential administration in any order. The term "concurrently" is used herein to refer to administration of two or more therapeutic agents, where at least part of the administration overlaps in time or where the administration of one therapeutic agent falls within a short period of time relative to administration of the other therapeutic agent. For example, the two or more therapeutic agents are administered with a time separation of no more than about a specified number of minutes. The term "sequentially" is used herein to refer to administration of two or more therapeutic agents where the administration of one or more agent(s) continues after discontinuing the administration of one or more other agent(s), or wherein administration of one or more agent(s) begins before the administration of one or more other agent(s). For example, administration of the two or more therapeutic agents are administered with a time separation of more than about a specified number of minutes. As used herein, "in conjunction with" refers to administration of one treatment modality in addition to another treatment modality. As such, "in conjunction with" refers to administration of one treatment modality before, during or after administration of the other treatment modality to the animal.

In some embodiments, the method comprises administering in combination with an anti-IL17A antibody, an IL17Ra ECD polypeptide, or a pharmaceutical composition comprising such, a NFκB inhibitor, a MAPKs inhibitor and a C/EBPs inhibitor. In some embodiments, the method comprises administering in combination with an anti-IL17A antibody, an IL17Ra ECD polypeptide, or a pharmaceutical composition comprising such, an anti-IL31 antibody, an anti-TNFα antibody, an anti-CD20 antibody, an anti-CD19 antibody, an anti-CD25 antibody, an anti-IL4 antibody, an anti-IL13 antibody, an anti-IL23 antibody, an anti-IgE antibody, an anti-CD11α antibody, anti-IL6R antibody, anti-α4-Intergrin antibody, an anti-IL12 antibody, an anti-IL10 antibody, or an anti-BlyS antibody.

Provided herein are methods of exposing to a cell an anti-IL17A antibody, an IL17Ra ECD polypeptide, or a pharmaceutical composition comprising such under conditions permissive for binding to IL17A. In some embodiments, the cell is exposed to the antibody, polypeptide, or pharmaceutical composition ex vivo. In some embodiments, the cell is exposed to the antibody, polypeptide, or pharmaceutical composition in vivo. In some embodiments, a cell is exposed to the anti-IL17A antibody, the IL17Ra ECD polypeptide, or the pharmaceutical composition under conditions permissive for binding to intracellular IL17A. In some embodiments, a cell is exposed to the anti-IL17A antibody, the IL17Ra ECD polypeptide, or the pharmaceutical composition under conditions permissive for binding to extracellular IL17A. In some embodiments, a cell may be exposed in vivo to the anti-IL17A antibody, the IL17Ra ECD polypeptide, or the pharmaceutical composition by any one or more of the administration methods described herein, including but not limited to, intraperitoneal, intramuscular, intravenous injection into the subject. In some embodiments, a cell may be exposed ex vivo to the anti-IL17A antibody, the IL17Ra ECD polypeptide, or the pharmaceutical composition by exposing the cell to a culture medium comprising the antibody, the polypeptide, or the pharmaceutical composition. In some embodiments, the permeability of the cell membrane may be affected by the use of any number of methods understood by those of skill in the art (such as electroporating the cells or exposing the cells to a solution containing calcium chloride) before exposing the cell to a culture medium comprising the antibody or the pharmaceutical composition.

In some embodiments, the binding results in a reduction of IL17A signaling function by the cell. In some embodiments, an anti-IL17A antibody or IL17Ra ECD polypeptide may reduce IL17A signaling function in a cell by at least 10%, at least 15%, at least 20%, at least 25%, at least 30%, at least 35%, at least 40%, at least 45%, at least 50%, at least 60%, at least 70%, at least 80%, at least 90%, or 100% compared to IL17A signaling function in the absence of the antibody or polypeptide, as measured by a reduction in IL6 secretion. In some embodiments, the reduction in IL17A signaling function or the reduction in IL6 secretion is between 10% and 15%, between 10% and 20%, between 10% and 25%, between 10% and 30%, between 10% and 35%, between 10% and 40%, between 10% and 45%, between 10% and 50%, between 10% and 60%, between 10% and 70%, between 10% and 80%, between 10% and 90%, between 10% and 100%, between 15% and 20%, between 15% and 25%, between 15% and 30%, between 15% and 35%, between 15% and 40%, between 15% and 45%, between 15% and 50%, between 15% and 60%, between 15% and 70%, between 15% and 80%, between 15% and 90%, between 15% and 100%, between 20% and 25%, between 20% and 30%, between 20% and 35%, between 20% and 40%, between 20% and 45%, between 20% and 50%, between 20% and 60%, between 20% and 70%, between 20% and 80%, between 20% and 90%, between 20% and 100%, between 25% and 30%, between 25% and 35%, between 25% and 40%, between 25% and 45%, between 25% and 50%, between 25% and 60%, between 25% and 70%, between 25% and 80%, between 25% and 90%, between 25% and 100%, between 30% and 35%, between 30% and 40%, between 30% and 45%, between 30% and 50%, between 30% and 60%, between 30% and 70%, between 30% and 80%, between 30% and 90%, between 30% and 100%, between 35% and 40%, between 35% and 45%, between 35% and 50%, between 35% and 60%, between 35% and 70%, between 35% and 80%, between 35% and 90%, between 35% and 100%, between 40% and 45%, between 40% and 50%, between 40% and 60%, between 40% and 70%, between 40% and 80%, between 40% and 90%, between 40% and 100%, between 45% and 50%, between 45% and 60%, between 45% and 70%, between 45% and 80%, between 45% and 90%, between 45% and 100%, between 50% and 60%, between 50% and 70%, between 50% and 80%, between 50% and 90%, between 50% and 100%, between 60% and 70%, between 60% and 80%, between 60% and 90%, between 60% and 100%, between 70% and 80%, between 70% and 90%, between 70% and 100%, between 80% and 90%, between 80% and 100%, or between 90% and 100%.

Provided herein are methods of using the anti-IL17A antibodies, polypeptides and polynucleotides for detection, diagnosis and monitoring of an IL17A-induced condition. Provided herein are methods of determining whether a companion animal will respond to anti-IL17A antibody therapy. In some embodiments, the method comprises detecting whether the animal has cells that express IL17A using an anti-IL17A antibody. In some embodiments, the method of detection comprises contacting the sample with an antibody, polypeptide, or polynucleotide and determining whether the level of binding differs from that of a reference or comparison sample (such as a control). In some embodiments, the method may be useful to determine whether the antibodies or polypeptides described herein are an appropriate treatment for the subject animal.

In some embodiments, the sample is a biological sample. The term "biological sample" means a quantity of a substance from a living thing or formerly living thing. In some embodiments, the biological sample is a cell or cell/tissue lysate. In some embodiments, the biological sample includes, but is not limited to, blood, (for example, whole blood), plasma, serum, urine, synovial fluid, and epithelial cells.

In some embodiments, the cells or cell/tissue lysate are contacted with an anti-IL17A antibody or IL17Ra ECD polypeptide and the binding between the antibody or the polypeptide and the cell is determined. When the test cells show binding activity as compared to a reference cell of the same tissue type, it may indicate that the subject would benefit from treatment with an anti-IL17A antibody or an IL17Ra ECD polypeptide. In some embodiments, the test cells are from tissue of a companion animal.

Various methods known in the art for detecting specific antibody-antigen binding can be used. Exemplary immunoassays which can be conducted include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be attached to the subject antibodies and is selected so as to meet the needs of various uses of the method which are often dictated by the availability of assay equipment and compatible immunoassay procedures. Appropriate labels include, without limitation, radionuclides (for example $^{125}$I, $^{131}$I, $^{35}$S, $^{3}$H, or $^{32}$P), enzymes (for example, alkaline phosphatase, horseradish peroxidase, luciferase, or β-galactosidase), fluorescent moieties or proteins (for example, fluorescein, rhodamine, phycoerythrin, GFP, or BFP), or luminescent moieties (for example, Qdot™ nanoparticles supplied by the Quantum Dot Corporation, Palo Alto, Calif.). General techniques to be used in performing the various immunoassays noted above are known to those of ordinary skill in the art.

For purposes of diagnosis, the polypeptide including antibodies can be labeled with a detectable moiety including but not limited to radioisotopes, fluorescent labels, and various enzyme-substrate labels know in the art. Methods of conjugating labels to an antibody are known in the art. In some embodiments, the anti-IL17A antibodies need not be labeled, and the presence thereof can be detected using a second labeled antibody which binds to the first anti-IL17A antibody. In some embodiments, the anti-IL17A antibody can be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987). The anti-IL17A antibodies and polypeptides can also be used for in vivo diagnostic assays, such as in vivo imaging. Generally, the antibody or the polypeptide is labeled with a radionuclide (such as $^{111}$In, $^{99}$Tc, $^{14}$C, $^{131}$I, $^{125}$, $^{3}$H, or any other radionuclide label, including those outlined herein) so that the cells or tissue of interest can be localized using immunoscintiography. The antibody may also be used as staining reagent in pathology using techniques well known in the art.

In some embodiments, a first antibody is used for a diagnostic and a second antibody is used as a therapeutic. In some embodiments, the first and second antibodies are different. In some embodiments, the first and second antibodies can both bind to the antigen at the same time, by binding to separate epitopes.

The following examples illustrate particular aspects of the disclosure and are not intended in any way to limit the disclosure.

EXAMPLES

Example 1

Identification of Mouse Monoclonal Antibodies that Bind to Canine IL17A

The nucleotide sequences encoding canine IL17A precursor protein with its native signal sequence (SEQ ID NO: 28) and either (1) a poly-His tag (canine IL17A-polyHis) or (2) human Fc (canine IL17A-huFc) on the C-terminal were synthesized and cloned into separate mammalian expression vectors. The resulting vectors were separately transfected into 293 cells.

The supernatant containing canine IL17A protein was collected and filtered. Canine IL17A-polyHis was affinity purified using Ni-NTA column (Catalog No. 17-5318-01, GE Healthcare Life Sciences) and canine IL17A-huFc was affinity purified using a protein A column (CAPTIVA Protein A Affinity Resin, Repligen).

A hybridoma bank generated from immunization of mice with human IL17A was screened for affinity to canine IL17A-polyHis (Catalog No. 70102-DNAE-50, Sino Biological) by enzyme linked immunosorbent assay (ELISA). Five hybridoma clones were identified for further characterization. Antibodies from clones A, B, C, D, and E were purified and their isotype determined using a Rapid Mouse Antibody Isotyping Kit (Catalog No. 26178, ThermoFisher Scientific). Clones A, C, D, and E were identified as mouse heavy chain isotype IgG1 and clone B was identified as mouse heavy chain isotype IgG2b. Each of the five clones were identified as having mouse kappa light chain.

Example 2

Binding Affinity of Monoclonal Antibodies to Canine IL17A by ELISA

Binding affinity of monoclonal antibodies A, B, C, D, and E to canine IL17A-huFc polypeptide was analyzed by ELISA. In the binding ELISA performed, the wells were coated with anti-human Fc antibody. Canine IL17A-huFc protein was then added to the wells. Antibody purified from each of the five hybridoma clones was added to the wells at various concentrations (19.35 nM, 6.45 nM, 2.15 nM, 0.75 nM, 0.24 nM, 0.08 nM, 0.03 nM, and 0 nM). Goat anti-mouse Fc-HRP was added and color was developed. FIG. 1 shows the results of the binding ELISA. Table 3 below provides the EC50 values associated with the binding ELISA for each of the clones.

TABLE 3

| Canine IL17A ELISA | |
| --- | --- |
| Antibody | EC50 (ng/mL) |
| A | 0.24 |
| B | 180 |
| C | 0.20 |
| D | 0.28 |
| E | 0.21 |

Example 3

Affinity of Monoclonal Antibodies to Canine IL17A by Biosensor-Based Assay

Equilibrium dissociation constants ($K_d$) of the top four hybridoma candidates (clones A, C, D, and E) at a single concentration of 10 µg/mL were determined to each be less than 10 nM using biolayer interferometry. Briefly, antibody concentrations were measured by protein A assay using Biosensor OCTET (Forte Bio). Canine IL17A-huFc was captured to anti-human Fc bound biosensors. The association of anti-IL17A antibody from clones A, C, D, and E to the canine IL17A-huFc was monitored for 90 seconds. Dissociation was monitored for 600 seconds. A buffer only blank curve was subtracted to correct for any drift. The data were fit to a 1:1 binding model using FORTEBIO data analysis software to determine the $k_{on}$, $k_{off}$ and the $K_d$. The buffer for dilutions and all binding steps was: 20 mM phosphate, 150 mM NaCl, pH 7.2.

Example 4

IL17Ra Domains for Binding IL17Ra

Extracellular domains of canine IL17Ra responsible for binding to canine IL17A were identified, for example, SEQ ID NO: 33 and SEQ ID NO: 94. The nucleotide sequence encoding an extracellular domain of canine IL17Ra (canine IL17Ra ECD, SEQ ID NO: 33) with human Fc and a poly-His tag on the C-terminal (canine IL17Ra ECD-huFc-polyHis, SEQ ID NO: 42) was synthesized and cloned into a mammalian expression vector. The resulting vector was transfected into 293 cells and CHOS cells. Canine IL17Ra ECD-huFc-polyHis was affinity purified using Protein A (CAPTIVA Protein A Affinity Resin, Repligen).

The binding affinity of canine IL17A-polyHis to canine IL17Ra ECD-huFc-polyHis was assessed using biolayer interferometry. Briefly, canine IL17A-polyHis was biotinylated and captured to streptavidin biosensors. The association of canine IL17Ra ECD-huFc-polyHis was monitored for 90 seconds. Dissociation was monitored for 600 seconds. A buffer only blank curve was subtracted to correct for any drift. The data were fit to a 1:1 binding model using FORTEBIO data analysis software to determine the $k_{on}$, $k_{off}$ and the $K_d$. The buffer for dilutions and all binding steps was: 20 mM phosphate, 150 mM NaCl, pH 7.2. Based on several runs of this assay, the $K_d$ of canine IL17A-polyHis and canine IL17Ra ECD-huFc-polyHis was determined to be about $1.5 \times 10^{-9}$ to about $4.2 \times 10^{-9}$ M. These data suggest that the canine IL17Ra ECD fragment tested may have an affinity to IL17A sufficient for use as an IL17A antagonist, for example in the treatment of IL17A-induced conditions.

Extracellular domains of human IL17Ra, feline IL17Ra, and equine IL17Ra responsible for binding to IL17A were identified, for example, SEQ ID NO: 97, SEQ ID NO: 98, and SEQ ID NO: 99, respectively. The nucleotide sequence encoding an extracellular domain of human IL17Ra (human IL17Ra ECD, SEQ ID NO: 97) with human IgG4-Fc on the C-terminal (human IL17Ra ECD-IgG4-Fc, SEQ ID NO: 40) may be prepared, cloned into a mammalian expression vector, and expressed in cells for isolation of the fusion protein. In addition, the nucleotide sequence encoding an extracellular domain of feline IL17Ra (feline IL17Ra ECD, SEQ ID NO: 98) with feline IgG-2 Fc on the C-terminal (feline IL17Ra ECD-feline IgG-2, SEQ ID NO: 41) may be prepared, cloned into a mammalian expression vector, and expressed in cells for the isolation of the fusion protein. Further, the nucleotide sequence encoding an extracellular domain of equine IL17Ra (equine IL17Ra ECD, SEQ ID NO: 99) with equine IgG-2 Fc on the C-terminal (equine IL17Ra ECD-equine IgG-2-Fc, SEQ ID NO: 42) may be prepared, cloned into a mammalian expression vector, and expressed in cells for the isolation of the fusion protein. The human, canine, feline, and equine IL17Ra ECD polypeptides and IL17Ra ECD/Fc fusion polypeptides described herein may be used in the treatment of IL17A-induced conditions, for example in humans, dogs, cats, or horses.

Example 5

Anti-IL17A Monoclonal Antibodies Reduce IL17A Binding to IL17Ra ECD

Each of the top four clones (A, C, D, and E) were determined to reduce the ability of canine IL17A to bind to canine IL17Ra ECD-huFc-polyHis in a biosensor-based assay. A complex between biotinylated canine IL17A- polyHis bound to streptavidin biosensors and anti-IL17A antibody (20 g/mL) from one of each of clones A, B, C, D, and E was formed first. Then, the ability of canine IL17Ra ECD-huFc-PolyHis to bind to the IL17A/IL17A antibody complex was measured. The signal was compared to binding of IL17A to canine IL17Ra ECD-huFc-PolyHis in the absence of IL17A antibody. The biosensor signals observed from the IL17A/anti-IL17A antibody complex binding to the IL17Ra ECD were diminished with antibodies A, C, D, and E compared to the control (no antibody). These results suggest that Clone A, C, D, and E antibodies can reduce the ability of canine IL17A to bind to canine IL17Ra ECD.

Example 6

Anti-IL17A Monoclonal Antibodies Reduce IL17A Signaling Function

Whether clone A-E antibodies reduced IL17A signaling function was assessed using a H1080 cell-based functional assay. H1080 cells are a human fibrosarcoma cell line (ATCC-CCL121) that secretes pro-inflammatory cytokines IL6 and IL8 upon stimulation by either human or canine IL17A. Anti-IL17A antibodies may reduce the levels of secreted IL6 by blocking or reducing the ability of IL17A to bind IL17Ra on the surface of H1080 cells.

In this assay, the H1080 cells were incubated overnight with serial dilutions (10 nM, 3.3 nM, 1.1 nM, 0.33 nM, 0.11 nM, 0.03 nM, 0.01 nM, 0 nM) of purified anti-IL17A antibodies from clones A-E mixed with 1 nM canine IL17A. The amount of IL6 secreted from the cells into the medium was measured by a Human IL6 DUOSET ELISA kit (Catalog No. DY206-05, R&D Systems). A reduced level of IL6 secreted from H1080 cells was observed after treatment with each of the five anti-IL17A antibody clones compared to untreated cells. These results suggest that each of antibody clones A-E can reduce binding of IL17A to IL17Ra on the surface of H1080 cells and inhibit IL6 production. The antibody concentration at which a half-maximal response was observed (EC50) is summarized in Table 4, below. Clone A, C, D, and E antibodies appear to be more potent than clone B antibodies in this cell-based functional assay.

TABLE 4

| H1080 Cell Functional Assay | |
| --- | --- |
| Antibody | EC50 (ng/mL) |
| A | 13 |
| B | 800 |
| C | 7 |
| D | 47 |
| E | 40 |

Example 7

Epitope Binding Immunoassay

The IL17A epitope binding profiles of antibodies produced by clones A, B, C, D, and E were analyzed by competitive immunoassay. In this experiment, biotinylated canine IL17A-polyHis was immobilized on streptavidin sensor tips. The IL17A-bound sensor tips were exposed to Antibody 1. After a short wash, the sensor tips were then exposed to Antibody 2. If Antibody 2 failed to bind to the IL17A/Antibody 1 complex, the binding signal would not increase between exposure to Antibody 1 and exposure to Antibody 2. This would suggest that the two antibodies bound to the same or a closely related epitope and should be binned into the same epitope group. If Antibody 2 bound to the IL17A/Antibody 1 complex, then the binding signal would increase between exposure to Antibody 1 and exposure to Antibody 2. This scenario would suggest that the two antibodies belong to different epitope groups. In addition to controls, the following combinations of antibodies were used in the IL17A binding experiments: 1) Clone A followed by Clone A, B, C, D, and E; 2) Clone B followed by Clone A, B, C, D, and E; 3) Clone C followed by Clone A, B, C, D, and E; and 4) Clone D followed by Clone A, B, C, D, and E; and 5) Clone E followed by Clone A, B, C, D, and E.

Two different epitope binding groups were identified. Clones A, C, and E were identified as belonging to one group and Clone D was identified as belonging to a second group. Due to the weak affinity of clone B to IL17A, the epitope binding group for clone B was inconclusive.

Example 8

Identification of Anti-IL17A Monoclonal Antibody Sequences

Hybridoma clones A, C, D, and E were pelleted and total RNA samples were extracted. Oligonucleotide primers for amplifying mouse immunoglobulin (Ig) variable domains were used to obtain cDNA using standard techniques. Variable regions of both heavy chains and light chains of the clones were amplified using in-house designed reverse primers. Amplified variable cDNAs were cloned into pRACE vector and plasmid DNA samples were prepared. The variable light chain (VL) and variable heavy chain (VH) of each of the four clones were sequenced and analyzed by sequence alignment (FIGS. 2A and B, respectively).

Clone A has a variable heavy chain sequence of SEQ ID NO: 35 and a variable light chain sequence of SEQ ID NO: 34; Clone C has a variable heavy chain sequence of SEQ ID NO: 25 and a variable light chain sequence of SEQ ID NO: 24; Clone D has a variable heavy chain sequence of SEQ ID NO: 37 and a variable light chain sequence of SEQ ID NO: 36; and Clone E has a variable heavy chain sequence of SEQ ID NO: 39 and a variable light chain sequence of SEQ ID NO: 38.

The CDRs of Clones A-E antibodies were determined using a combination of the Chothia, the Kabat, the AbM, and the contact numbering schemes or definitions.

Clone C has a CDR-H1 sequence of SEQ ID NO: 1, a CDR-H2 sequence of SEQ ID NO: 2, a CDR-H3 sequence of SEQ ID NO: 3, a CDR-L1 sequence of SEQ ID NO: 8, a CDR-L2 sequence of SEQ ID NO: 9, and a CDR-L3 sequence of SEQ ID NO: 10.

Clone A has a CDR-H1 sequence of SEQ ID NO: 52, a CDR-H2 sequence of SEQ ID NO: 53 or SEQ ID NO: 109, a CDR-H3 sequence of SEQ ID SEQ ID NO: 54, a CDR-L1 sequence of SEQ ID NO: 59 or SEQ ID NO: 111, a CDR-L2 sequence of SEQ ID NO: 60 or SEQ ID NO: 112, and a CDR-L3 sequence of SEQ ID NO: 61.

Clone E has a CDR-H1 sequence of SEQ ID NO: 66, a CDR-H2 sequence of SEQ ID NO: 67 or SEQ ID NO: 114, a CDR-H3 sequence of SEQ ID NO: 68, a CDR-L1 sequence of SEQ ID NO: 73 or SEQ ID NO: 116, a CDR-L2 sequence of SEQ ID NO: 74 or SEQ ID NO: 117; and a CDR-L3 sequence of SEQ ID NO: 75.

Clone D has a CDR-H1 sequence of SEQ ID NO: 80, a CDR-H2 sequence of SEQ ID NO: 81 or SEQ ID NO: 119, a CDR-H3 sequence of SEQ ID NO: 82, a CDR-L1 sequence of SEQ ID NO: 87 or SEQ ID NO: 121, a CDR-L2 sequence of SEQ ID NO: 88 or SEQ ID NO: 122, and a CDR-L3 sequence of SEQ ID NO: 89.

Example 9

Expression and Purification of Murine-Canine Chimeric and Caninized IL17 Clone C Antibodies from CHO Cells Nucleotide sequences encoding a chimeric antibody were designed for a fusion of murine Clone C VH (SEQ ID NO: 25) and VL (SEQ ID NO: 24) to canine constant heavy chain and canine constant light chain. The nucleotide sequences were chemically synthesized and inserted into an expression vector suitable for transfection into a CHO host cell. After transfection into CHO cells, the light chain or heavy chain protein or both were secreted from the cell and purified by column chromatography. For example, chimeric Clone C having canine IgG-B (SEQ ID NO: 27) and canine kappa constant chain (SEQ ID NO: 26) was purified by single step Protein A column chromatography.

Murine Clone C VH and VL were caninized by searching and selecting proper canine germline antibody sequences as a template for CDR grafting, followed by protein modeling (SEQ ID NO: 15 and SEQ ID NO: 16). Caninized Clone C comprising caninized Clone C VH and canine IgG-B (SEQ ID NO: 18) and caninized Clone C VL and canine kappa constant region (SEQ ID NO: 21) was expressed and purified in a single step with a protein A column (Catalog No: 17127901, GE Healthcare Life Sciences). The antibody expression vectors were then used to perform pilot-scale transfection in CHO-S cells using the FreestyleMax™ transfection reagent (Life Technologies). The supernatant was harvested by clarifying the conditioned media. Protein was purified with a single pass Protein A chromatography step and used for further investigation.

Other chromatographic methods that may be used for purification include, ion exchange column chromatography, hydrophobic interaction column chromatography, mixed mode column chromatography such as CHT, or multimodal mode column chromatography such as CAPTOMMC (Catalog No. 17371605, GE Healthcare Life Sciences). Low pH or other viral inactivation and viral removal steps may also be applied. The purified protein may be admixed with excipients, and sterilized by filtration to prepare a pharmaceutical composition. The pharmaceutical composition comprising the IL17A antibodies described herein may be administered to a dog with an IL17-induced condition, such as atopic dermatitis in an amount sufficient to bind IL17A.

Example 10

Demonstration of IL17A Binding Activity

Figure 3A:
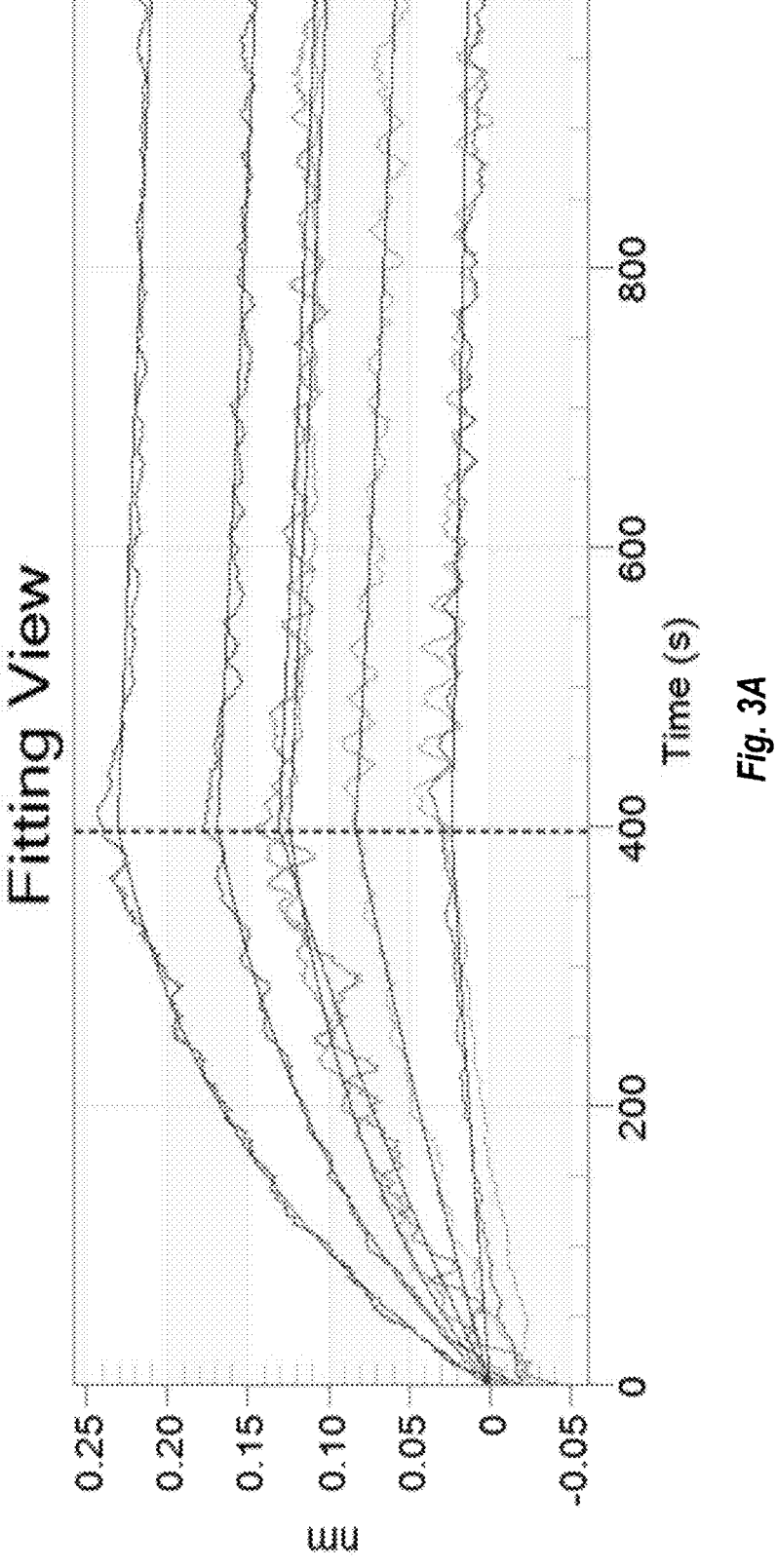
FIGS. 3A-3B show a canine IL17A binding analysis using various concentrations of Clone C antibody (A) and caninized Clone C antibody (B).

Hybridoma Clone C having VL SEQ ID NO: 24 and VH SEQ ID NO: 25 exhibited affinity to canine IL17A with kinetics potentially sufficient for therapeutic activity. The affinity to canine IL17A was preserved in caninized Clone C (FIG. 3) and chimeric Clone C (data not shown). The caninized Clone C and chimeric Clone C antibodies were prepared as described in Example 9.

The binding analysis was performed using a Biosensor OCTET as follows. Briefly, canine IL17A-polyHis, which was expressed and purified from CHO-S cells, was biotinylated using EZ-LINK NHS-LC-biotin (Catalog No.

21336, Thermo Scientific). Free, unreacted biotin was removed from biotinylated IL17A by dialysis. Biotinylated canine IL17A was captured on streptavidin sensor tips (Catalog No. 18-509, ForteBio). The association of different concentrations (0 nM, 18.33 nM, 45.87 nM, 110 nM, 220 nM) of hybridoma Clone C or caninized Clone C antibody to canine IL17A was monitored for 90 seconds. Dissociation was monitored for 600 seconds. A buffer only blank curve was subtracted to correct for any drift. The data were fit to a 1:1 binding model using FORTEBIO data analysis software to determine the $k_{on}$, $k_{off}$ and the $K_d$. The buffer for dilutions and all binding steps was: 20 mM phosphate, 150 mM NaCl, pH 7.2.

Figure 3B:
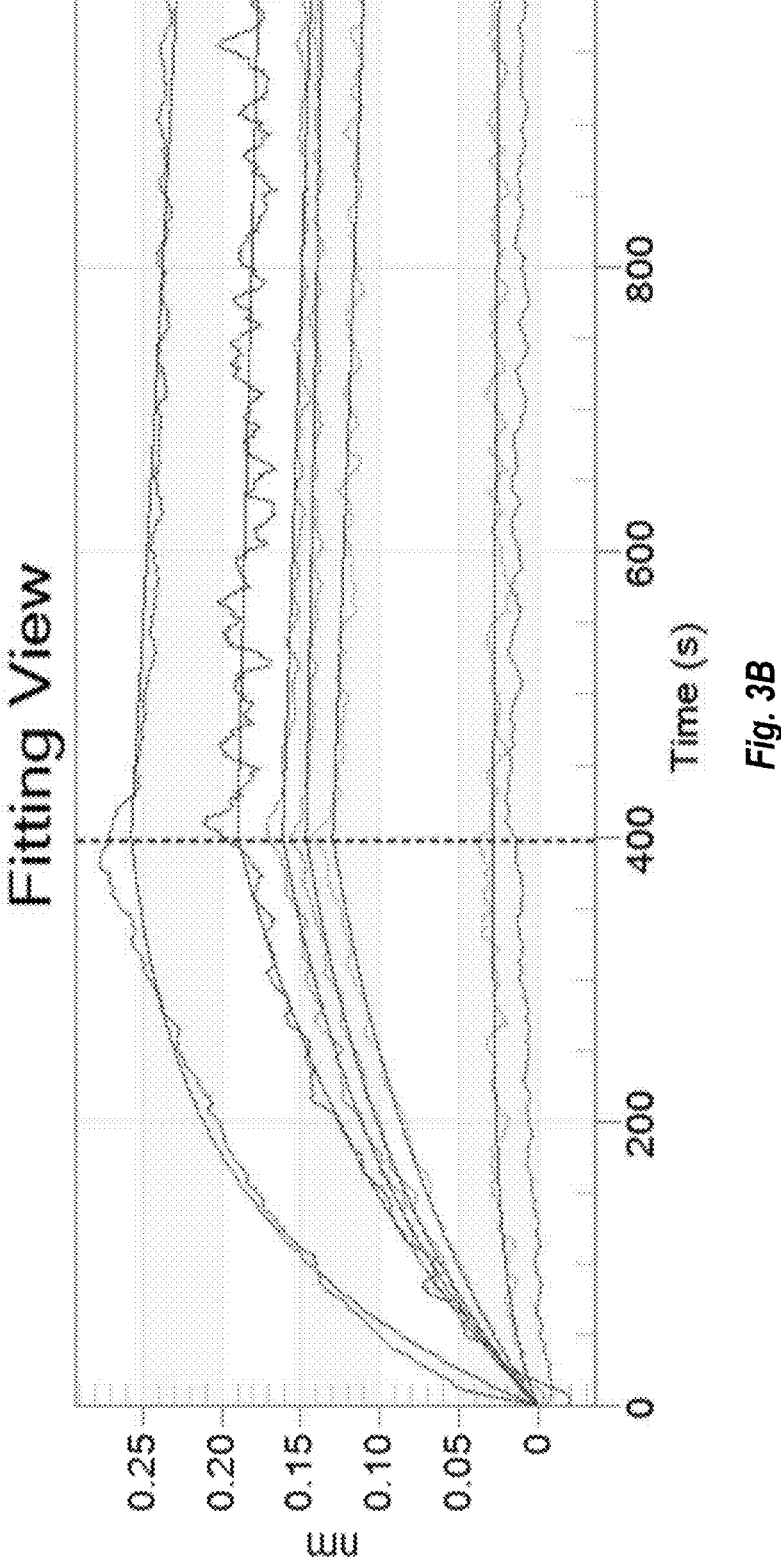

The $K_d$ of hybridoma Clone C and canine IL17A-polyHis was $7.9 \times 10^{-9}$ M (FIG. 3A) and the $K_d$ of caninized Clone C and canine IL17A-polyHis was $1.4 \times 10^{-9}$ M (FIG. 3B).

Example 11

Demonstration of IL17F Binding Activity

In addition to IL17A, there are other members of the IL17 family, including IL17F. The binding affinity of IL17F homodimer to caninized Clone C (prepared as described in Example 9) was assessed using biolayer interferometry. It was determined that caninized Clone C also binds to canine IL17F-polyHis with a $K_d$ of $4.1 \times 10^{-9}$ M.

The nucleotide sequence encoding IL17F precursor polypeptide (SEQ ID NO: 31) with a poly-His tag (canine IL17F-polyHis) on the C-terminal was synthesized and cloned into a mammalian expression vector. The resulting vector was transfected into 293 cells. The supernatant was collected and filtered, and canine IL17F-polyHis protein was affinity purified using a Ni-NTA column (CAPTIVA Protein A Affinity Resin, Repligen).

The binding analysis was performed using a biosensor OCTET as follows. Briefly, canine IL17F-polyHis was biotinylated using EZ-LINK NHS-LC-biotin (Catalog No. 21336, Thermo Scientific). Free, unreacted biotin was removed from biotinylated IL17F-polyHis by dialysis. Biotinylated canine IL17F was captured on streptavidin sensor tips (Catalog No. 18-509, ForteBio). The association of different concentrations (0 nM, 2 nM, 10.1 nM, 21.3 nM, 43.3 nM, 86.7 nM, 124 nM) of the caninized Clone C antibody and canine IL17F-polyHis was monitored for ninety seconds. Dissociation was monitored for 600 seconds. A buffer only blank curve was subtracted to correct for any drift. The data were fit to a 1:1 binding model using FORTEBIO data analysis software to determine the $k_{on}$, $k_{off}$, and the $K_d$. The buffer for dilutions and all binding steps was: 20 mM phosphate, 150 mM NaCl, pH 7.2.

Example 12

Demonstration that Caninized Clone C Inhibits IL17 Signaling

Figure 4:
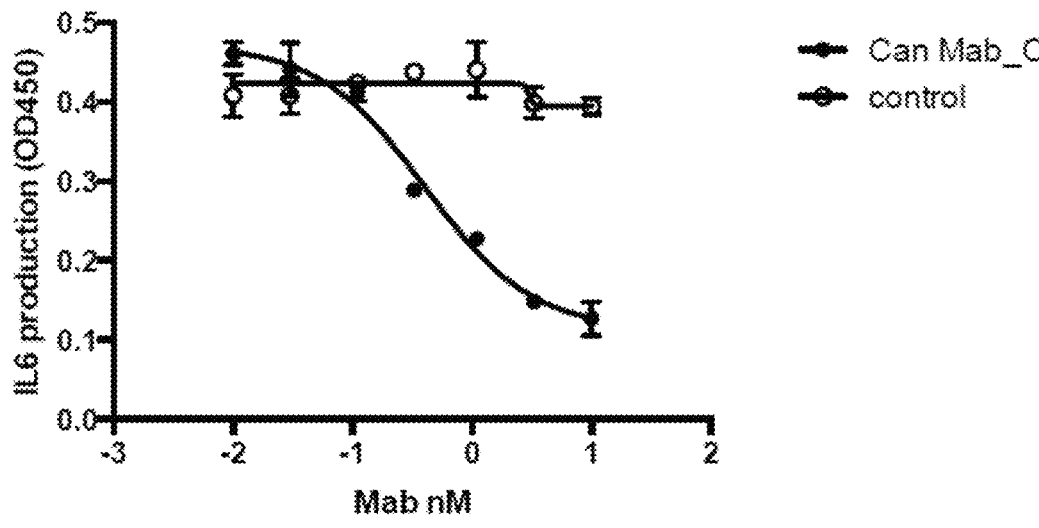
FIG. 4 shows an H1080 cell-based canine IL17A neutralization assay of caninized Clone C antibody.

The ability of caninized Clone C antibody (prepared as described in Example 9) to affect human IL17A signaling function was assessed using the H1080 cell-based functional assay described in Example 6. H1080 cells were incubated overnight with serial dilutions of purified caninized Clone C antibody mixed with 1 nM canine IL17A. The amount of IL6 secreted from the cells into the medium was measured by a Human IL6 DUOSET ELISA kit (Catalog No. DY206-05, R&D Systems). The levels of IL6 produced by H1080 cells treated with caninized Clone C antibody or an unrelated caninized IgG-B antibody as a negative control are shown in FIG. 4. In this assay, the IC50 of the caninized Clone C antibody was $0.41\times10^{-9}$ M, suggesting that caninized Clone C antibody inhibits the IL17A signaling pathway.

Example 13

Clones a, C, D, and E Cross React to Feline and Equine IL17A

The nucleotide sequences encoding feline IL17A precursor protein with its native signal sequence (SEQ ID NO: 30) and a poly-His tag on the C-terminal (feline IL17A-polyHis) and equine IL17A precursor protein with its native signal sequence (SEQ ID NO: 29) and a poly-His tag on the C-terminal (equine IL17A-polyHis) were synthesized and cloned into separate mammalian expression vectors. The resulting vectors were separately transfected into 293 cells. The supernatant containing feline IL17A-polyHis or equine IL17A-polyHis was collected and filtered, and the IL17A proteins affinity purified using a Ni-NTA column.

The binding analysis was performed using a Biosensor OCTET as follows. Both feline IL17A-polyHis and equine IL17A-polyHis were biotinylated and immobilized to streptavidin biosensors. The association of monoclonal antibody Clones A, C, D, and E (20 g/mL) to either feline or canine IL17A-polyHis was monitored for 90 seconds. Dissociation was monitored for 600 seconds. A buffer only blank curve was subtracted to correct for any drift. The data were fit to a 1:1 binding model using FORTEBIO data analysis software to determine the $k_{on}$, $k_{off}$, and the $K_d$. The buffer for dilutions and all binding steps was: 20 mM phosphate, 150 mM NaCl, pH 7.2. The biolayer interferometry analysis indicated that monoclonal antibody Clones A, C, D, and E have binding affinity to feline and equine IL17A. The $K_d$ of feline IL17A to monoclonal antibody Clone D and Clone E was $2.4\times10^{-9}$ M and $5.7\times10^{-9}$ M, respectively. Weak binding signals of Clone A to feline IL17A and Clone C to feline IL17A were observed. The $K_d$ of equine IL17A to Clone A was $5.3\times10^{-9}$ M, to Clone C was $1.3\times10^{-10}$ M, to Clone D was $2.1\times10^{-10}$ M, and to Clone E was $1.8\times10^{-10}$ M.

Example 14

Figure 5:
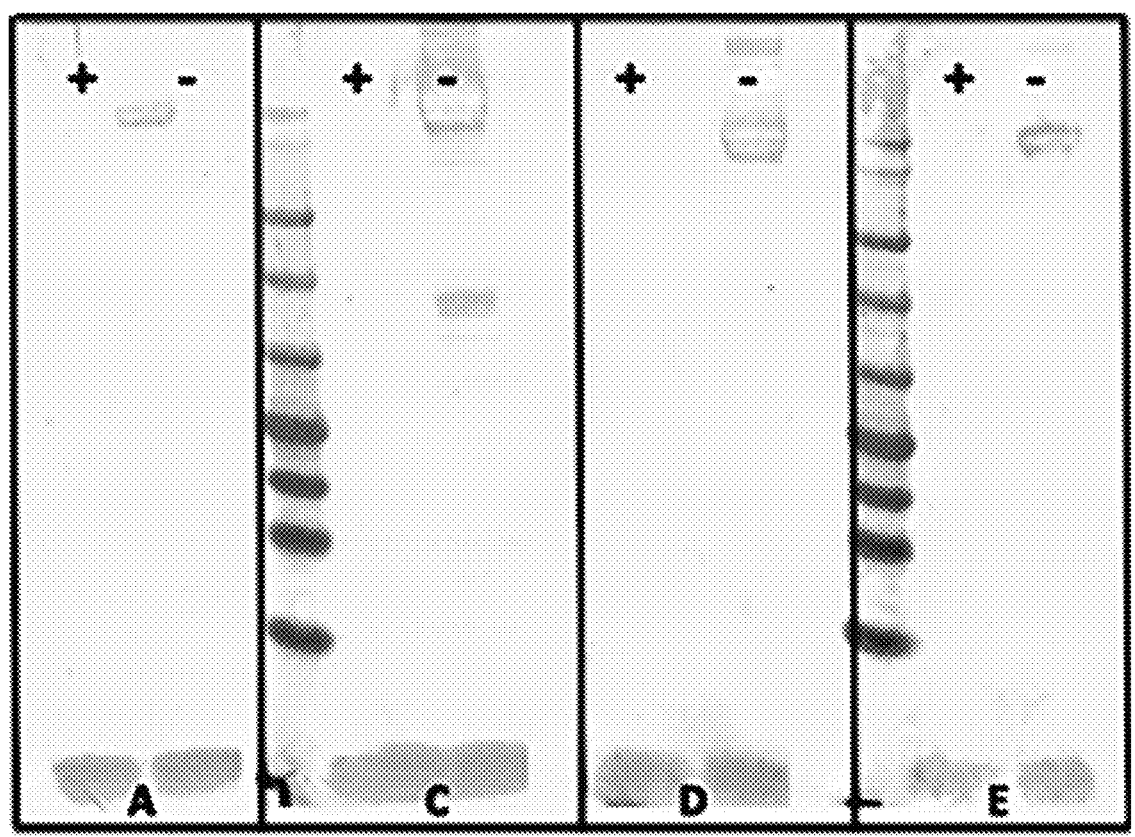
FIG. 5 shows Western blots of canine IL17A-hFc after separation by SDS-PAGE in the presence of DTT (+) or absence of DTT (−), transfer to PVDF membrane, and being probed with Clone A, C, D, or E antibody followed by goat anti-mouse IgG-HRP. Immunoreactive positive signals were only observed under non-reducing conditions.

Affinity of IL17A Monoclonal Antibodies to IL17A Proteins by Western Analysis Canine IL17A-hFc was separated by SDS-PAGE in the presence of Dithiothreitol (DTT) (reducing conditions) or the absence of DTT (non-reducing conditions). The protein was transferred to PVDF membrane and probed using Clone A, C, D, or E antibody followed by goat anti-mouse IgG-HRP. Immunoreactive positive signals were only observed in non-reducing samples, suggesting that the epitope for each of Clone A, C, D, and E antibodies may be discontinuous or conformational (FIG. 5).

Figures 6A, 6B, 6C, 6D:
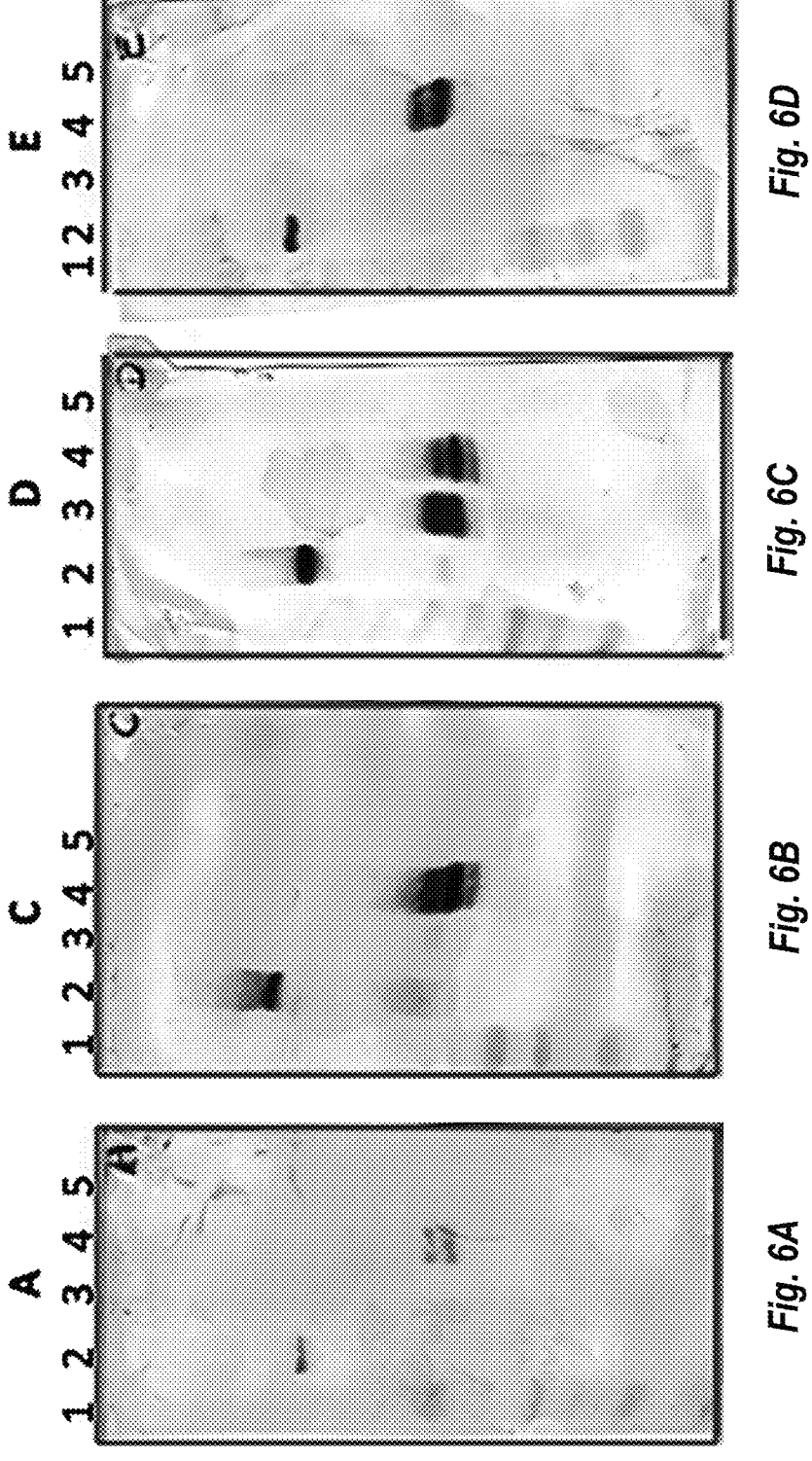
FIGS. 6A-6D show Western blots of IL17A proteins (0.6 g) probed with Clone A, Clone C, Clone D, or Clone E antibodies followed by goat anti-mouse IgG-HRP. Lane 1: Protein MW marker; Lane 2: canine IL17A-hFc; Lane 3: Feline IL17A-polyHis; Lane 4: Equine IL17A-polyHis; Lane 5: Canine IL17F.

Canine IL17A-hFc, feline IL17A-polyHis, equine IL17A-polyHis, and canine IL17F-polyHis (0.6 g) were each separated by SDS-PAGE and the proteins transferred to PVDF membranes. The blots were probed using Clone A, C, D, or E antibody followed by goat anti-mouse IgG-HRP. The Western blots are shown in FIG. 6 and the presence or absence of an immunoreactivity signal is summarized in Table 5, below. In this Western analysis, Clone A, C, and E antibodies immunoreacted to canine and equine IL17A, but not to feline IL17A or canine IL17F. Clone D antibody immunoreacted to canine, feline, and equine IL17A, but not to canine IL17F.

TABLE 5

| Immunoreactivity to IL17A protein target by Western analysis | | | | |
|---|---|---|---|---|
| | Protein Target | | | |
| Monoclonal Antibody | Canine IL17A | Feline IL17A | Equine IL17A | Canine IL17F |
| Clone A | Yes | No | Yes | No |
| Clone C | Yes | No | Yes | No |
| Clone D | Yes | Yes | Yes | No |
| Clone E | Yes | No | Yes | No |

Example 15

Identification of IL17A Binding Epitope for Clone C Antibody

To identify the canine IL17A epitope that is recognized by Clone C antibody, the antibody's affinity to a series of mutant canine IL17A-hFc-polyHis proteins was considered by Western analysis. The results described in Example 13 showed that Clone C antibody immunoreacted to canine and equine IL17A, but not to feline IL17A. To identify potential IL17A epitope binding sites for Clone C, the amino acid sequences and 3-D protein structure models of canine, equine, and feline IL17A proteins were compared. Three segments of amino acid sequence that are generally conserved between canine and equine IL17A proteins and that are generally divergent when compared to the feline IL17A sequence were identified as potential epitope binding regions for Clone C antibody.

Three mutant canine IL17A-hFc-polyHis polypeptides were constructed with each having amino acid substitution(s) in one of the three segments identified by sequence and 3-D structure comparison (Mutants 1, 2, 3). The amino acid substitutions of Mutants 1-3 were derived from the amino acids divergent between the canine and feline IL17A sequences. (See Table 6, below). A fourth mutant canine IL17A-hFc-polyHis polypeptide (Mutant 4) was constructed that harbored all the amino acid substitutions of Mutants 1, 2, and 3. A fifth mutant canine IL17A-hFc-polyHis polypeptide was constructed having a C-terminal deletion of amino acids 126-131 of SEQ ID NO: 22.

TABLE 6

| Canine IL17A-hFc mutant | Amino acid modification(s) (based on SEQ ID NO: 22) | +DDT lane | −DDT lane |
|---|---|---|---|
| Mutant 1 | R71L, L73W, I82T | 3 | 4 |
| Mutant 2 | R32A, T34K, N35S, N44R | 5 | 6 |
| Mutant 3 | Q103R | 7 | 8 |
| Mutant 4 | R32A, T34K, N35S, N44R, R71L, L73W, I82T, Q103R | 9 | 10 |
| Mutant 5 | C-terminal deletion of amino acids 126-131 | 1 | 2 |

Figure 7A:
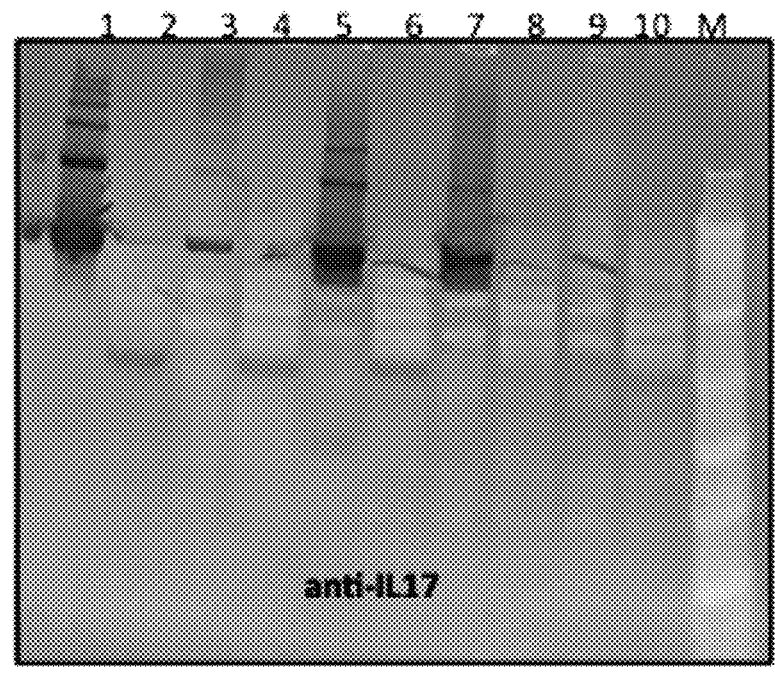
FIGS. 7A-7B show Western blots of canine IL17A-hFc-polyHis mutant proteins after separation by SDS-PAGE in the presence (+) or absence (−) of DDT, transfer to PVDF membrane, and being probed with either Clone C antibody (A) or anti-human IgG Fc antibody (B). Lane 1: Mutant 5 (+DTT); Lane 2: Mutant 5 (−DTT); Lane 3: Mutant 1 (+DTT); Lane 4: Mutant 1 (−DTT); Lane 5: Mutant 2 (+DTT); Lane 6: Mutant 2 (−DTT); Lane 7: Mutant 3 (+DTT); Lane 8: Mutant 3 (−DTT); Lane 9: Mutant 4 (+DTT); Lane 10: Mutant 4 (−DTT).
Figure 7B:
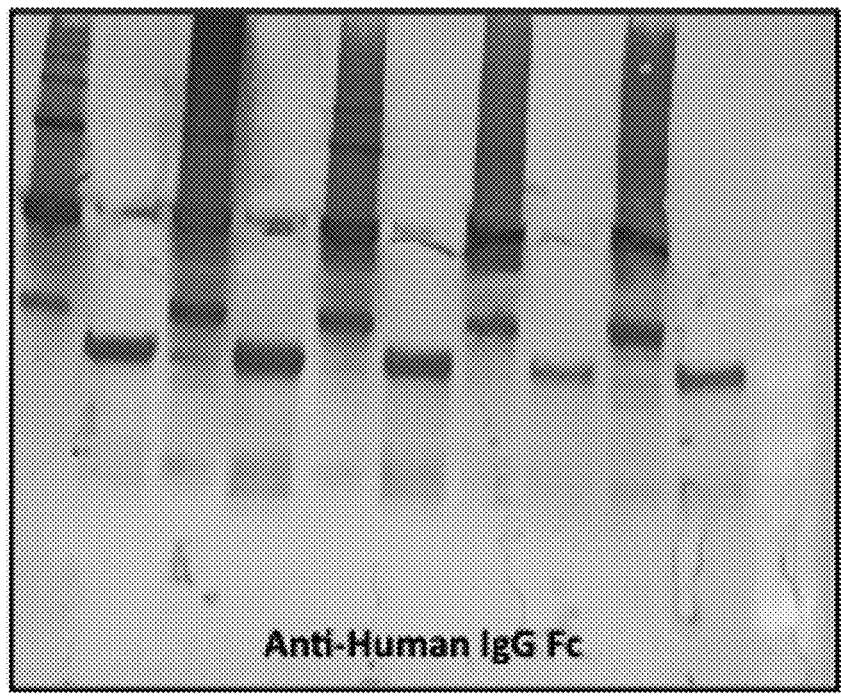

Plasmid constructs containing nucleotide sequences encoding each of the canine IL17A-hFC-polyHis mutants were transiently transfected into 293 cells and the supernatants concentrated 3-fold. Each mutant was separated by SDS-PAGE (25 L per lane) in the presence or absence of DTT and the proteins transferred to a PVDF membrane. The blot was probed using either Clone C antibody or anti-human IgG Fc (control). The Western blots are shown in FIG. 7. The signal in lane 3 of the Clone C antibody blot is reduced compared to the control blot suggesting that Clone C antibody binds to canine IL17A in the region having the Mutant 1 mutations (R71L, L73W, I82T). The Western analysis of mutant canine IL17A suggests that Clone C antibody binds to an epitope within amino acids 65 to 88 of SEQ ID NO: 22, for example an epitope comprising the amino acid sequence of SEQ ID NO: 23 or SEQ ID NO: 51.

Example 16

Modification of Canine Fc Complement Binding Activity

Canine IgG-B Fc (SEQ ID NO: 45) and canine IgG-C Fc (SEQ ID NO: 46) have complement activity. To potentially reduce the binding of C1q to IgG-B Fc and IgG-C Fc, and/or potentially reduce complement-mediated immune responses, IgG-B Fc and IgG-C Fc variants may be prepared having an amino acid substitution of Lys at amino acid position 110 of SEQ ID NO:45 or of Lys at amino acid position 108 of SEQ ID NO: 46 with any amino acid except Lys. These amino acid substitutions were identified after analysis of the protein sequence and 3-D structure modeling of canine IgG-B and IgG-C compared to canine IgG-A and IgG-D, which are understood to not exhibit complement activity.

For example, canine IgG-B Fc variant 1 may be prepared by substituting the Lys at amino acid position 110 of SEQ ID NO: 45 with Arg (SEQ ID NO: 47) and canine IgG-C Fc variant 1 may be prepared by substituting the Lys at position 108 of SEQ ID NO: 46 with Arg (SEQ ID NO: 48).

The determine the binding affinity of C1q to canine IgG-B Fc variant 1, a biosensor binding analysis was performed. In this assay, the affinity of C1q to a fusion protein of a canine IL4 receptor ECD and IL13 receptor ECD (IL4R/IL13R) and canine IgG-B Fc wild-type (IL4R/IL13R-canine IgG-B, SEQ ID NO: 95) or to canine IgG-B Fc variant 1 (IL4R/IL13R-canine IgG-B variant 1, SEQ ID NO: 96) was tested. Briefly, canine IL4 was biotinylated. Biotinylated canine IL4 was captured on streptavidin sensor tips. Either IL4R/IL13R-canine IgG-B wild-type (25ug/mL) or IL4R/IL13R-canine IgG-B variant 1 (25 g/mL) were complexed to the IL4-bound biosensors. Subsequently, the complex was used to bind human C1q at 250 g/mL (Catalog No. 204876-1MG;

Sigma Aldrich). Then, the ability of human C1q to bind to either complex was measured. Reduced binding between human C1q and IL4R/IL13R-canine IgG-B variant 1 was observed when compared to IL4R/IL13R-canine IgG-B wild-type.

Example 17

Modification of Canine Fc CD16 Binding Activity

Canine IgG-B Fc (SEQ ID NO: 45) and canine IgG-C Fc (SEQ ID NO: 46) have CD16 binding activity. To potentially reduce the binding of CD16 to IgG-B Fc and IgG-C Fc, and/or potentially reduce antibody-dependent cell-mediated cytotoxicity (ADCC), canine IgG-B Fc and IgG-C Fc variants may be prepared having one or more of the amino acid substitutions listed in Table 7. The amino acid substitution(s) were identified after analysis of the protein sequence and 3-D structure modeling of canine IgG-B and IgG-C compared to canine IgG-A and IgG-D, which are understood to not exhibit ADCC activity.

TABLE 7

| Original residue position | | |
| --- | --- | --- |
| Canine IgG-B Fc (SEQ ID NO: 45) | Canine IgG-C Fc (SEQ ID NO: 46) | Substitution(s) |
| Glu (55) | Glu (53) | Any amino acid except Glu |
| Lys (114) | Lys (112) | Any amino acid except Lys |
| Ala (115) | Ala (113) | Any amino acid except Ala |

For example, canine IgG-B-Fc variant 2 (SEQ ID NO: 49) may be prepared by substituting Glu at position 55 of canine IgG-B Fc (SEQ ID NO: 45) with Gly, Lys at position 114 with Ile, and Ala at position 115 with Gly. As another example, canine IgG-C-Fc variant 2 (SEQ ID NO: 50) may be prepared by substituting Glu at position 53 of canine IgG-C Fc (SEQ ID NO: 46) with Gly, Lys at position 112 with Ile, and Ala at position 113 with Gly.

The binding of any of the canine IgG-B Fc or IgG-C Fc variants to CD16 may be determined and compared to the binding of another IgG Fc to CD16 (e.g., the corresponding canine IgG-B Fc or IgG-C Fc wild-type, other canine IgG Fc variant, etc.). The binding assay described in Example 16 may be used.

---

The invention claimed is:

1. A monoclonal antibody that binds to canine IL17A, wherein the antibody comprises:
   (i) a CDR-H1 comprising the amino acid sequence of SEQ ID NO: 1, a CDR-H2 comprising the amino acid sequence of SEQ ID NO: 2, and a CDR-H3 comprising the amino acid sequence of SEQ ID NO: 3, and
   (ii) a CDR-L1 sequence comprising the amino acid sequence of SEQ ID NO: 8, a CDR-L2 sequence comprising the amino acid sequence of SEQ ID NO: 9, and a CDR-L3 sequence comprising the amino acid sequence of SEQ ID NO: 10.

2. The monoclonal antibody of claim 1, wherein the antibody binds to canine IL17A with a dissociation constant ($K_d$) of less than $1\times10^{-8}$ M, as measured by biolayer interferometry.

3. The monoclonal antibody of claim 1, wherein the antibody is a caninized, a felinized, an equinized, or a chimeric antibody.

4. The monoclonal antibody of claim 1, wherein the antibody comprises:
   (i) a variable light chain sequence comprising an amino acid sequence having at least 95% sequence identity to the amino acid sequence of SEQ ID NO: 24; and
   (ii) a variable heavy chain sequence comprising an amino acid sequence having at least 95% sequence identity to the amino acid sequence of SEQ ID NO: 25.

5. The monoclonal antibody of claim 1, wherein the antibody comprises:
   a variable light chain sequence comprising an amino acid sequence having 100% sequence identity to SEQ ID NO: 24 and a variable heavy chain sequence comprising an amino acid sequence having 100% sequence identity to SEQ ID NO: 25.

6. The monoclonal antibody of claim 1, wherein the antibody comprises (a) a canine heavy chain constant region selected from an IgG-A, IgG-B, IgG-C, and IgG-D constant region; (b) a feline heavy chain constant region selected from an IgG-1a, IgG-1b, and IgG-2 constant region; or (c) an equine heavy chain constant region selected from an IgG-1, IgG-2, IgG-3, IgG-4, IgG-5, IgG-6, and IgG-7 constant region.

7. The monoclonal antibody of claim 1, wherein the antibody is an antibody fragment chosen from an Fv, scFv, Fab, Fab', F(ab')2, and Fab'-SH fragment.

8. A nucleic acid encoding the monoclonal antibody of claim 1.

9. A host cell comprising the nucleic acid of claim 8.

10. A method of producing a monoclonal antibody comprising culturing the host cell of claim 9 and isolating the monoclonal antibody.

11. A pharmaceutical composition comprising the monoclonal antibody of claim 1 and a pharmaceutically acceptable carrier.

12. A method of treating a companion animal species having an IL17A-induced condition, the method comprising administering to the companion animal species a therapeutically effective amount of the monoclonal antibody of claim 1.

13. A method of reducing IL17A signaling function in a cell, the method comprising exposing to the cell the monoclonal antibody of claim 1 under conditions permissive for binding of the antibody to extracellular IL17A, thereby reducing binding to IL17A receptor and/or reducing IL17A signaling function by the cell.

14. A method for detecting IL17A in a sample from a companion animal species comprising contacting the sample with the monoclonal antibody of claim 1 under conditions permissive for binding of the antibody to IL17A, and detecting whether a complex is formed between the monoclonal antibody and IL17A in the sample.

15. The monoclonal antibody of claim 1, further comprising one or more of:

(i) the variable region heavy chain framework 1 (HC-FR1) sequence of SEQ ID NO: 4;

(ii) the variable region heavy chain framework 2 (HC-FR2) sequence of SEQ ID NO: 5;

(iii) the variable region heavy chain framework 3 (HC-FR3) sequence of SEQ ID NO: 6;

(iv) the variable region heavy chain framework 4 (HC-FR4) sequence of SEQ ID NO: 7;

(v) the variable region light chain framework 1 (LC-FR1) sequence of SEQ ID NO:11;

(vi) the variable region light chain framework 2 (LC-FR2) sequence of SEQ ID NO:12;

(vii) the variable region light chain framework 3 (LC-FR3) sequence of SEQ ID NO: 13; and (viii) the variable region light chain framework 4 (LC-FR4) sequence of SEQ ID NO: 14.

16. The monoclonal antibody of claim 1, wherein the monoclonal antibody binds to SEQ ID NO: 22.

* * * * *